US011162120B2

United States Patent
Marlière

(10) Patent No.: US 11,162,120 B2
(45) Date of Patent: Nov. 2, 2021

(54) ENZYMATIC PRODUCTION OF AN ACYL PHOSPHATE FROM A 2-HYDROXYALDEHYDE

(71) Applicant: Scientist of Fortune, S.A., Luxembourg (LU)

(72) Inventor: Philippe Marlière, Tournai (BE)

(73) Assignees: Scientist of Fortune, S.A., Luxembourg (LU); Global Bioenergies, Evry Cedex (FR)

( * ) Notice: Subject to any disclaimer, the term of this patent is extended or adjusted under 35 U.S.C. 154(b) by 669 days.

(21) Appl. No.: 15/758,824

(22) PCT Filed: Sep. 8, 2016

(86) PCT No.: PCT/EP2016/071150
§ 371 (c)(1),
(2) Date: Mar. 9, 2018

(87) PCT Pub. No.: WO2017/042254
PCT Pub. Date: Mar. 16, 2017

(65) Prior Publication Data
US 2020/0248215 A1    Aug. 6, 2020

(30) Foreign Application Priority Data

Sep. 10, 2015  (EP) .................................... 15184678
Feb. 29, 2016  (EP) .................................... 16157821

(51) Int. Cl.
| C12N 9/14 | (2006.01) |
| C12N 9/88 | (2006.01) |
| C12P 9/00 | (2006.01) |
| C12N 9/10 | (2006.01) |
| C12N 9/12 | (2006.01) |

(52) U.S. Cl.
CPC .............. *C12P 9/00* (2013.01); *C12N 9/1029* (2013.01); *C12N 9/1217* (2013.01); *C12N 9/14* (2013.01); *C12N 9/88* (2013.01); *C12Y 203/01008* (2013.01); *C12Y 203/01019* (2013.01); *C12Y 207/02001* (2013.01); *C12Y 207/02007* (2013.01); *C12Y 207/02012* (2013.01); *C12Y 207/02014* (2013.01); *C12Y 207/02015* (2013.01); *C12Y 306/01007* (2013.01); *C12Y 401/02009* (2013.01); *C12Y 401/02022* (2013.01)

(58) Field of Classification Search
None
See application file for complete search history.

(56) References Cited

U.S. PATENT DOCUMENTS 7,785,858 B2 *  8/2010  Kozlov .................... C12P 7/42
                                               435/243

FOREIGN PATENT DOCUMENTS

WO    2015144447 A1    10/2015
WO    2015181074 A1    12/2015

OTHER PUBLICATIONS

STIC Chemical Structure Search Report generated May 16, 2020. (Year: 2020).*
Schramm et al., Journal of Biological Chemistry, vol. 233, No. 6 pp. 1283-1288 (1958). (Year: 1958).*
Racker, E., Methods in Enzymology, vol. 5, pp. 276-280 (1962). (Year: 1962).*
Petrareanu et al., Applied Microbiology and Biotechnology, vol. 98, pp. 7855-7867 (2014). (Year: 2014).*
International Preliminary Report on Patentability dated Mar. 22, 2018 and received in PCT/EP2016/071150.
European Search Report dated Jan. 12, 2016, received in EP 15 18 4678.
Honjo, et al., "Dual Synthetic Pathway for 3-Hydroxypropionic Acid Production in Engineered *Escherichia coli*", Journal of Bioscience and Bioengineering, vol. 120, No. 2, pp. 199-204, (2015).
Matsakas et al., "New Trends in Microbial Production of 3-Hydroxypropionic Acid", Current Biochemical Engineering, vol. 1, No. 2, pp. 141-154, (2014).
Ruff et al., "Sulphoacetaldehyde Acetyltransferase Yields Acetyl Phosphate: Purification from Alcaligenes Defragrans and Gene Clusters in Taurine Degradation", Biochem J., vol. 369, pp. 275-285, (2003).
Written Opinion and International Search Report dated Nov. 24, 2016 in PCT/EP2016/071150.
EPO Office Action dated Jan. 22, 2019 received in corresponding EP Application 16 777 914.9.
Inoue et al., "Purification and Some Properties of NAD(P)H Dehydrogenase from *Saccharomyces cerevisiae*: Contribution to Glycolytic Methylglyoxal Pathway", Journal of Fermentation and Bioengineering, vol. 77, No. 5, pp. 557-561, (1994).
EPO Office Action dated May 15, 2019 received in corresponding EP Application 16 777 914.9.

* cited by examiner

*Primary Examiner* — Soren Harward
*Assistant Examiner* — Paul D Pyla
(74) *Attorney, Agent, or Firm* — Michele M. Wales; Inhouse Patent Counsel, LLC

(57) ABSTRACT

Described is a method for the enzymatic production of an acyl phosphate from a 2-hydroxyaldehyde using a phosphoketolase or a sulfoacetaldehyde acetyltransferase.

33 Claims, 5 Drawing Sheets
Specification includes a Sequence Listing.

wherein R[1] and R[2] are selected independently from H, CH$_3$, CH$_2$OH and C$_2$H$_5$ and wherein if R[1] is H, R[2] cannot be H.

acyl phosphate          carboxylic acid or acyl phosphate          carboxylic acid wherein R¹ and R² are selected independently from H, CH₃, CH₂OH and C₂H₅ and wherein if R¹ is H, R² cannot be H.

wherein R¹ and R² are selected independently from H, CH$_3$, CH$_2$OH and C$_2$H$_5$ and wherein if R¹ is H, R² cannot be H.

SEQUENCE LISTING

<160> NUMBER OF SEQ ID NOS: 20

<210> SEQ ID NO 1
<211> LENGTH: 825
<212> TYPE: PRT
<213> ORGANISM: Bifidobacterium pseudolongum
<220> FEATURE:
<223> OTHER INFORMATION: subsp. globosum

<400> SEQUENCE: 1

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Thr

-continued

```
                20                  25                  30
Asn Tyr Met Ser Ile Gly Gln Ile Tyr Leu Arg Ser Asn Pro Leu Met
                35                  40                  45
Lys Glu Pro Phe Thr Arg Asp Asp Val Lys His Arg Leu Val Gly His
            50                  55                  60
Trp Gly Thr Thr Pro Gly Leu Asn Phe Leu Leu Ala His Ile Asn Arg
65                  70                  75                  80
Leu Ile Ala Asp His Gln Gln Asn Thr Val Phe Ile Met Gly Pro Gly
                85                  90                  95
His Gly Gly Pro Ala Gly Thr Ser Gln Ser Tyr Val Asp Gly Thr Tyr
            100                 105                 110
Thr Glu Tyr Tyr Pro Asn Ile Thr Lys Asp Glu Ala Gly Leu Gln Lys
            115                 120                 125
Phe Phe Arg Gln Phe Ser Tyr Pro Gly Gly Ile Pro Ser His Phe Ala
            130                 135                 140
Pro Glu Thr Pro Gly Ser Ile His Glu Gly Gly Glu Leu Gly Tyr Ala
145                 150                 155                 160
Leu Ser His Ala Tyr Gly Ala Val Met Asn Asn Pro Ser Leu Phe Val
                165                 170                 175
Pro Cys Ile Ile Gly Asp Gly Glu Ala Glu Thr Gly Pro Leu Ala Thr
            180                 185                 190
Gly Trp Gln Ser Asn Lys Leu Val Asn Pro Arg Thr Asp Gly Ile Val
            195                 200                 205
Leu Pro Ile Leu His Leu Asn Gly Tyr Lys Ile Ala Asn Pro Thr Ile
            210                 215                 220
Leu Ala Arg Ile Ser Asp Glu Glu Leu His Asp Phe Phe Arg Gly Met
225                 230                 235                 240
Gly Tyr His Pro Tyr Glu Phe Val Ala Gly Phe Asp Asn Glu Asp His
                245                 250                 255
Met Ser Ile His Arg Arg Phe Ala Glu Leu Phe Glu Thr Ile Phe Asp
            260                 265                 270
Glu Ile Cys Asp Ile Lys Ala Ala Gln Thr Asp Asp Met Thr Arg
            275                 280                 285
Pro Phe Tyr Pro Met Leu Ile Phe Arg Thr Pro Lys Gly Trp Thr Cys
            290                 295                 300
Pro Lys Phe Ile Asp Gly Lys Lys Thr Glu Gly Ser Trp Arg Ala His
305                 310                 315                 320
Gln Val Pro Leu Ala Ser Ala Arg Asp Thr Glu Glu His Phe Glu Val
                325                 330                 335
Leu Lys Gly Trp Leu Glu Ser Tyr Lys Pro Glu Glu Leu Phe Asn Ala
            340                 345                 350
Asp Gly Ser Ile Lys Asp Asp Val Thr Ala Phe Met Pro Lys Gly Asp
            355                 360                 365
Leu Arg Ile Gly Ala Asn Pro Asn Ala Asn Gly Gly Val Ile Arg Glu
            370                 375                 380
Asp Leu Lys Leu Pro Glu Leu Asp Gln Tyr Glu Val Thr Gly Val Lys
385                 390                 395                 400
Glu Tyr Gly His Gly Trp Gly Gln Val Glu Ala Pro Arg Ser Leu Gly
                405                 410                 415
Ala Tyr Cys Arg Asp Ile Ile Lys Asn Asn Pro Asp Ser Phe Arg Ile
            420                 425                 430
Phe Gly Pro Asp Glu Thr Ala Ser Asn Arg Leu Asn Ala Thr Tyr Glu
            435                 440                 445
```

Val Thr Asp Lys Gln Trp Asp Asn Gly Tyr Leu Ser Ser Leu Val Asp
            450                 455                 460

Glu His Met Ala Val Thr Gly Gln Val Thr Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Ile Asn Lys Thr Phe Asn Asn Asp His Val Thr Asn Ile Tyr
                565                 570                 575

Phe Ala Thr Asp Ala Asn Met Leu Leu Ala Ile Ser Glu Lys Cys Phe
            580                 585                 590

Lys Ser Thr Asn Lys Ile Asn Ala Ile Phe Ala Gly Lys Gln Pro Ala
        595                 600                 605

Pro Thr Trp Ile Thr Leu Asp Glu Ala Arg Ala Glu Leu Glu Ala Gly
    610                 615                 620

Ala Ala Glu Trp Lys Trp Ala Ser Asn Ala Glu Asn Asn Asp Glu Val
625                 630                 635                 640

Gln Val Val Leu Ala Ala Gly Asp Val Pro Thr Gln Glu Ile Met
                645                 650                 655

Ala Ala Ser Asp Ala Leu Asn Lys Met Gly Ile Lys Phe Lys Val Val
            660                 665                 670

Asn Val Val Asp Leu Leu Lys Leu Gln Ser Arg Glu Asn Asn Asp Glu
        675                 680                 685

Ala Leu Thr Asp Glu Glu Phe Thr Asp Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Asn Val Val Gly Tyr Lys Glu
                725                 730                 735

Gln Gly Ser Thr Thr Pro Phe Asp Met Val Arg Val Asn Asp Met
            740                 745                 750

Asp Arg Tyr Ala Leu Gln Ala Ala Leu Lys Met Ile Asp Ala Asp
        755                 760                 765

Lys Tyr Ala Asp Lys Ile Asp Glu Leu Asn Ala Phe Arg Gln Lys Ala
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Thr Ala Gly Asp Asn Glu
            820                 825

<210> SEQ ID NO 2
<211> LENGTH: 796
<212> TYPE: PRT
<213> ORGANISM: Clostridium acetobutylicum

<400> SEQUENCE: 2

```
Met Gln Ser Ile Ile Gly Lys His Lys Asp Glu Gly Lys Ile Thr Pro
 1               5                  10                  15

Glu Tyr Leu Lys Lys Ile Asp Ala Tyr Trp Arg Ala Ala Asn Phe Ile
             20                  25                  30

Ser Val Gly Gln Leu Tyr Leu Asp Asn Pro Leu Leu Arg Glu Pro
         35                  40                  45

Leu Lys Pro Glu His Leu Lys Arg Lys Val Val Gly His Trp Gly Thr
 50                  55                  60

Ile Pro Gly Gln Asn Phe Ile Tyr Ala His Leu Asn Arg Val Ile Lys
 65                  70                  75                  80

Lys Tyr Asp Leu Asp Met Ile Tyr Val Ser Gly Pro Gly His Gly Gly
                 85                  90                  95

Gln Val Met Val Ser Asn Ser Tyr Leu Asp Gly Thr Tyr Ser Glu Val
             100                 105                 110

Tyr Pro Asn Val Ser Arg Asp Leu Asn Gly Leu Lys Lys Leu Cys Lys
             115                 120                 125

Gln Phe Ser Phe Pro Gly Gly Ile Ser Ser His Met Ala Pro Glu Thr
130                 135                 140

Pro Gly Ser Ile Asn Glu Gly Glu Leu Gly Tyr Ser Leu Ala His
145                 150                 155                 160

Ser Phe Gly Ala Val Phe Asp Asn Pro Asp Leu Ile Thr Ala Cys Val
                 165                 170                 175

Val Gly Asp Gly Glu Ala Glu Thr Gly Pro Leu Ala Thr Ser Trp Gln
             180                 185                 190

Ala Asn Lys Phe Leu Asn Pro Val Thr Asp Gly Ala Val Leu Pro Ile
             195                 200                 205

Leu His Leu Asn Gly Tyr Lys Ile Ser Asn Pro Thr Val Leu Ser Arg
210                 215                 220

Ile Pro Lys Asp Glu Leu Glu Lys Phe Phe Glu Gly Asn Gly Trp Lys
225                 230                 235                 240

Pro Tyr Phe Val Glu Gly Glu Asp Pro Glu Thr Met His Lys Leu Met
                 245                 250                 255

Ala Glu Thr Leu Asp Ile Val Thr Glu Glu Ile Leu Asn Ile Gln Lys
             260                 265                 270

Asn Ala Arg Glu Asn Asn Asp Cys Ser Arg Pro Lys Trp Pro Met Ile
             275                 280                 285

Val Leu Arg Thr Pro Lys Gly Trp Thr Gly Pro Lys Phe Val Asp Gly
290                 295                 300

Val Pro Asn Glu Gly Ser Phe Arg Ala His Gln Val Pro Leu Ala Val
305                 310                 315                 320

Asp Arg Tyr His Thr Glu Asn Leu Asp Gln Leu Glu Glu Trp Leu Lys
                 325                 330                 335

Ser Tyr Lys Pro Glu Glu Leu Phe Asp Glu Asn Tyr Arg Leu Ile Pro
             340                 345                 350

Glu Leu Glu Glu Leu Thr Pro Lys Gly Asn Lys Arg Met Ala Ala Asn
             355                 360                 365

Leu His Ala Asn Gly Gly Leu Leu Leu Arg Glu Leu Arg Thr Pro Asp
370                 375                 380

Phe Arg Asp Tyr Ala Val Asp Val Pro Thr Pro Gly Ser Thr Val Lys
385                 390                 395                 400

Gln Asp Met Ile Glu Leu Gly Lys Tyr Val Arg Asp Val Val Lys Leu
                 405                 410                 415
```

```
Asn Glu Asp Thr Arg Asn Phe Arg Ile Phe Gly Pro Asp Glu Thr Met
            420                 425                 430

Ser Asn Arg Leu Trp Ala Val Phe Glu Gly Thr Lys Arg Gln Trp Leu
        435                 440                 445

Ser Glu Ile Lys Glu Pro Asn Asp Glu Phe Leu Ser Asn Asp Gly Arg
    450                 455                 460

Ile Val Asp Ser Met Leu Ser Glu His Leu Cys Glu Gly Trp Leu Glu
465                 470                 475                 480

Gly Tyr Leu Leu Thr Gly Arg His Gly Phe Phe Ala Ser Tyr Glu Ala
                485                 490                 495

Phe Leu Arg Ile Val Asp Ser Met Ile Thr Gln His Gly Lys Trp Leu
                500                 505                 510

Lys Val Thr Ser Gln Leu Pro Trp Arg Lys Asp Ile Ala Ser Leu Asn
            515                 520                 525

Leu Ile Ala Thr Ser Asn Val Trp Gln Gln Asp His Asn Gly Tyr Thr
        530                 535                 540

His Gln Asp Pro Gly Leu Leu Gly His Ile Val Asp Lys Lys Pro Glu
545                 550                 555                 560

Ile Val Arg Ala Tyr Leu Pro Ala Asp Ala Asn Thr Leu Leu Ala Val
                565                 570                 575

Phe Asp Lys Cys Leu His Thr Lys His Lys Ile Asn Leu Leu Val Thr
                580                 585                 590

Ser Lys His Pro Arg Gln Gln Trp Leu Thr Met Asp Gln Ala Val Lys
            595                 600                 605

His Val Glu Gln Gly Ile Ser Ile Trp Asp Trp Ala Ser Asn Asp Lys
        610                 615                 620

Gly Gln Glu Pro Asp Val Val Ile Ala Ser Cys Gly Asp Thr Pro Thr
625                 630                 635                 640

Leu Glu Ala Leu Ala Ala Val Thr Ile Leu His Glu His Leu Pro Glu
                645                 650                 655

Leu Lys Val Arg Phe Val Asn Val Val Asp Met Met Lys Leu Leu Pro
                660                 665                 670

Glu Asn Glu His Pro His Gly Leu Ser Asp Lys Asp Tyr Asn Ala Leu
            675                 680                 685

Phe Thr Thr Asp Lys Pro Val Ile Phe Ala Phe His Gly Phe Ala His
        690                 695                 700

Leu Ile Asn Gln Leu Thr Tyr His Arg Glu Asn Arg Asn Leu His Val
705                 710                 715                 720

His Gly Tyr Met Glu Glu Gly Thr Ile Thr Thr Pro Phe Asp Met Arg
                725                 730                 735

Val Gln Asn Lys Leu Asp Arg Phe Asn Leu Val Lys Asp Val Val Glu
            740                 745                 750

Asn Leu Pro Gln Leu Gly Asn Arg Gly Ala His Leu Val Gln Leu Met
        755                 760                 765

Asn Asp Lys Leu Val Glu His Asn Gln Tyr Ile Arg Glu Val Gly Glu
770                 775                 780

Asp Leu Pro Glu Ile Thr Asn Trp Gln Trp His Val
                785                 790                 795

<210> SEQ ID NO 3
<211> LENGTH: 822
<212> TYPE: PRT
<213> ORGANISM: Lactococcus lactis
<220> FEATURE:
```

<223> OTHER INFORMATION: subsp. lactis

<400> SEQUENCE: 3

```
Met Thr Glu Tyr Asn Ser Glu Ala Tyr Leu Lys Lys Leu Asp Lys Trp
1               5                   10                  15

Trp Arg Ala Ala Thr Tyr Leu Gly Ala Gly Met Ile Phe Leu Lys Glu
                20                  25                  30

Asn Pro Leu Phe Ser Val Thr Gly Thr Pro Ile Lys Ala Glu Asn Leu
            35                  40                  45

Lys Ala Asn Pro Ile Gly His Trp Gly Thr Val Ser Gly Gln Thr Phe
        50                  55                  60

Leu Tyr Ala His Ala Asn Arg Leu Ile Asn Lys Tyr Asn Gln Lys Met
65                  70                  75                  80

Phe Tyr Met Gly Gly Pro Gly His Gly Gln Ala Met Val Val Pro
                85                  90                  95

Ser Tyr Leu Asp Gly Ser Tyr Thr Glu Ala Tyr Pro Glu Ile Thr Gln
            100                 105                 110

Asp Leu Glu Gly Met Ser Arg Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Val Leu Ser His Ala Thr Gly Ala Ile Leu
145                 150                 155                 160

Asp Gln Pro Glu Gln Ile Ala Phe Ala Val Val Gly Asp Gly Glu Ala
                165                 170                 175

Glu Thr Gly Pro Leu Met Thr Ser Trp His Ser Ile Lys Phe Ile Asn
            180                 185                 190

Pro Lys Asn Asp Gly Ala Ile Leu Pro Ile Leu Asp Leu Asn Gly Phe
        195                 200                 205

Lys Ile Ser Asn Pro Thr Leu Phe Ala Arg Thr Ser Asp Val Asp Ile
    210                 215                 220

Arg Lys Phe Phe Glu Gly Leu Gly Tyr Ser Pro Arg Tyr Ile Glu Asn
225                 230                 235                 240

Asp Asp Ile His Asp Tyr Met Ala Tyr His Lys Leu Ala Ala Glu Val
                245                 250                 255

Phe Asp Lys Ala Ile Glu Asp Ile His Gln Ile Gln Lys Asp Ala Arg
            260                 265                 270

Glu Asp Asn Arg Tyr Gln Asn Gly Glu Ile Pro Ala Trp Pro Ile Val
        275                 280                 285

Ile Ala Arg Leu Pro Lys Gly Trp Gly Pro Arg Tyr Asn Asp Trp
    290                 295                 300

Ser Gly Pro Lys Phe Asp Gly Lys Gly Met Pro Ile Glu His Ser Phe
305                 310                 315                 320

Arg Ala His Gln Val Pro Leu Pro Leu Ser Ser Lys Asn Met Gly Thr
                325                 330                 335

Leu Pro Glu Phe Val Lys Trp Met Thr Ser Tyr Gln Pro Glu Thr Leu
            340                 345                 350

Phe Asn Ala Asp Gly Ser Leu Lys Glu Glu Leu Arg Asp Phe Ala Pro
        355                 360                 365

Lys Gly Glu Met Arg Met Ala Ser Asn Pro Val Thr Asn Gly Gly Val
    370                 375                 380

Asp Tyr Ser Asn Leu Val Leu Pro Asp Trp Gln Glu Phe Ala Asn Pro
385                 390                 395                 400
```

-continued

```
Ile Ser Glu Asn Asn Arg Gly Lys Leu Leu Pro Asp Thr Asn Asp Asn
                405                 410                 415
Met Asp Met Asn Val Leu Ser Lys Tyr Phe Ala Glu Ile Val Lys Leu
        420                 425                 430
Asn Pro Thr Arg Phe Arg Leu Phe Gly Pro Asp Glu Thr Met Ser Asn
            435                 440                 445
Arg Phe Trp Glu Met Phe Lys Val Thr Asn Arg Gln Trp Met Gln Val
450                 455                 460
Ile Lys Asn Pro Asn Asp Glu Phe Ile Ser Pro Glu Gly Arg Ile Ile
465                 470                 475                 480
Asp Ser Gln Leu Ser Glu His Gln Ala Glu Gly Trp Leu Gly Tyr
                485                 490                 495
Thr Leu Thr Gly Arg Thr Gly Val Phe Ala Ser Tyr Glu Ser Phe Leu
                500                 505                 510
Arg Val Val Asp Ser Met Leu Thr Gln His Phe Lys Trp Ile Arg Gln
            515                 520                 525
Ala Ala Asp Gln Lys Trp Arg His Asp Tyr Pro Ser Leu Asn Val Ile
        530                 535                 540
Ser Thr Ser Thr Val Phe Gln Gln Asp His Asn Gly Tyr Thr His Gln
545                 550                 555                 560
Asp Pro Gly Met Leu Thr His Leu Ala Glu Lys Ser Asp Phe Ile
                565                 570                 575
Arg Gln Tyr Leu Pro Ala Asp Gly Asn Thr Leu Leu Ala Val Phe Asp
                580                 585                 590
Arg Ala Phe Gln Asp Arg Ser Lys Ile Asn His Ile Val Ala Ser Lys
            595                 600                 605
Gln Pro Arg Gln Gln Trp Phe Thr Lys Glu Glu Ala Glu Lys Leu Ala
        610                 615                 620
Thr Asp Gly Ile Ala Thr Ile Asp Trp Ala Ser Thr Ala Lys Asp Gly
625                 630                 635                 640
Glu Ala Val Asp Leu Val Phe Ala Ser Ala Gly Ala Glu Pro Thr Ile
                645                 650                 655
Glu Thr Leu Ala Ala Leu His Leu Val Asn Glu Val Phe Pro Gln Ala
                660                 665                 670
Lys Phe Arg Tyr Val Asn Val Glu Leu Gly Arg Leu Gln Lys Lys
            675                 680                 685
Lys Gly Ala Leu Asn Gln Glu Arg Glu Leu Ser Asp Glu Glu Phe Glu
        690                 695                 700
Lys Tyr Phe Gly Pro Ser Gly Thr Pro Val Ile Phe Gly Phe His Gly
705                 710                 715                 720
Tyr Glu Asp Leu Ile Glu Ser Ile Phe Tyr Gln Arg Gly His Asp Gly
                725                 730                 735
Leu Ile Val His Gly Tyr Arg Glu Asp Gly Asp Ile Thr Thr Thr Tyr
                740                 745                 750
Asp Met Arg Val Tyr Ser Glu Leu Asp Arg Phe His Gln Ala Ile Asp
            755                 760                 765
Ala Met Gln Val Leu Tyr Val Asn Arg Lys Val Asn Gln Gly Leu Ala
        770                 775                 780
Lys Ala Phe Ile Asp Arg Met Glu Arg Thr Leu Val Lys His Phe Glu
785                 790                 795                 800
Val Thr Arg Asn Glu Gly Val Asp Ile Pro Glu Phe Thr Glu Trp Val
                805                 810                 815
Trp Ser Asp Leu Lys Lys
```

-continued

820

<210> SEQ ID NO 4
<211> LENGTH: 598
<212> TYPE: PRT
<213> ORGANISM: Castellaniella defragrans

<400> SEQUENCE: 4

Met Ala Asn Asp Thr Arg Gln Val Val Gln Gly Val Gln Glu Met Thr
1               5                   10                  15

Pro Ser Glu Ala Phe Val Glu Thr Met Val Ala Asn Gly Val Thr Glu
            20                  25                  30

Ile Phe Gly Ile Met Gly Ser Ala Phe Met Asp Ala Met Asp Ile Phe
        35                  40                  45

Ala Pro Ala Gly Ile Lys Leu Ile Pro Val Val His Glu Gln Gly Ala
    50                  55                  60

Ala His Met Ala Asp Gly Phe Ala Arg Val Ser Gly Arg Thr Gly Val
65                  70                  75                  80

Val Ile Gly Gln Asn Gly Pro Gly Ile Ser Asn Cys Val Thr Ala Ile
                85                  90                  95

Ala Ala Ala Tyr Trp Ala His Thr Pro Val Val Ile Val Thr Pro Glu
            100                 105                 110

Ala Gly Thr Thr Gly Ile Gly Leu Gly Gly Phe Gln Glu Ala Arg Gln
        115                 120                 125

Leu Pro Met Phe Gln Glu Phe Thr Lys Tyr Gln Gly His Val Thr His
    130                 135                 140

Pro Ala Arg Met Ala Glu Tyr Thr Ala Arg Cys Phe Ala Arg Ala Arg
145                 150                 155                 160

Asp Glu Met Gly Pro Ala Gln Leu Asn Ile Pro Arg Asp Tyr Phe Tyr
                165                 170                 175

Gly Lys Ile Lys Cys Glu Ile Pro Leu Pro Gln Pro Leu Asp Arg Gly
            180                 185                 190

Pro Gly Gly Ala Gln Ser Leu Asp Ala Ala Ala Arg Leu Leu Ala Glu
        195                 200                 205

Ala Lys Phe Pro Val Ile Ile Ser Gly Gly Val Val Met Gly Asp
    210                 215                 220

Ala Val Glu Glu Cys Lys Ala Leu Ala Glu Arg Leu Gly Ala Pro Val
225                 230                 235                 240

Val Asn Ser Tyr Leu His Asn Asp Ser Phe Pro Ala Ser His Pro Leu
                245                 250                 255

Trp Cys Gly Pro Leu Gly Tyr Gln Gly Ser Lys Ala Ala Met Lys Leu
            260                 265                 270

Leu Ala Asp Ala Asp Val Val Leu Ala Leu Gly Thr Arg Leu Gly Pro
        275                 280                 285

Phe Gly Thr Leu Pro Gln His Gly Leu Asp Tyr Trp Pro Lys Asn Ala
    290                 295                 300

Arg Ile Ile Gln Val Asp Ala Asp Ser Lys Met Leu Gly Leu Val Lys
305                 310                 315                 320

Lys Ile Thr Val Gly Val Cys Gly Asp Ala Lys Ala Ser Ala Ala Glu
                325                 330                 335

Ile Ser Arg Arg Ile Asp Gly Met Lys Leu Ala Cys Asp Ala Asn Lys
            340                 345                 350

Ala Glu Arg Ala Ala Arg Ile Gln Ala Glu Lys Asp Ala Trp Glu Gln
        355                 360                 365

-continued

```
Glu Leu Thr Asp Trp Thr His Glu Arg Asp Pro Phe Ser Leu Asp Met
    370                 375                 380

Ile Glu Glu Gln Ser Lys Glu Glu Gly Asn Trp Leu His Pro Arg Gln
385                 390                 395                 400

Val Leu Arg Glu Leu Glu Lys Ala Met Pro Glu Asp Val Met Val Ser
                405                 410                 415

Thr Asp Ile Gly Asn Ile Asn Ser Val Ala Asn Ser Tyr Leu Arg Phe
            420                 425                 430

Glu Lys Pro Arg Ser Phe Phe Ala Ala Met Ser Trp Gly Asn Cys Gly
            435                 440                 445

Tyr Ala Phe Pro Thr Ile Ile Gly Ala Lys Val Ala Ala Pro His Arg
450                 455                 460

Pro Ala Val Ser Tyr Ala Gly Asp Gly Ala Trp Gly Met Ser Met Ser
465                 470                 475                 480

Glu Ile Met Thr Cys Val Arg His Asp Ile Pro Val Thr Ala Val Val
                485                 490                 495

Phe His Asn Arg Gln Trp Gly Ala Glu Lys Lys Asn Gln Val Asp Phe
            500                 505                 510

Tyr Asn Arg Arg Phe Val Ala Gly Glu Leu Glu Ser Glu Ser Phe Ala
            515                 520                 525

Gly Ile Ala Arg Ala Met Gly Ala Glu Gly Val Val Val Asp Arg Ile
        530                 535                 540

Glu Asp Val Gly Pro Ala Leu Lys Lys Ala Ile Asp Ala Gln Met Asn
545                 550                 555                 560

Asp Arg Lys Thr Thr Val Ile Glu Ile Met Cys Thr Arg Glu Leu Gly
                565                 570                 575

Asp Pro Phe Arg Arg Asp Ala Leu Ser Lys Pro Val Arg Leu Leu Glu
            580                 585                 590

Lys Tyr Arg Asp Tyr Thr
            595

<210> SEQ ID NO 5
<211> LENGTH: 603
<212> TYPE: PRT
<213> ORGANISM: Alcaligenes xylosoxidans
<220> FEATURE:
<223> OTHER INFORMATION: subsp. xylosoxidans

<400> SEQUENCE: 5

Met Ala Ala Thr Asp Asn Arg Lys Val Val Glu Gly Val His Lys Met
1               5                   10                  15

Thr Pro Ser Glu Ala Phe Val Glu Thr Cys Val Ala Asn Gly Val Ser
                20                  25                  30

Glu Met Phe Gly Ile Met Gly Ser Ala Phe Met Asp Ala Met Asp Ile
            35                  40                  45

Phe Ala Pro Ala Gly Ile Arg Leu Ile Pro Val His Glu Gln Gly
50                  55                  60

Ala Ala His Met Ala Asp Gly Tyr Ala Arg Val Ser Gly Arg His Gly
65                  70                  75                  80

Val Val Ile Gly Gln Asn Gly Pro Gly Ile Ser Asn Cys Val Thr Gly
                85                  90                  95

Ile Ala Ala Ala Tyr Trp Ala His Ser Pro Val Val Ile Val Thr Pro
            100                 105                 110

Glu Thr Gly Thr Met Gly Met Gly Leu Gly Gly Phe Gln Glu Ala Asn
        115                 120                 125
```

-continued

```
Gln Leu Pro Met Phe Gln Glu Phe Thr Lys Tyr Gln Gly His Val Cys
    130                 135                 140

Asn Pro Lys Arg Met Ala Glu Phe Thr Gly Arg Val Phe Asp Arg Ala
145                 150                 155                 160

Met Ser Glu Met Gly Pro Thr Gln Leu Asn Ile Pro Arg Asp Tyr Phe
                165                 170                 175

Tyr Gly Glu Ile Glu Cys Glu Ile Pro Lys Pro Met Arg Val Asp Arg
                180                 185                 190

Gly His Gly Gly Glu Ala Ser Leu Gln Ala Ala Val Glu Leu Leu Lys
            195                 200                 205

Thr Ala Lys Phe Pro Val Ile Leu Ala Gly Gly Val Val Met Gly
    210                 215                 220

Asp Ala Val Glu Glu Ala Lys Gln Leu Ala Glu Arg Leu Gly Ala Pro
225                 230                 235                 240

Val Ala Thr Gly Tyr Leu Arg Asn Asp Ala Phe Pro Ala Lys His Pro
                245                 250                 255

Leu Trp Ala Gly Pro Leu Gly Tyr Gln Gly Ser Lys Ala Ala Met Lys
            260                 265                 270

Leu Ile Ala Gln Ala Asp Val Val Ile Ala Leu Gly Ser Arg Met Gly
    275                 280                 285

Pro Phe Gly Thr Leu Pro Gln His Gly Met Asp Tyr Trp Pro Lys Ala
    290                 295                 300

Ala Lys Ile Ile Gln Ile Glu Ala Asp His Thr Asn Leu Gly Leu Val
305                 310                 315                 320

Lys Lys Ile Ala Val Gly Ile Asn Gly Asp Ala Lys Ala Val Ala Ala
                325                 330                 335

Glu Leu Ser Arg Arg Leu Ala Asp Val Thr Leu Gly Cys Asp Ala Thr
            340                 345                 350

Lys Ala Ala Arg Ala Asp Thr Ile Ala Thr Glu Lys Ala Ala Trp Glu
    355                 360                 365

Lys Glu Leu Asp Gly Trp Thr His Glu Arg Asp Pro Tyr Ser Leu Asp
370                 375                 380

Met Ile Glu Glu Ala Lys Gly Glu Arg Thr Pro Thr Gly Gly Ser Tyr
385                 390                 395                 400

Leu His Pro Arg Gln Val Leu Arg Glu Leu Glu Lys Ala Met Pro Ala
                405                 410                 415

Arg Val Met Val Ser Thr Asp Ile Gly Asn Ile Asn Ser Val Ala Asn
            420                 425                 430

Ser Tyr Leu Arg Phe Asp Glu Pro Arg Ser Phe Phe Ala Pro Met Ser
    435                 440                 445

Phe Gly Asn Cys Gly Tyr Ala Leu Pro Thr Ile Gly Ala Lys Cys
    450                 455                 460

Ala Ala Pro Asp Arg Pro Ala Ile Ala Tyr Ala Gly Asp Gly Ala Trp
465                 470                 475                 480

Gly Met Ser Met Met Glu Ile Met Thr Ala Val Arg His Asp Ile Pro
                485                 490                 495

Val Thr Ala Val Val Phe His Asn Arg Gln Trp Gly Ala Glu Lys Lys
            500                 505                 510

Asn Gln Val Asp Phe Tyr Asn Arg Arg Phe Val Ala Gly Glu Leu Glu
    515                 520                 525

Ser Glu Ser Phe Ser Asp Ile Ala Lys Ala Met Gly Ala Glu Gly Ile
    530                 535                 540

Val Val Asp His Ile Glu Asp Val Gly Pro Ala Leu Gln Lys Ala Ile
```

```
545                 550                 555                 560
Asp Met Gln Met Lys Glu Gly Lys Thr Cys Val Ile Glu Ile Met Cys
                565                 570                 575

Thr Arg Glu Leu Gly Asp Pro Phe Arg Arg Asp Ala Leu Ser Lys Pro
            580                 585                 590

Val Arg Met Leu Asp Lys Tyr Lys Asp Tyr Val
        595                 600

<210> SEQ ID NO 6
<211> LENGTH: 584
<212> TYPE: PRT
<213> ORGANISM: Desulfonispora thiosulfatigenes

<400> SEQUENCE: 6

Met Ala Lys Val Lys Met Thr Pro Ser Glu Ala Met Thr Glu Val Leu
1               5                   10                  15

Val Asn Glu Gly Val Thr His Val Thr Gly Ile Leu Gly Ser Ala Phe
            20                  25                  30

Met Asp Met Leu Asp Leu Trp Pro Thr Ala Gly Ile Glu Phe Ile Ala
        35                  40                  45

Val Arg His Glu Gln Thr Ala Gly His Met Gln Asp Ala Tyr Cys Arg
    50                  55                  60

Ile Thr Gly Lys Ala Ser Val Cys Ile Gly Gln Asn Gly Pro Gly Val
65                  70                  75                  80

Thr Asn Leu Val Thr Cys Val Ala Ala Asn Gln Ala His Thr Pro
                85                  90                  95

Met Val Val Leu Gly Pro Ser Ala Gly Thr Pro Thr Val Gly Trp Asp
            100                 105                 110

Gly Phe Gln Glu Cys Asp Gln Val Ser Ile Phe Arg Ser Ile Thr Lys
        115                 120                 125

Gln Val Leu Gln Val Pro His Pro Ser Arg Ala Gly Asp Val Leu Arg
    130                 135                 140

Thr Ala Phe Arg Ile Ala Tyr Ala Glu Arg Gly Pro Val Tyr Val Asp
145                 150                 155                 160

Ile Pro Arg Asn Tyr Phe Tyr Gly Glu Val Tyr Glu Glu Ile Leu Arg
                165                 170                 175

Pro Asp Gln Tyr Arg Ala Met Asn Val Arg Gly Ala Gly Asp Ala Thr
            180                 185                 190

Glu Leu Ala Arg Ala Thr Glu Ile Leu Ala Ala Ala Lys Asn Pro Val
        195                 200                 205

Ile Ile Ser Gly Arg Gly Val Val Asp Ala Asp Ala Phe Ala Glu Val
    210                 215                 220

Lys Glu Ile Ala His Met Leu Thr Ala Pro Val Ala Met Ser Tyr Leu
225                 230                 235                 240

His Asn Asp Thr Tyr Pro Ala Asp Asp Glu Leu Trp Val Gly Pro Ile
                245                 250                 255

Gly Tyr Met Gly Ala Lys Ser Ala Met Tyr Ser Leu Gln Asp Ala Asp
            260                 265                 270

Val Ile Leu Ala Ile Gly Ser Arg Leu Ser Val Phe Gly Thr Leu Pro
        275                 280                 285

Gln Tyr Asp Ile Asn Tyr Phe Pro Glu Asn Ala Lys Ile Ile Gln Ile
    290                 295                 300

Glu Val Asn Pro Lys Gln Ile Gly Arg Arg His Pro Val Thr Val Pro
305                 310                 315                 320
```

Ile Ile Gly Asp Ala Lys Leu Ala Thr Ala Glu Leu Ile Lys Leu Leu
            325                 330                 335

Lys Ala Lys Gly Asp Val Lys Pro Asn Ala Glu Arg Leu Ala Lys Ile
        340                 345                 350

Gln Glu Arg Arg Asn Asp Trp Phe Lys Glu Ile Glu Glu Met Ala Met
    355                 360                 365

Met Pro Gly Asn Pro Ile Asn Pro Arg Arg Val Leu Phe Glu Val Ala
370                 375                 380

Lys Leu Met Pro Glu Asp Ala Ile Leu Thr Thr Asp Ile Gly Asn Val
385                 390                 395                 400

Ala Ser Thr Ala Asn Ser Tyr Phe Lys Phe Thr Lys Pro Lys Lys His
                405                 410                 415

Ile Ala Ala Leu Thr Phe Gly Asn Thr Gly Phe Ala Tyr Gln Ala Gly
            420                 425                 430

Leu Gly Ala Gln Met Ala Glu Pro Asp Ser Pro Val Ala Ile Val
        435                 440                 445

Gly Asp Gly Ala Trp Gly Gln Ser Leu His Glu Ile Ser Thr Ala Val
    450                 455                 460

Gln Tyr Lys Leu Pro Val Ile Ala Cys Val Phe Arg Asn Met Ala Trp
465                 470                 475                 480

Cys Ala Glu Lys Lys Asn Gln Ile Asp Phe Tyr Asn Asn Arg Phe Val
                485                 490                 495

Gly Thr Glu Ile Pro Asn Pro Ile Ser Phe Ile Pro Ala Ala Glu Ala
            500                 505                 510

Phe Gly Ala Lys Gly Ile Arg Val Glu Lys Pro Glu Asp Ile Ala Asp
        515                 520                 525

Ala Phe Lys Gln Gly Leu Ala Trp Arg Ala Glu Gly His Pro Val Val
    530                 535                 540

Leu Glu Phe Val Val Asp Gly Thr Ile Leu Ala Pro Pro Phe Arg Lys
545                 550                 555                 560

Asp Ala Leu Ala Leu Pro Thr Arg Tyr Leu Pro Lys Tyr Glu His Leu
                565                 570                 575

Asp Ala Lys Tyr Phe Pro Lys Asn
            580

<210> SEQ ID NO 7
<211> LENGTH: 591
<212> TYPE: PRT
<213> ORGANISM: Rhizobium meliloti
<220> FEATURE:
<223> OTHER INFORMATION: strain 1021

<400> SEQUENCE: 7

Met Lys Met Thr Thr Glu Glu Ala Phe Val Lys Val Leu Gln Met His
1               5                   10                  15

Gly Ile Glu His Ala Phe Gly Ile Ile Gly Ser Ala Met Met Pro Val
            20                  25                  30

Ser Asp Leu Phe Pro Lys Ala Gly Ile Arg Phe Trp Asp Cys Ala His
        35                  40                  45

Glu Thr Asn Ala Gly Met Met Ala Asp Gly Phe Ser Arg Ala Thr Gly
    50                  55                  60

Thr Met Ser Met Ala Ile Gly Gln Asn Gly Pro Gly Val Thr Gly Phe
65                  70                  75                  80

Ile Thr Ala Met Lys Thr Ala Tyr Trp Asn His Thr Pro Leu Leu Met
                85                  90                  95

-continued

```
Val Thr Pro Gln Ala Ala Asn Lys Thr Ile Gly Gln Gly Gly Phe Gln
            100                 105                 110
Glu Val Asp Gln Met Ala Met Phe Glu Glu Met Val Cys Tyr Gln Glu
        115                 120                 125
Glu Val Arg Asp Pro Ser Arg Ile Pro Glu Val Leu Asn Arg Val Ile
    130                 135                 140
Glu Lys Ala Trp Arg Gly Cys Ala Pro Ala Gln Ile Asn Ile Pro Arg
145                 150                 155                 160
Asp Phe Trp Thr Gln Val Ile Asp Val Asp Leu Pro Arg Ile Val Arg
                165                 170                 175
Phe Glu Arg Pro Ala Gly Gly Pro Ala Ala Ile Ala Gln Ala Ala Arg
            180                 185                 190
Leu Leu Ser Glu Ala Lys Phe Pro Val Ile Leu Asn Gly Ala Gly Val
        195                 200                 205
Val Ile Gly Asn Ala Ile Gln Glu Ser Met Ala Leu Ala Glu Lys Leu
    210                 215                 220
Asp Ala Pro Val Cys Cys Gly Tyr Gln His Asn Asp Ala Phe Pro Gly
225                 230                 235                 240
Ser His Arg Leu Ser Val Gly Pro Leu Gly Tyr Asn Gly Ser Lys Ala
                245                 250                 255
Ala Met Glu Leu Ile Ser Lys Ala Asp Val Val Leu Ala Leu Gly Thr
            260                 265                 270
Arg Leu Asn Pro Phe Ser Thr Leu Pro Gly Tyr Gly Ile Asp Tyr Trp
        275                 280                 285
Pro Lys Asp Ala Ala Ile Ile Gln Val Asp Ile Asn Ala Asp Arg Ile
    290                 295                 300
Gly Leu Thr Lys Lys Val Thr Val Gly Ile Cys Gly Asp Ala Lys Gln
305                 310                 315                 320
Val Ala Gln Gln Ile Leu Gln Leu Ala Pro Ala Ala Gly Asp Ala
                325                 330                 335
Ser Arg Glu Glu Arg Lys Ala Leu Val His Gln Thr Arg Ser Ala Trp
            340                 345                 350
Leu Gln Gln Leu Ser Ser Met Asp His Glu Asp Asp Pro Gly Thr
        355                 360                 365
Glu Trp Asn Val Gly Ala Arg Gln Arg Glu Pro Asp Arg Met Ser Pro
    370                 375                 380
Arg Gln Val Trp Arg Ala Ile Gln Ala Val Leu Pro Lys Glu Ala Ile
385                 390                 395                 400
Ile Ser Thr Asp Ile Gly Asn Asn Cys Ala Ile Gly Asn Ala Tyr Pro
                405                 410                 415
Ser Phe Glu Gln Gly Arg Lys Tyr Leu Ala Pro Gly Met Phe Gly Pro
            420                 425                 430
Cys Gly Tyr Gly Phe Pro Ser Ile Val Gly Ala Lys Ile Gly Cys Pro
        435                 440                 445
Asp Val Pro Val Val Gly Phe Ala Gly Asp Gly Ala Phe Gly Ile Ser
    450                 455                 460
Met Asn Glu Met Thr Ser Ile Gly Arg Glu Gly Trp Pro Ala Ile Thr
465                 470                 475                 480
Met Val Ile Phe Arg Asn Tyr Gln Trp Gly Ala Glu Lys Arg Asn Thr
                485                 490                 495
Thr Leu Trp Tyr Asp Asn Asn Phe Val Gly Thr Glu Leu Asn Pro Asn
            500                 505                 510
Leu Ser Tyr Ala Lys Val Ala Asp Gly Cys Gly Leu Lys Gly Val Thr
```

```
            515                 520                 525
Val Asp Thr Pro Ala Ala Leu Thr Glu Ala Leu Ala Lys Ala Ile Glu
    530                 535                 540

Asp Gln Ala Lys Gly Ile Thr Thr Phe Val Glu Val Val Leu Asn Gln
545                 550                 555                 560

Glu Leu Gly Glu Pro Phe Arg Arg Asp Ala Met Lys Lys Pro Val Ala
                565                 570                 575

Val Ala Gly Ile Asp Arg Ala Asp Met Arg Thr Gln Arg Arg Met
            580                 585                 590

<210> SEQ ID NO 8
<211> LENGTH: 603
<212> TYPE: PRT
<213> ORGANISM: Roseovarius nubinhibens

<400> SEQUENCE: 8

Met Leu Phe Arg Ala Ser Gln Pro Glu Asp Lys Pro Met Lys Met Thr
1               5                   10                  15

Thr Glu Glu Ala Phe Val Lys Thr Leu Gln Met His Gly Ile Gln His
                20                  25                  30

Ala Phe Gly Ile Ile Gly Ser Ala Met Met Pro Ile Ser Asp Ile Phe
            35                  40                  45

Gly Lys Ala Gly Ile Thr Phe Trp Asp Cys His Glu Gly Ser Gly
    50                  55                  60

Gly Met Met Ala Asp Gly Tyr Thr Arg Ala Thr Gly Lys Met Ser Met
65                  70                  75                  80

Met Ile Ala Gln Asn Gly Pro Gly Ile Thr Asn Phe Val Thr Ala Val
                85                  90                  95

Lys Thr Ala Tyr Trp Asn His Thr Pro Leu Leu Leu Val Thr Pro Gln
            100                 105                 110

Ala Ala Asn Lys Thr Met Gly Gln Gly Gly Phe Gln Glu Val Glu Gln
        115                 120                 125

Met Ala Ala Phe Lys Asp Met Val Cys Tyr Gln Glu Glu Val Arg Asp
130                 135                 140

Pro Thr Arg Met Ala Glu Val Leu Asn Arg Val Ile Leu Asn Ala Lys
145                 150                 155                 160

Arg Tyr Ser Ala Pro Ala Gln Ile Asn Val Pro Arg Asp Tyr Phe Thr
                165                 170                 175

Gln Val Ile Asp Ile Glu Leu Pro Lys Ile Val Asp Phe Glu Arg Pro
            180                 185                 190

Ser Gly Gly Glu Glu Ala Leu Asp Glu Ala Ala Lys Leu Leu Ser Glu
        195                 200                 205

Ala Lys Phe Pro Val Ile Leu Asn Gly Ala Gly Val Ile Leu Ala Gly
210                 215                 220

Ala Ile Pro Ala Thr Ala Glu Leu Ala Glu Arg Leu Asp Ala Pro Val
225                 230                 235                 240

Cys Cys Gly Tyr Gln His Asn Asp Ala Phe Pro Gly Ser His Pro Leu
                245                 250                 255

His Ala Gly Pro Leu Gly Tyr Asn Gly Ser Lys Ala Gly Met Glu Leu
            260                 265                 270

Ile Ser Lys Ala Asp Val Val Leu Ala Leu Gly Thr Arg Leu Asn Pro
        275                 280                 285

Phe Ser Thr Leu Pro Gly Tyr Gly Ile Asp Tyr Trp Pro Lys Asp Ala
    290                 295                 300
```

-continued

Lys Ile Ile Gln Val Asp Val Lys Pro Glu Arg Ile Gly Leu Thr Lys
305                 310                 315                 320

Pro Val Ala Val Gly Ile Val Gly Asp Ala Lys Lys Val Ala Lys Thr
            325                 330                 335

Ile Leu Ala Lys Leu Ser Asp Thr Ala Gly Asp Ala Asp Arg Glu Glu
        340                 345                 350

Arg Lys Ala Thr Ile Ala Lys Thr Lys Ser Ala Trp Ala Gln Glu Leu
    355                 360                 365

Ser Ser Met Asp His Glu Gln Asp Asp Pro Gly Thr Thr Trp Asn Glu
370                 375                 380

Arg Ala Arg Gly Ala Lys Pro Asp Trp Met Ser Pro Arg Met Ala Trp
385                 390                 395                 400

Arg Ala Ile Gln Ala Ala Leu Pro Lys Glu Ala Ile Ile Ser Ser Asp
            405                 410                 415

Ile Gly Asn Asn Cys Ala Ile Gly Asn Ala Tyr Pro Ser Phe Glu Glu
        420                 425                 430

Gly Arg Lys Tyr Leu Ala Pro Gly Leu Phe Gly Pro Cys Gly Tyr Gly
    435                 440                 445

Leu Pro Ala Val Val Gly Ala Lys Ile Gly Cys Pro Asp Thr Pro Val
450                 455                 460

Val Gly Phe Ser Gly Asp Gly Ala Phe Gly Ile Ala Val Asn Glu Leu
465                 470                 475                 480

Thr Ala Ile Gly Arg Gly Glu Trp Pro Ala Val Thr His Val Val Phe
            485                 490                 495

Arg Asn Tyr Gln Trp Gly Ala Glu Lys Arg Asn Ser Thr Leu Trp Phe
        500                 505                 510

Asp Asp Asn Phe Val Gly Thr Glu Leu Asp Glu Gln Val Ser Tyr Ala
    515                 520                 525

Gly Ile Ala Lys Ala Cys Gly Leu Lys Gly Val Val Ala Arg Thr Met
530                 535                 540

Asp Glu Leu Thr Asp Ala Leu Asp Gln Ala Ile Lys Asp Gln Lys Ala
545                 550                 555                 560

Gly Thr Thr Thr Leu Ile Glu Ala Met Ile Asn Gln Glu Leu Gly Glu
            565                 570                 575

Pro Phe Arg Arg Asp Ala Met Lys Lys Pro Val Ala Val Ala Gly Ile
        580                 585                 590

Asp Pro Ala Asp Met Arg Glu Gln Gln Val Asp
    595                 600

<210> SEQ ID NO 9
<211> LENGTH: 402
<212> TYPE: PRT
<213> ORGANISM: Salmonella typhimurium
<220> FEATURE:
<223> OTHER INFORMATION: strain LT2 / SGSC1412 / ATCC 700720
<220> FEATURE:
<223> OTHER INFORMATION: Salty propionate kinase

<400> SEQUENCE: 9

Met Asn Glu Phe Pro Val Val Leu Val Ile Asn Cys Gly Ser Ser Ser
1               5                   10                  15

Ile Lys Phe Ser Val Leu Asp Val Ala Thr Cys Asp Val Leu Met Ala
            20                  25                  30

Gly Ile Ala Asp Gly Met Asn Thr Glu Asn Ala Phe Leu Ser Ile Asn
        35                  40                  45

Gly Asp Lys Pro Ile Asn Leu Ala His Ser Asn Tyr Glu Asp Ala Leu

```
        50                  55                  60
Lys Ala Ile Ala Phe Glu Leu Glu Lys Arg Asp Leu Thr Asp Ser Val
 65                  70                  75                  80

Ala Leu Ile Gly His Arg Ile Ala His Gly Gly Glu Leu Phe Thr Gln
                 85                  90                  95

Ser Val Ile Ile Thr Asp Glu Ile Asp Asn Ile Arg Arg Val Ser
                100                 105                 110

Pro Leu Ala Pro Leu His Asn Tyr Ala Asn Leu Ser Gly Ile Asp Ala
                115                 120                 125

Ala Arg His Leu Phe Pro Ala Val Arg Gln Val Ala Val Phe Asp Thr
130                 135                 140

Ser Phe His Gln Thr Leu Ala Pro Glu Ala Tyr Leu Tyr Gly Leu Pro
145                 150                 155                 160

Trp Glu Tyr Phe Ser Ser Leu Gly Val Arg Arg Tyr Gly Phe His Gly
                165                 170                 175

Thr Ser His Arg Tyr Val Ser Arg Arg Ala Tyr Glu Leu Leu Asp Leu
                180                 185                 190

Asp Glu Lys Asp Ser Gly Leu Ile Val Ala His Leu Gly Asn Gly Ala
                195                 200                 205

Ser Ile Cys Ala Val Arg Asn Gly Gln Ser Val Asp Thr Ser Met Gly
210                 215                 220

Met Thr Pro Leu Glu Gly Leu Met Met Gly Thr Arg Ser Gly Asp Val
225                 230                 235                 240

Asp Phe Gly Ala Met Ala Trp Ile Ala Lys Glu Thr Gly Gln Thr Leu
                245                 250                 255

Ser Asp Leu Glu Arg Val Val Asn Lys Glu Ser Gly Leu Leu Gly Ile
                260                 265                 270

Ser Gly Leu Ser Ser Asp Leu Arg Val Leu Glu Lys Ala Trp His Glu
                275                 280                 285

Gly His Glu Arg Ala Arg Leu Ala Ile Lys Thr Phe Val His Arg Ile
                290                 295                 300

Ala Arg His Ile Ala Gly His Ala Ala Ser Leu His Arg Leu Asp Gly
305                 310                 315                 320

Ile Ile Phe Thr Gly Gly Ile Gly Glu Asn Ser Val Leu Ile Arg Gln
                325                 330                 335

Leu Val Ile Glu His Leu Gly Val Leu Gly Leu Thr Leu Asp Val Glu
                340                 345                 350

Met Asn Lys Gln Pro Asn Ser His Gly Glu Arg Ile Ile Ser Ala Asn
                355                 360                 365

Pro Ser Gln Val Ile Cys Ala Val Ile Pro Thr Asn Glu Glu Lys Met
370                 375                 380

Ile Ala Leu Asp Ala Ile His Leu Gly Asn Val Lys Ala Pro Val Glu
385                 390                 395                 400

Phe Ala

<210> SEQ ID NO 10
<211> LENGTH: 402
<212> TYPE: PRT
<213> ORGANISM: Escherichia coli
<220> FEATURE:
<223> OTHER INFORMATION: strain K12
<220> FEATURE:
<223> OTHER INFORMATION: Propionate kinase

<400> SEQUENCE: 10
```

```
Met Asn Glu Phe Pro Val Leu Val Ile Asn Cys Gly Ser Ser Ser
1               5                   10                  15

Ile Lys Phe Ser Val Leu Asp Ala Ser Asp Cys Glu Val Leu Met Ser
            20                  25                  30

Gly Ile Ala Asp Gly Ile Asn Ser Glu Asn Ala Phe Leu Ser Val Asn
                35                  40                  45

Gly Gly Glu Pro Ala Pro Leu Ala His His Ser Tyr Glu Gly Ala Leu
50                  55                  60

Lys Ala Ile Ala Phe Glu Leu Glu Lys Arg Asn Leu Asn Asp Ser Val
65                  70                  75                  80

Ala Leu Ile Gly His Arg Ile Ala His Gly Gly Ser Ile Phe Thr Glu
                85                  90                  95

Ser Ala Ile Ile Thr Asp Glu Val Ile Asp Asn Ile Arg Arg Val Ser
                100                 105                 110

Pro Leu Ala Pro Leu His Asn Tyr Ala Asn Leu Ser Gly Ile Glu Ser
                115                 120                 125

Ala Gln Gln Leu Phe Pro Gly Val Thr Gln Val Ala Val Phe Asp Thr
130                 135                 140

Ser Phe His Gln Thr Met Ala Pro Glu Ala Tyr Leu Tyr Gly Leu Pro
145                 150                 155                 160

Trp Lys Tyr Tyr Glu Glu Leu Gly Val Arg Arg Tyr Gly Phe His Gly
                165                 170                 175

Thr Ser His Arg Tyr Val Ser Gln Arg Ala His Ser Leu Leu Asn Leu
                180                 185                 190

Ala Glu Asp Asp Ser Gly Leu Val Val Ala His Leu Gly Asn Gly Ala
                195                 200                 205

Ser Ile Cys Ala Val Arg Asn Gly Gln Ser Val Asp Thr Ser Met Gly
                210                 215                 220

Met Thr Pro Leu Glu Gly Leu Met Met Gly Thr Arg Ser Gly Asp Val
225                 230                 235                 240

Asp Phe Gly Ala Met Ser Trp Val Ala Ser Gln Thr Asn Gln Ser Leu
                245                 250                 255

Gly Asp Leu Glu Arg Val Val Asn Lys Glu Ser Gly Leu Leu Gly Ile
                260                 265                 270

Ser Gly Leu Ser Ser Asp Leu Arg Val Leu Glu Lys Ala Trp His Glu
                275                 280                 285

Gly His Glu Arg Ala Gln Leu Ala Ile Lys Thr Phe Val His Arg Ile
                290                 295                 300

Ala Arg His Ile Ala Gly His Ala Ala Ser Leu Arg Arg Leu Asp Gly
305                 310                 315                 320

Ile Ile Phe Thr Gly Gly Ile Gly Glu Asn Ser Ser Leu Ile Arg Arg
                325                 330                 335

Leu Val Met Glu His Leu Ala Val Leu Gly Leu Glu Ile Asp Thr Glu
                340                 345                 350

Met Asn Asn Arg Ser Asn Ser Cys Gly Glu Arg Ile Val Ser Ser Glu
                355                 360                 365

Asn Ala Arg Val Ile Cys Ala Val Ile Pro Thr Asn Glu Glu Lys Met
                370                 375                 380

Ile Ala Leu Asp Ala Ile His Leu Gly Lys Val Asn Ala Pro Ala Glu
385                 390                 395                 400

Phe Ala

<210> SEQ ID NO 11
```

<211> LENGTH: 329
<212> TYPE: PRT
<213> ORGANISM: Corynebacterium glutamicum
<220> FEATURE:
<223> OTHER INFORMATION: strain ATCC 13032
<220> FEATURE:
<223> OTHER INFORMATION: Phosphate acetyltransferase

<400> SEQUENCE: 11

Met Ser Ala Glu Leu Phe Glu Asn Trp Leu Leu Lys Arg Ala Arg Ala
1               5                   10                  15

Glu His Ser His Ile Val Leu Pro Glu Gly Asp Asp Arg Ile Leu
            20                  25                  30

Met Ala Ala His Gln Leu Leu Asp Gln Asp Ile Cys Asp Ile Thr Ile
        35                  40                  45

Leu Gly Asp Pro Val Lys Ile Lys Glu Arg Ala Thr Glu Leu Gly Leu
    50                  55                  60

His Leu Asn Thr Ala Tyr Leu Val Asn Pro Leu Thr Asp Pro Arg Leu
65                  70                  75                  80

Glu Glu Phe Ala Glu Gln Phe Ala Glu Leu Arg Lys Ser Lys Ser Val
                85                  90                  95

Thr Ile Asp Glu Ala Arg Glu Ile Met Lys Asp Ile Ser Tyr Phe Gly
            100                 105                 110

Thr Met Met Val His Asn Gly Asp Ala Asp Gly Met Val Ser Gly Ala
        115                 120                 125

Ala Asn Thr Thr Ala His Thr Ile Lys Pro Ser Phe Gln Ile Ile Lys
    130                 135                 140

Thr Val Pro Glu Ala Ser Val Val Ser Ser Ile Phe Leu Met Val Leu
145                 150                 155                 160

Arg Gly Arg Leu Trp Ala Phe Gly Asp Cys Ala Val Asn Pro Asn Pro
                165                 170                 175

Thr Ala Glu Gln Leu Gly Glu Ile Ala Val Val Ser Ala Lys Thr Ala
            180                 185                 190

Ala Gln Phe Gly Ile Asp Pro Arg Val Ala Ile Leu Ser Tyr Ser Thr
        195                 200                 205

Gly Asn Ser Gly Gly Gly Ser Asp Val Asp Arg Ala Ile Asp Ala Leu
    210                 215                 220

Ala Glu Ala Arg Arg Leu Asn Pro Glu Leu Cys Val Asp Gly Pro Leu
225                 230                 235                 240

Gln Phe Asp Ala Ala Val Asp Pro Gly Val Ala Arg Lys Lys Met Pro
                245                 250                 255

Asp Ser Asp Val Ala Gly Gln Ala Asn Val Phe Ile Phe Pro Asp Leu
            260                 265                 270

Glu Ala Gly Asn Ile Gly Tyr Lys Thr Ala Gln Arg Thr Gly His Ala
        275                 280                 285

Leu Ala Val Gly Pro Ile Leu Gln Gly Leu Asn Lys Pro Val Asn Asp
    290                 295                 300

Leu Ser Arg Gly Ala Thr Val Pro Asp Ile Val Asn Thr Val Ala Ile
305                 310                 315                 320

Thr Ala Ile Gln Ala Gly Gly Arg Ser
                325

<210> SEQ ID NO 12
<211> LENGTH: 301
<212> TYPE: PRT
<213> ORGANISM: Clostridium acetobutylicum
<220> FEATURE:

<223> OTHER INFORMATION: strain ATCC 824 / DSM 792 / JCM 1419 / LMG 5710 / VKM B-1787
<220> FEATURE:
<223> OTHER INFORMATION: Phosphate butyryltransferase

<400> SEQUENCE: 12

```
Met Ile Lys Ser Phe Asn Glu Ile Ile Met Lys Val Lys Ser Lys Glu
1               5                   10                  15

Met Lys Lys Val Ala Val Ala Val Ala Gln Asp Glu Pro Val Leu Glu
            20                  25                  30

Ala Val Arg Asp Ala Lys Lys Asn Gly Ile Ala Asp Ala Ile Leu Val
        35                  40                  45

Gly Asp His Asp Glu Ile Val Ser Ile Ala Leu Lys Ile Gly Met Asp
    50                  55                  60

Val Asn Asp Phe Glu Ile Val Asn Glu Pro Asn Val Lys Lys Ala Ala
65                  70                  75                  80

Leu Lys Ala Val Glu Leu Val Ser Thr Gly Lys Ala Asp Met Val Met
                85                  90                  95

Lys Gly Leu Val Asn Thr Ala Thr Phe Leu Arg Ser Val Leu Asn Lys
            100                 105                 110

Glu Val Gly Leu Arg Thr Gly Lys Thr Met Ser His Val Ala Val Phe
        115                 120                 125

Glu Thr Glu Lys Phe Asp Arg Leu Leu Phe Leu Thr Asp Val Ala Phe
    130                 135                 140

Asn Thr Tyr Pro Glu Leu Lys Glu Lys Ile Asp Ile Val Asn Asn Ser
145                 150                 155                 160

Val Lys Val Ala His Ala Ile Gly Ile Glu Asn Pro Lys Val Ala Pro
                165                 170                 175

Ile Cys Ala Val Glu Val Ile Asn Pro Lys Met Pro Ser Thr Leu Asp
            180                 185                 190

Ala Ala Met Leu Ser Lys Met Ser Asp Arg Gly Gln Ile Lys Gly Cys
        195                 200                 205

Val Val Asp Gly Pro Leu Ala Leu Asp Ile Ala Leu Ser Glu Glu Ala
    210                 215                 220

Ala His His Lys Gly Val Thr Gly Glu Val Ala Gly Lys Ala Asp Ile
225                 230                 235                 240

Phe Leu Met Pro Asn Ile Glu Thr Gly Asn Val Met Tyr Lys Thr Leu
                245                 250                 255

Thr Tyr Thr Thr Asp Ser Lys Asn Gly Gly Ile Leu Val Gly Thr Ser
            260                 265                 270

Ala Pro Val Val Leu Thr Ser Arg Ala Asp Ser His Glu Thr Lys Met
        275                 280                 285

Asn Ser Ile Ala Leu Ala Ala Leu Val Ala Gly Asn Lys
    290                 295                 300
```

<210> SEQ ID NO 13
<211> LENGTH: 384
<212> TYPE: PRT
<213> ORGANISM: Lactobacillus casei
<220> FEATURE:
<223> OTHER INFORMATION: strain W56

<400> SEQUENCE: 13

```
Met Arg Asp Cys Thr Thr Glu Arg Arg Cys Leu Met Thr Met His Pro
1               5                   10                  15

Lys Arg Asp Val Val Ile Val Ile Asn Pro Gly Ser Thr Ser Ser Lys
            20                  25                  30
```

```
Ile Ala Leu Phe Lys Ala Gly Lys Met Val Ala Glu Arg Thr Leu Asn
        35                  40                  45

His Ser Leu Ala Glu Leu Ser Gln Phe Asp Ser Val Ile Ala Gln Lys
    50                  55                  60

Asp Phe Arg Met Gln Ala Ile Gln Glu Phe Leu Ala Asp Gln Asp Phe
65                  70                  75                  80

Ser Ala Ser Glu Val Leu Ala Val Ala Gly Arg Gly Gly Leu Leu Lys
                85                  90                  95

Pro Ile Pro Gly Gly Thr Tyr Ala Val Asn Glu Ala Met Leu Asp Asp
            100                 105                 110

Leu Thr Ala Ala Lys Arg Asn Glu His Ala Ser Asn Leu Gly Ala Gly
            115                 120                 125

Leu Ala Gln Gln Val Ala Asp Gln Tyr Gly Val Lys Ala Tyr Val Val
        130                 135                 140

Asp Pro Pro Val Val Asp Glu Leu Gln Pro Leu Ala Arg Ile Ser Gly
145                 150                 155                 160

Leu Lys Gly Ile Glu Arg His Ser Ala Ala His Val Leu Asn Gln Lys
                165                 170                 175

Ala Met Ala Arg Gln Val Leu Ala Thr Met Gly Lys Thr Tyr Ala Thr
            180                 185                 190

Ser Arg Val Ile Val Ala His Ile Gly Gly Gly Leu Ser Ile His Ala
        195                 200                 205

His Glu Asn Gly Arg Met Ile Asp Gly Asn Asn Gly Ile Asp Gly Glu
    210                 215                 220

Gly Pro Tyr Ser Pro Glu Arg Ala Gly Ser Leu Pro Leu Val Asp Phe
225                 230                 235                 240

Val Ala Lys Val Leu Ala Glu Arg Leu Thr Leu Asp Gln Val Lys Lys
                245                 250                 255

Leu Leu Ala Ser Gln Ser Gly Leu Arg Ser Tyr Leu Asn Asp Ile Ser
            260                 265                 270

Ile Lys Asn Ile Val Thr Arg Ile Ala Glu Gly Asp Glu Thr Ala Lys
        275                 280                 285

Phe Tyr Leu Asp Gly Met Ile Tyr Gln Ile Lys Lys Gln Ile Ala Glu
    290                 295                 300

Met Ala Gly Val Leu Asn Gly Gln Val Asp Val Ile Ile Leu Thr Gly
305                 310                 315                 320

Gly Ala Ala Tyr Ala Thr Ala Val Thr Val Pro Leu Gln His Asp Leu
                325                 330                 335

Ala Trp Ile Ala Pro Val Val Arg Pro Gly Glu Met Glu Met Gln
            340                 345                 350

Ala Leu Tyr Glu Gly Val Met Arg Val Leu Asn His Glu Glu Pro Val
    355                 360                 365

Arg Val Tyr Gln Ser Asp Ala Ser Thr Ile Lys Gly Gly Thr Gly Arg
370                 375                 380

<210> SEQ ID NO 14
<211> LENGTH: 370
<212> TYPE: PRT
<213> ORGANISM: Unknown
<220> FEATURE:
<223> OTHER INFORMATION: Geobacillus species, strain GHH01

<400> SEQUENCE: 14

Met Glu Glu Gln Lys Phe Arg Ile Leu Thr Ile Asn Pro Gly Ser Thr
1               5                   10                  15
```

Ser Thr Lys Ile Gly Val Phe Glu Asn Glu Arg Pro Leu Leu Glu Lys
        20                  25                  30

Thr Ile Arg His Glu Ala Asp Val Leu Arg Gln Tyr Lys Thr Ile Ala
        35                  40                  45

Asp Gln Tyr Glu Phe Arg Lys Gln Thr Ile Leu Gln Ala Leu Asp Glu
 50                  55                  60

Glu Gly Ile Asn Leu Ser Lys Leu Ser Ala Val Cys Gly Arg Gly Gly
 65                  70                  75                  80

Leu Leu Arg Pro Ile Glu Gly Thr Tyr Arg Val Asn Glu Ala Met
                 85                  90                  95

Leu Glu Asp Leu Arg Arg Gly Tyr Ser Gly Gln His Ala Ser Asn Leu
                100                 105                 110

Gly Gly Ile Leu Ala His Glu Ile Ala Ser Ala Leu Asn Ile Pro Ala
                115                 120                 125

Phe Ile Val Asp Pro Val Val Asp Glu Leu Asp Pro Ile Ala Arg
130                 135                 140

Ile Ser Gly Phe Pro Leu Ile Glu Arg Arg Ser Ile Phe His Ala Leu
145                 150                 155                 160

Asn Gln Lys Ala Val Ala Arg Arg Val Ala Lys Gln Leu Gly Lys Arg
                165                 170                 175

Tyr Asp Glu Leu Asn Leu Ile Val Ala His Met Gly Gly Ile Thr
                180                 185                 190

Val Gly Ala His Lys Gln Gly Arg Val Val Asp Val Asn Asn Gly Leu
                195                 200                 205

Asp Gly Glu Gly Pro Phe Ser Pro Glu Arg Ala Gly Thr Val Pro Ala
                210                 215                 220

Gly Asp Leu Val Ala Leu Cys Phe Ser Gly Glu Tyr Tyr Arg Glu Glu
225                 230                 235                 240

Ile Met Asn Met Leu Val Gly Gly Gly Leu Val Gly Tyr Leu Gly
                245                 250                 255

Thr Asn Asp Ala Val Lys Val Glu Asn Met Ile Glu Ala Gly Asp Glu
                260                 265                 270

Lys Ala Lys Leu Val Tyr Glu Ala Met Ala Tyr Gln Val Ala Lys Glu
                275                 280                 285

Ile Gly Ala Ala Ser Ala Val Leu Ser Gly Lys Val Asp Ala Ile Ile
                290                 295                 300

Leu Thr Gly Gly Leu Ala Tyr Gly Lys Ser Phe Val Glu Gln Ile Thr
305                 310                 315                 320

Arg Arg Val Gln Trp Ile Ala Asp Val Ile Val His Pro Gly Glu Asn
                325                 330                 335

Glu Leu Gln Ala Leu Ala Glu Gly Ala Leu Arg Val Leu Arg Gly Glu
                340                 345                 350

Glu Glu Glu Lys Val Tyr Pro Gly Glu Ala Val Ser Pro Ile Pro Ala
                355                 360                 365

Arg Arg
    370

<210> SEQ ID NO 15
<211> LENGTH: 299
<212> TYPE: PRT
<213> ORGANISM: Bacillus subtilis
<220> FEATURE:
<223> OTHER INFORMATION: strain 168

<400> SEQUENCE: 15

```
Met Lys Leu Lys Asp Leu Ile Gly Lys Ala Ser Ile His Lys Asn Lys
1               5                   10                  15

Thr Ile Ala Val Ala His Ala Glu Asp Glu Val Ile Arg Ala Val
            20                  25                  30

Lys Leu Ala Ala Glu His Leu Ser Ala Arg Phe Leu Leu Thr Gly Asp
                35                  40                  45

Ser Lys Lys Leu Asn Glu Leu Thr Ser Ser Met Gln Gly His Gln Val
50                  55                  60

Glu Ile Val His Ala Asn Thr Pro Glu Glu Ser Ala Lys Leu Ala Val
65                  70                  75                  80

Arg Ala Val His His Lys Thr Ala Asp Val Leu Met Lys Gly Asn Val
                85                  90                  95

Pro Thr Ser Val Leu Leu Lys Ala Val Leu Asn Arg Gln Glu Gly Leu
                100                 105                 110

Arg Ser Ala Ser Val Leu Ser His Val Ala Val Phe Asp Ile Pro Asp
            115                 120                 125

Phe Asp Arg Leu Met Phe Val Thr Asp Ser Ala Met Asn Ile Ala Pro
            130                 135                 140

Ser Leu Glu Glu Leu Arg Gln Ile Leu Gln Asn Ala Val His Val Ala
145                 150                 155                 160

His Ala Val Gly Asn Asn Met Pro Lys Ala Ala Leu Ala Ala Val
                165                 170                 175

Glu Thr Val Asn Pro Lys Met Glu Ala Thr Val Asn Ala Ala Leu
                180                 185                 190

Ala Gln Met Tyr Lys Arg Gly Gln Ile Lys Gly Cys Ile Val Asp Gly
            195                 200                 205

Pro Leu Ala Leu Asp Asn Ala Val Ser Gln Ile Ala Ala Gln Lys
                210                 215                 220

Lys Ile Ser Gly Asp Val Ala Gly Asn Ala Asp Ile Leu Leu Val Pro
225                 230                 235                 240

Thr Ile Glu Ala Gly Asn Ile Leu Tyr Lys Ser Leu Ile Tyr Phe Ala
                245                 250                 255

Lys Ala Ser Val Ala Ala Val Ile Thr Gly Ala Lys Ala Pro Ile Ala
                260                 265                 270

Leu Thr Ser Arg Ala Asp Ser Ala Glu Asn Lys Leu Tyr Ser Ile Ala
                275                 280                 285

Leu Ala Ile Cys Ala Ser Glu Glu Tyr Thr His
            290                 295

<210> SEQ ID NO 16
<211> LENGTH: 826
<212> TYPE: PRT
<213> ORGANISM: Bifidobacterium gallicum
<220> FEATURE:
<223> OTHER INFORMATION: DSM 20093 = LMG 11596

<400> SEQUENCE: 16

Met Thr Ser Pro Val Ile Gly Thr Pro Trp Gln Lys Leu Asn Arg Pro
1               5                   10                  15

Val Ser Glu Glu Ala Ile Glu Gly Met Asp Lys Tyr Trp Arg Ala Ser
            20                  25                  30

Asn Tyr Met Ser Ile Gly Gln Ile Tyr Leu Arg Ser Asn Pro Leu Met
            35                  40                  45

Lys Glu Pro Phe Thr Arg Asp Asp Val Lys Tyr Arg Leu Val Gly His
50                  55                  60
```

-continued

```
Trp Gly Thr Thr Pro Gly Leu Asn Phe Leu Leu Ala His Ile Asn Arg
 65                  70                  75                  80

Leu Ile Ala Asp His Gln Gln Asn Thr Val Phe Ile Met Gly Pro Gly
                 85                  90                  95

His Gly Gly Pro Ala Gly Thr Ala Gln Ser Tyr Leu Asp Gly Thr Tyr
            100                 105                 110

Thr Glu Tyr Tyr Pro Asn Ile Thr Lys Asp Glu Glu Gly Leu Gln Lys
        115                 120                 125

Phe Phe Arg Gln Phe Ser Tyr Pro Gly Gly Ile Pro Ser His Phe Ala
130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Cys Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
210                 215                 220

Leu Ala Arg Val Ser Asp Glu Glu Leu His Asp Phe Phe Arg Gly Leu
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Asn Thr Asp Asp Met Thr Arg
        275                 280                 285

Pro Phe Tyr Pro Met Leu Ile Phe Arg Thr Pro Lys Gly Trp Thr Cys
290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Asn Trp Met Ala Ser Tyr Lys Pro Glu Glu Leu Phe Asp Asp
            340                 345                 350

Lys Gly Ala Ile Lys Asp Asp Val Val Asp Phe Met Pro Lys Gly Asp
        355                 360                 365

Leu Arg Ile Gly Ala Asn Pro Asn Ala Asn Gly Gly Val Ile Arg Glu
370                 375                 380

Glu Leu Asp Leu Pro Ala Leu Glu Asn Tyr Glu Val Lys Glu Val Lys
385                 390                 395                 400

Glu Phe Gly His Gly Trp Gly Gln Leu Glu Ala Thr Arg Lys Leu Gly
                405                 410                 415

Glu Tyr Thr Arg Asp Ile Ile Lys Asn Asn Pro Asp Ser Phe Arg Ile
            420                 425                 430

Phe Gly Pro Asp Glu Thr Ala Ser Asn Arg Leu Gln Ala Ser Tyr Glu
        435                 440                 445

Val Thr Asn Lys Gln Trp Asp Asn Gly Tyr Leu Ser Lys Asp Leu Val
450                 455                 460

Asp Glu His Met Ala Val Thr Gly Gln Val Thr Glu Gln Leu Ser Glu
465                 470                 475                 480
```

```
His Gln Cys Glu Gly Phe Leu Glu Ala Tyr Leu Leu Thr Gly Arg His
                485                 490                 495
Gly Ile Trp Ser Ser Tyr Glu Ser Phe Val His Val Ile Asp Ser Met
            500                 505                 510
Leu Asn Gln His Ala Lys Trp Leu Glu Ala Thr Val Arg Glu Ile Pro
        515                 520                 525
Trp Arg Lys Pro Ile Ser Ser Met Asn Leu Leu Val Ser Ser His Val
    530                 535                 540
Trp Arg Gln Asp His Asn Gly Phe Ser His Gln Asp Pro Gly Val Thr
545                 550                 555                 560
Ser Val Leu Leu Asn Lys Thr Phe Asn Asn Asp His Val Ile Gly Leu
                565                 570                 575
Tyr Phe Ala Thr Asp Ala Asn Val Leu Leu Ala Ile Ala Glu Lys Cys
            580                 585                 590
Tyr Lys Ser Thr Asn Met Ile Asn Ala Ile Val Ala Gly Lys Gln Pro
        595                 600                 605
Ala Ala Thr Trp Thr Thr Leu Asp Glu Ala Arg Glu Leu Val Ala Lys
    610                 615                 620
Gly Ala Gly Glu Phe Glu Trp Ala Ser Asn Val Lys Thr Asn Asp Glu
625                 630                 635                 640
Ala Glu Ile Val Leu Ala Ser Ala Gly Asp Val Pro Thr Gln Glu Leu
                645                 650                 655
Met Ala Ala Asp Arg Leu Asn Lys Leu Gly Val Lys Phe Lys Val
            660                 665                 670
Val Asn Val Val Asp Leu Ile Lys Leu Gln Ser Ala Lys Glu Asn Asp
        675                 680                 685
Gln Ala Leu Ser Asp Ala Glu Phe Ala Glu Leu Phe Thr Glu Asp Lys
    690                 695                 700
Pro Val Leu Phe Ala Tyr His Ser Tyr Ala His Asp Val Arg Gly Leu
705                 710                 715                 720
Ile Phe Asp Arg Pro Asn His Asp Asn Phe Asn Val Val Gly Tyr Lys
                725                 730                 735
Glu Gln Gly Ser Thr Thr Thr Pro Tyr Asp Met Val Arg Val Asn Asp
            740                 745                 750
Ile Asp Arg Tyr Glu Leu Thr Ala Thr Ala Leu Arg Met Ile Asp Ala
        755                 760                 765
Asp Lys Tyr Ala Asp Glu Ile Lys Lys Leu Glu Asp Phe Arg Ile Glu
    770                 775                 780
Ala Tyr Gln Phe Ala Val Asp Asn Gly Tyr Asp Ile Pro Asp Tyr Thr
785                 790                 795                 800
Asp Trp Val Trp Pro Gly Val Lys Thr Asp Leu Pro Gly Ala Val Ser
                805                 810                 815
Ala Thr Ala Ala Thr Ala Gly Asp Asn Glu
            820                 825

<210> SEQ ID NO 17
<211> LENGTH: 817
<212> TYPE: PRT
<213> ORGANISM: Leuconostoc citreum
<220> FEATURE:
<223> OTHER INFORMATION: strain KM20

<400> SEQUENCE: 17

Met Ala Asp Phe Asp Ser Lys Glu Tyr Leu Glu Leu Val Asp Lys Trp
1               5                   10                  15
```

```
Trp Arg Ala Thr Asn Tyr Leu Ser Ala Gly Met Ile Phe Lys Ser
            20                  25                  30

Asn Pro Leu Phe Ser Val Thr Asn Thr Pro Ile Gln Ala Glu Asp Val
         35                  40                  45

Lys Val Lys Pro Ile Gly His Trp Gly Thr Ile Ser Gly Gln Thr Phe
 50                  55                  60

Leu Tyr Ala His Ala Asn Arg Leu Ile Asn Lys Tyr Asp Leu Asn Met
 65                  70                  75                  80

Phe Tyr Ile Gly Gly Pro Gly His Gly Gln Val Met Val Thr Asn
                 85                  90                  95

Ala Tyr Leu Asp Gly Glu Tyr Thr Glu Asp Tyr Pro Glu Ile Thr Gln
             100                 105                 110

Asp Leu Glu Gly Met Ser Arg Leu Phe Lys Arg Phe Ser Phe Pro Gly
         115                 120                 125

Gly Ile Gly Ser His Met Thr Ala Gln Thr Pro Gly Ser Leu His Glu
             130                 135                 140

Gly Gly Glu Leu Gly Tyr Ser Leu Ser His Ala Phe Gly Ala Val Leu
145                 150                 155                 160

Asp Asn Pro Asp Gln Ile Ala Phe Ala Val Val Gly Asp Gly Glu Ala
                 165                 170                 175

Glu Thr Gly Pro Ser Met Thr Ser Trp His Ser Thr Lys Phe Leu Asn
             180                 185                 190

Ala Lys Asn Asp Gly Ala Val Leu Pro Ile Leu Asp Leu Asn Gly Phe
         195                 200                 205

Lys Ile Ser Asn Pro Thr Ile Phe Ser Arg Met Ser Asp Glu Glu Ile
     210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Ala Tyr His Glu Leu Ala Ala Lys Val
                 245                 250                 255

Leu Asp Gln Ala Ile Glu Asp Ile Gln Ala Ile Gln Lys Asp Ala Arg
             260                 265                 270

Glu Asn Gly Lys Tyr Glu Asp Gly Thr Ile Pro Ala Trp Pro Val Ile
         275                 280                 285

Ile Ala Arg Leu Pro Lys Gly Trp Gly Gly Pro Thr His Asp Glu Asp
     290                 295                 300

Gly Asn Pro Ile Glu Asn Ser Phe Arg Ala His Gln Val Pro Leu Pro
305                 310                 315                 320

Leu Ala Gln Asn Lys Leu Glu Thr Leu Ser Gln Phe Glu Asp Trp Met
                 325                 330                 335

Asn Ser Tyr Lys Pro Glu Glu Leu Phe Asn Ala Asp Gly Ser Leu Lys
             340                 345                 350

Asp Glu Leu Lys Ala Ile Ala Pro Lys Gly Asp Lys Arg Met Ser Ala
         355                 360                 365

Asn Pro Ile Ala Asn Gly Gly Arg Arg Gly Glu Glu Ala Thr Asp
     370                 375                 380

Leu Thr Leu Pro Asp Trp Arg Gln Phe Thr Asn Asp Ile Thr Asn Glu
385                 390                 395                 400

Asn Arg Gly His Glu Leu Pro Lys Val Thr Gln Asn Met Asp Met Thr
                 405                 410                 415

Thr Leu Ser Asn Tyr Leu Glu Glu Val Ala Lys Leu Asn Pro Thr Ser
             420                 425                 430

Phe Arg Val Phe Gly Pro Asp Glu Thr Met Ser Asn Arg Leu Trp Ser
```

```
                435                 440                 445
Leu Phe Asn Thr Thr Asn Arg Gln Trp Met Glu Glu Val Lys Glu Pro
450                 455                 460

Asn Asp Gln Tyr Val Gly Pro Glu Gly Arg Ile Ile Asp Ser Gln Leu
465                 470                 475                 480

Ser Glu His Gln Ala Glu Gly Trp Leu Gly Tyr Thr Leu Thr Gly
                485                 490                 495

Arg Val Gly Ile Phe Ala Ser Tyr Glu Ser Phe Leu Arg Val Val Asp
                500                 505                 510

Thr Met Val Thr Gln His Phe Lys Trp Leu Arg His Ala Ser Glu Gln
                515                 520                 525

Ala Trp Arg Asn Asp Tyr Pro Ser Leu Asn Leu Ile Ala Thr Ser Thr
530                 535                 540

Ala Phe Gln Gln Asp His Asn Gly Tyr Thr His Gln Asp Pro Gly Met
545                 550                 555                 560

Leu Thr His Leu Ala Glu Lys Lys Ser Asn Phe Ile Arg Glu Tyr Leu
                565                 570                 575

Pro Ala Asp Gly Asn Ser Leu Leu Ala Val Gln Asp Arg Ala Phe Ser
                580                 585                 590

Glu Arg His Lys Val Asn Leu Ile Ile Ala Ser Lys Gln Pro Arg Gln
                595                 600                 605

Gln Trp Phe Thr Ala Asp Glu Ala Asp Glu Leu Ala Asn Glu Gly Leu
                610                 615                 620

Lys Ile Ile Asp Trp Ala Ser Thr Ala Pro Ser Gly Asp Val Asp Ile
625                 630                 635                 640

Thr Phe Ala Ser Ser Gly Thr Glu Pro Thr Ile Glu Thr Leu Ala Ala
                645                 650                 655

Leu Trp Leu Ile Asn Gln Ala Phe Pro Glu Val Lys Phe Arg Tyr Val
                660                 665                 670

Asn Val Val Glu Leu Leu Arg Leu Gln Lys Lys Ser Glu Ser His Met
                675                 680                 685

Asn Asp Glu Arg Glu Leu Ser Asp Ala Glu Phe Asn Lys Phe Phe Gln
690                 695                 700

Ala Asp Lys Pro Val Ile Phe Gly Phe His Ala Tyr Glu Asp Leu Ile
705                 710                 715                 720

Glu Ser Phe Phe Phe Glu Arg Lys Phe Lys Gly Asp Val Tyr Val His
                725                 730                 735

Gly Tyr Arg Glu Asp Gly Asp Ile Thr Thr Thr Tyr Asp Met Arg Val
                740                 745                 750

Tyr Ser Lys Leu Asp Arg Phe His Gln Ala Lys Glu Ala Ala Glu Ile
                755                 760                 765

Leu Ser Ala Asn Ser Thr Ile Asp Gln Ala Ala Asp Thr Phe Ile
770                 775                 780

Glu Lys Met Asp Ala Thr Leu Ala Lys His Phe Glu Val Thr Arg Asn
785                 790                 795                 800

Glu Gly Arg Asp Ile Glu Glu Phe Thr Asp Trp Asn Trp Ser Ala Leu
                805                 810                 815

Lys

<210> SEQ ID NO 18
<211> LENGTH: 794
<212> TYPE: PRT
<213> ORGANISM: Streptococcus gordonii
<220> FEATURE:
```

<223> OTHER INFORMATION: strain Challis / ATCC 35105 / CH1 / DL1 / V288

<400> SEQUENCE: 18

```
Met Thr Thr Asp Tyr Asn Ser Lys Ala Tyr Leu Glu Lys Val Asp Ala
  1               5                  10                  15
Trp Trp Arg Ala Ala Asn Tyr Ile Ser Ala Ala Gln Met Tyr Leu Lys
             20                  25                  30
Asp Asn Pro Leu Leu Lys Arg Asp Val Val Ala Asn Asp Leu Lys Ala
         35                  40                  45
His Pro Ile Gly His Trp Gly Thr Val Pro Gly Gln Asn Phe Ile Tyr
     50                  55                  60
Ala His Leu Asn Arg Thr Ile Asn Lys Tyr Asp Leu Asp Met Phe Tyr
 65                  70                  75                  80
Ile Glu Gly Pro Gly His Gly Gly Gln Val Met Val Ser Asn Ser Tyr
                 85                  90                  95
Leu Asp Gly Ser Tyr Thr Glu Leu Asn Pro Asn Ile Pro Gln Asn Glu
            100                 105                 110
Glu Gly Phe Lys His Leu Cys Lys Ile Phe Ser Phe Pro Gly Gly Ile
        115                 120                 125
Ala Ser His Ala Ala Pro Glu Thr Pro Gly Ser Ile His Glu Gly Gly
    130                 135                 140
Glu Leu Gly Tyr Ala Leu Ser His Ala Gly Ala Ile Leu Asp Asn
145                 150                 155                 160
Pro Asp Val Ile Ala Ala Thr Val Ile Gly Asp Gly Glu Gly Glu Thr
                165                 170                 175
Gly Pro Leu Met Ala Gly Trp Leu Ser Asn Thr Phe Ile Asn Pro Val
            180                 185                 190
Asn Asp Gly Ala Ile Leu Pro Ile Phe Tyr Leu Asn Gly Gly Lys Ile
        195                 200                 205
His Asn Pro Thr Ile Phe Glu Arg Lys Thr Asp Glu Glu Leu Thr Leu
    210                 215                 220
Phe Phe Glu Gly Leu Gly Trp Lys Pro Ile Phe Ala Asp Val Thr Ala
225                 230                 235                 240
Ile Ser Glu Asn His Glu Ala Ala His Ala Leu Phe Ala Ala Lys Leu
                245                 250                 255
Asp Glu Ala Ile Glu Glu Ile Lys Lys Val Gln Ala Glu Ala Arg Lys
            260                 265                 270
Gly Ser Ala Glu Glu Ala Thr Gln Ala Ile Phe Pro Val Leu Val Ala
        275                 280                 285
Arg Ile Pro Lys Gly Trp Thr Gly Pro Lys Ser Trp Glu Gly Thr Pro
    290                 295                 300
Ile Glu Gly Gly Phe Arg Ala His Gln Val Pro Ile Pro Val Asp Ala
305                 310                 315                 320
His His Met Glu His Val Asp Ala Leu Leu Asn Trp Leu Lys Ser Tyr
                325                 330                 335
Arg Pro Glu Glu Leu Phe Asp Glu Ser Gly Lys Val Leu Pro Glu Ile
            340                 345                 350
Ala Ala Ile Gly Pro Lys Gly Asp Arg Arg Met Ala Met Asn Pro Ile
        355                 360                 365
Thr Asn Ala Gly Val Ile Lys Pro Met Asp Thr Ala Asp Trp Lys Lys
    370                 375                 380
His Ala Leu Lys Phe Gly Thr Pro Gly Glu Ile Val Ala Gln Asp Met
385                 390                 395                 400
```

```
Ile Glu Phe Gly Lys Tyr Ala Thr Asp Leu Val Asp Ala Asn Pro Asp
                405                 410                 415

Asn Phe Arg Ile Phe Gly Pro Asp Glu Thr Lys Ser Asn Arg Leu Gln
            420                 425                 430

Glu Val Phe Thr Arg Thr Ser Arg Gln Trp Leu Gly Arg Met Arg Pro
        435                 440                 445

Glu Tyr Asp Glu Ala Leu Ser Pro Ala Gly Arg Val Ile Asp Ser Gln
    450                 455                 460

Leu Ser Glu His Gln Ala Glu Gly Met Leu Glu Gly Tyr Val Leu Thr
465                 470                 475                 480

Gly Arg His Gly Phe Phe Ala Ser Tyr Glu Ser Phe Leu Arg Val Val
                485                 490                 495

Asp Ser Met Val Thr Gln His Phe Lys Trp Leu Arg Lys Cys Lys Thr
            500                 505                 510

His Thr Thr Trp Arg Lys Asn Tyr Pro Ala Leu Asn Leu Ile Ala Thr
        515                 520                 525

Ser Thr Val Phe Gln Gln Asp His Asn Gly Tyr Thr His Gln Asp Pro
    530                 535                 540

Gly Ile Leu Thr His Leu Ala Glu Lys Thr Pro Glu Phe Ile Arg Glu
545                 550                 555                 560

Tyr Leu Pro Ala Asp Thr Asn Ser Leu Leu Ala Val Met Asp Lys Ala
                565                 570                 575

Phe Lys Ala Glu Asp Lys Val Asn Leu Ile Val Thr Ser Lys His Pro
            580                 585                 590

Arg Pro Gln Phe Tyr Ser Ala Glu Glu Ala Glu Leu Val Arg Glu
        595                 600                 605

Gly Tyr Lys Val Ile Asp Trp Ala Ser Thr Val Ser Asn Asn Glu Glu
    610                 615                 620

Pro Asp Val Val Phe Ala Ala Gly Thr Glu Pro Asn Leu Glu Ala
625                 630                 635                 640

Leu Ala Ala Val Ser Ile Leu His Lys Ala Phe Pro Glu Leu Lys Ile
                645                 650                 655

Arg Phe Val Asn Val Val Asp Ile Leu Lys Leu Arg His Pro Ser Val
            660                 665                 670

Asp Ala Arg Gly Leu Ser Asp Glu Glu Phe Asp Gln Val Phe Thr Thr
        675                 680                 685

Asp Lys Pro Val Ile Phe Ala Phe His Gly Tyr Glu Gly Met Ile Arg
    690                 695                 700

Asp Ile Phe Phe Asn Arg His Asn His Asn Leu Arg Val His Gly Tyr
705                 710                 715                 720

Arg Glu Asn Gly Asp Ile Thr Thr Pro Phe Asp Met Arg Val Met Ser
                725                 730                 735

Glu Leu Asp Arg Phe His Leu Ala Gln Asp Ala Ala Asn Ala Ala Leu
            740                 745                 750

Gly Glu Asp Ala Ala Val Phe Ser Ala Lys Met Asp Glu Thr Val Ala
        755                 760                 765

Tyr His Asn Ala Tyr Ile Arg Glu Asn Gly Asp Asp Ile Pro Glu Val
    770                 775                 780

Gln Asn Trp Lys Trp Glu Asn Ile Asn Lys
785                 790

<210> SEQ ID NO 19
<211> LENGTH: 812
<212> TYPE: PRT
```

<213> ORGANISM: Thiobacillus denitrificans
<220> FEATURE:
<223> OTHER INFORMATION: strain ATCC 25259

<400> SEQUENCE: 19

| | | | | | | | | | | | | | | |
|---|---|---|---|---|---|---|---|---|---|---|---|---|---|---|
|Met|Tyr|Ser|Phe|Glu|Pro|Tyr|Thr|Gly|Arg|Pro|Ile|Arg|Leu|Asp|Leu|
|1| | | |5| | | | |10| | | | |15| |

| | | | | | | | | | | | | | | |
|---|---|---|---|---|---|---|---|---|---|---|---|---|---|---|
|Leu|Val|His|Lys|Gly|Glu|Thr|Ser|Met|Asp|Ala|Pro|Thr|Pro|Ala|Thr|
| | | |20| | | | |25| | | | |30| | |

Ala Leu Thr Ser Val Glu Leu Glu Gln Leu Asp Ala Tyr Trp Arg Ala
                35                  40                  45

Ala Asn Tyr Leu Ser Val Gly Gln Ile Tyr Leu Phe Asp Asn Pro Leu
         50                  55                  60

Leu Lys Gln Pro Leu Asp Arg Ala His Ile Lys Pro Arg Leu Leu Gly
65                  70                  75                  80

His Trp Gly Thr Thr Pro Gly Leu Asn Phe Ile Tyr Ala His Met Asn
             85                  90                  95

Arg Ala Ile Arg Ala His Asp Leu Asp Met Ile Phe Ile Thr Gly Pro
             100                 105                 110

Gly His Gly Gly Pro Ala Val Val Ala Asn Thr Tyr Leu Glu Gly Ser
         115                 120                 125

Tyr Ser Glu Leu Tyr Pro Asn Ile Thr Arg Asp Glu Ala Gly Leu Arg
    130                 135                 140

Gln Leu Phe Arg Gln Phe Ser Phe Pro Gly Gly Ile Pro Ser His Ala
145                 150                 155                 160

Ala Pro Glu Thr Pro Gly Ser Ile Asn Glu Gly Gly Glu Leu Gly Tyr
             165                 170                 175

Ser Leu Leu His Ala Tyr Gly Ala Val Phe Asp Asn Pro Asp Leu Ile
         180                 185                 190

Ala Cys Cys Val Ile Gly Asp Gly Glu Ala Glu Thr Gly Ala Leu Ala
    195                 200                 205

Thr Ser Trp His Ser Asn Lys Phe Leu Asp Pro Arg Gly Asp Gly Ala
             210                 215                 220

Val Leu Pro Val Leu His Leu Asn Gly Tyr Lys Ile Ala Asn Pro Ala
225                 230                 235                 240

Phe Leu Ala Arg Ile Pro Arg His Glu Leu Glu Ser Leu Leu Thr Gly
             245                 250                 255

Tyr Gly Tyr Arg Pro Ile Phe Val Glu Gly Asp Glu Pro Ser Asp Met
         260                 265                 270

His Gln Lys Met Ala Ala Ala Val Asp Gln Ala Leu Ala Glu Ile Arg
    275                 280                 285

Gly Ile Gln Arg Arg Ala Arg Asp Gly Gly Glu Thr Thr Arg Pro Thr
290                 295                 300

Trp Pro Met Ile Val Leu Asp Ser Pro Lys Gly Trp Thr Gly Pro Lys
305                 310                 315                 320

Glu Val Asp Gly Lys Lys Thr Glu Asp Tyr Trp Arg Ser His Gln Val
             325                 330                 335

Pro Phe Gly Asp Leu Asp Asn Pro Ala His Val Arg Leu Leu Asp Asp
         340                 345                 350

Trp Met Arg Ser Tyr Arg Pro Glu Glu Leu Phe Asp Ala Gly Gly Ala
    355                 360                 365

Leu Lys Pro Glu Leu Ala Ala Leu Ala Pro Thr Gly Glu Arg Arg Met
370                 375                 380

Gly Ala Asn Pro His Ala Asn Gly Gly Lys Leu Leu Arg Asp Leu Arg

```
            385                 390                 395                 400
Leu Pro Asp Phe Arg Asp Tyr Arg Val Glu Leu Asp Ala Pro Gly Ser
                    405                 410                 415

Val Val Ser Glu Thr Thr Arg Thr Leu Gly Ala Tyr Leu Arg Asp Val
            420                 425                 430

Val Arg Asp Asn Pro Asp Asn Phe Arg Leu Phe Gly Pro Asp Glu Thr
                435                 440                 445

His Ser Asn Arg Leu Ser Ala Val Phe Glu Val Thr Asp Arg Thr Trp
        450                 455                 460

Val Ala Glu Arg Tyr Pro Tyr Asp Asp His Leu Ala Ala Asp Gly Arg
465                 470                 475                 480

Val Met Glu Ile Leu Ser Glu His Ala Cys Glu Gly Trp Leu Glu Gly
                    485                 490                 495

Tyr Leu Leu Ser Gly Arg His Gly Leu Phe Ser Cys Tyr Glu Ala Phe
                500                 505                 510

Ile His Ile Ile Gly Ser Met Phe Asn Gln His Ala Lys Trp Leu Lys
            515                 520                 525

Val Cys Asn Glu Ile Pro Trp Arg Val Pro Val Ala Ser Leu Asn Ile
        530                 535                 540

Leu Leu Thr Ser His Val Trp Arg Gln Asp His Asn Gly Phe Ser His
545                 550                 555                 560

Gln Asp Pro Gly Phe Ile Asp His Val Val Asn Lys Lys Ala Asp Val
                    565                 570                 575

Ile Arg Val Tyr Leu Pro Pro Asp Ala Asn Thr Leu Leu Val Val Ala
                580                 585                 590

Asp Lys Cys Leu Arg Ser Arg Asn Leu Val Asn Val Ile Val Ala Gly
            595                 600                 605

Lys Gln Pro Glu Gln Gln Trp Leu Asp Met Asp Ala Ala Val Thr His
        610                 615                 620

Ala Gly Val Gly Val Gly Ile Trp Asp Trp Ala Cys Asn Asp Gln Gly
625                 630                 635                 640

Gly Glu Pro Asp Ile Val Leu Ala Ala Ala Gly Asp Val Pro Thr Met
                    645                 650                 655

Glu Met Leu Ala Ala Ile Asp Leu Leu Arg Thr Leu Val Pro Asp Leu
                660                 665                 670

Lys Ile Arg Phe Ile Asn Val Val Asp Leu Met Thr Leu Gln Pro Ala
            675                 680                 685

Glu Glu His Pro His Gly Leu Pro Asp Glu Glu Phe Asp Leu Leu Phe
        690                 695                 700

Thr Thr Asp Lys Pro Ile Leu Phe Gly Tyr His Gly Tyr Pro Trp Leu
705                 710                 715                 720

Ile His Arg Leu Thr Tyr Arg Arg Thr Asn His Asp Asn Leu His Val
                    725                 730                 735

Arg Gly Tyr Lys Glu Glu Gly Thr Thr Thr Pro Phe Asp Met Val
                740                 745                 750

Val Leu Asn Glu Leu Asp Arg Phe His Leu Val Ile Asp Val Ala Arg
            755                 760                 765

Arg Val Pro Lys Leu Gln Ala Gln Ala Ala His Leu Gln Gln Gln Met
        770                 775                 780

Leu Asp Lys Leu Gly Ala His Thr Gln Tyr Ile His Ala His Gly Glu
785                 790                 795                 800

Asp Met Pro Glu Ile Arg Asp Trp Lys Trp Ala Arg
                    805                 810
```

<210> SEQ ID NO 20
<211> LENGTH: 799
<212> TYPE: PRT
<213> ORGANISM: Lactobacillus crispatus
<220> FEATURE:
<223> OTHER INFORMATION: strain ST1

<400> SEQUENCE: 20

```
Met Ala Val Asp Tyr Asp Ser Lys Asp Tyr Leu Lys Ser Val Asp Ala
1               5                   10                  15

Tyr Trp Arg Ala Ala Asn Tyr Leu Ser Val Gly Gln Leu Phe Leu Met
            20                  25                  30

Lys Asn Pro Leu Leu Lys Thr Pro Leu Val Ala Glu Asp Val Lys Pro
        35                  40                  45

Lys Pro Ile Gly His Trp Gly Thr Ile Ala Pro Gln Asn Phe Ile Tyr
    50                  55                  60

Ala His Leu Asn Arg Val Leu Lys Lys Tyr Asp Leu Asn Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Thr Glu Arg Tyr Pro Glu Ile Thr Gln Asp Glu
            100                 105                 110

Lys Gly Met Ala Lys Leu Phe Lys Arg Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Leu Ser His Gly Thr Gly Ala Val Leu Asp Asn
145                 150                 155                 160

Pro Asp Val Ile Ala Ala Val Glu Ile Gly Asp Gly Glu Ala Glu Thr
                165                 170                 175

Gly Pro Leu Ala Ala Ser Trp Phe Ser Asp Lys Phe Ile Asn Pro Ile
            180                 185                 190

Lys Asp Gly Ala Val Leu Pro Ile Leu Gln Ile Asn Gly Phe Lys Ile
        195                 200                 205

Ser Asn Pro Thr Ile Val Ser Arg Met Ser Asp Gln Glu Leu Thr Glu
    210                 215                 220

Tyr Phe Arg Gly Met Gly Trp Asp Pro His Phe Val Ser Val Phe Lys
225                 230                 235                 240

Gly Gly Arg Phe Asp Gly Glu Lys Asp Pro Met Gln Val His Glu Glu
                245                 250                 255

Met Ala Lys Thr Met Asp Glu Val Ile Glu Glu Ile Lys Ala Ile Gln
            260                 265                 270

Lys His Ala Arg Glu Asn Asn Asp Ala Thr Leu Pro His Trp Pro Met
        275                 280                 285

Ile Ile Phe Gln Cys Pro Lys Gly Trp Thr Gly Pro Lys Lys Asp Leu
    290                 295                 300

Asp Gly Asn Pro Ile Glu Asn Ser Phe Arg Ala His Gln Ile Pro Ile
305                 310                 315                 320

Pro Val Ala Gln Gly Asp Met Glu His Ala Asp Met Leu Thr Asp Trp
                325                 330                 335

Leu Glu Ser Tyr Lys Pro Glu Glu Leu Phe Asn Glu Asp Gly Ser Pro
            340                 345                 350

Lys Glu Ile Val Thr Glu Asn Thr Ala Lys Gly Asp His Arg Met Ala
        355                 360                 365
```

```
Met Asn Pro Ile Thr Asn Gly Gly Ile Asp Pro Lys Arg Leu Asn Leu
    370                 375                 380
Pro Asp Tyr Arg Lys Phe Ala Leu Lys Phe Asp Lys Pro Gly Ser Val
385                 390                 395                 400
Glu Ala Gln Asp Met Val Glu Trp Ala Lys Tyr Leu Asp Glu Val Ala
                405                 410                 415
Lys Leu Asn Pro Thr Thr Phe Arg Gly Phe Gly Pro Asp Glu Ser Lys
                420                 425                 430
Ser Asn Arg Leu Phe Gln Leu Leu Asp Asp Gln Lys Arg Gln Trp Glu
            435                 440                 445
Pro Glu Val His Glu Pro Asn Asp Glu Asn Leu Ala Pro Ser Gly Arg
450                 455                 460
Val Ile Asp Ser Gln Leu Ser Glu His Gln Asp Glu Gly Phe Leu Glu
465                 470                 475                 480
Gly Tyr Val Leu Thr Gly Arg His Gly Phe Phe Ala Thr Tyr Glu Ala
                485                 490                 495
Phe Gly Arg Val Val Asp Ser Met Leu Thr Gln His Met Lys Trp Leu
                500                 505                 510
Arg Lys Ala Lys Glu Gln Tyr Trp Arg His Asp Tyr Pro Ser Leu Asn
            515                 520                 525
Phe Val Ala Thr Ser Thr Val Phe Gln Gln Asp His Asn Gly Tyr Thr
530                 535                 540
His Gln Asp Pro Gly Ile Leu Thr His Leu Tyr Glu Lys Asn Arg Pro
545                 550                 555                 560
Asp Leu Val His Glu Tyr Leu Pro Ser Asp Thr Asn Thr Leu Leu Ala
                565                 570                 575
Val Gly Asp Lys Ala Leu Gln Asp Arg Glu Cys Ile Asn Val Leu Val
                580                 585                 590
Thr Ser Lys Gln Pro Arg Pro Gln Trp Phe Ser Ile Glu Glu Ala Lys
            595                 600                 605
Lys Leu Val Asp Lys Gly Leu Gly Tyr Ile Asp Trp Ala Ser Thr Asp
610                 615                 620
Lys Gly Ala Lys Pro Asp Val Val Phe Ala Ser Thr Glu Thr Glu Pro
625                 630                 635                 640
Thr Ile Glu Thr Leu Ala Ala Ile Asp Ile Leu His Lys Lys Phe Pro
                645                 650                 655
Asp Leu Lys Ile Arg Tyr Ile Asn Val Val Asp Val Met Lys Leu Met
                660                 665                 670
Asp Pro Lys Asp Asn Lys Asn Gly Leu Ser Thr Glu Glu Phe Asp Arg
            675                 680                 685
Leu Phe Pro Lys Asp Val Pro Val Ile Phe Ala Trp His Gly Tyr Lys
690                 695                 700
Ser Met Met Glu Ser Ile Trp Phe Ala Arg Lys Arg Tyr Asn Val His
705                 710                 715                 720
Ile His Cys Tyr Glu Glu Asn Gly Asp Ile Thr Thr Pro Phe Asp Met
                725                 730                 735
Arg Val Leu Asn His Leu Asp Arg Phe Asp Leu Ala Lys Asp Ala Val
                740                 745                 750
Glu Ser Ile Asp Lys Leu Lys Gly Lys Asn Ala Asp Phe Ile Ser His
            755                 760                 765
Met Asp Asp Leu Leu Glu Lys His His Gln Tyr Ile Arg Asp Asn Gly
770                 775                 780
```

```
Lys Asp Met Pro Glu Val Thr Glu Trp Gln Trp Ser Gly Leu Lys
785                 790                 795
```

ENZYMATIC PRODUCTION OF AN ACYL PHOSPHATE FROM A 2-HYDROXYALDEHYDE

CROSS-REFERENCE TO RELATED APPLICATIONS

This application is a § 371 National Stage Application of PCT/EP2016/071150 filed on Sep. 8, 2016, which claims priority to EP 15184678.9 filed on Sep. 10, 2015 and EP 16157821.6 filed on Feb. 29, 2016. All of these documents are hereby incorporated by reference in their entirety.

The present invention relates to a method for the enzymatic production of an acyl phosphate from a 2-hydroxyaldehyde said method making use of a phosphoketolase or of a sulfoacetaldehyde acetyltransferase, as well as to the use of a phosphoketolase or of a sulfoacetaldehyde acetyltransferase or of a microorganism expressing a phosphoketolase or a sulfoacetaldehyde acetyltransferase for the production of an acyl phosphate from a 2-hydroxyaldehyde.

For the past several decades, practitioners of metabolic engineering have endeavoured to explore biological solutions for the production of chemicals, thus, providing alternatives to more traditional chemical processes. In general, biological solutions allow for the utilization of renewable feedstocks (e.g. sugars) and compete with existing petrochemical based processes. A multi-step, biological solution for the production of a chemical typically comprises a microorganism as the catalyst for the conversion of feedstock to a target molecule. A complete set of enzyme reactions for the production of a particular target molecule can be grouped into those belonging to central carbon pathways and those belonging to the product specific pathway. The reactions belonging to central carbon and product specific pathways are linked in that redox (typically, NAD(P)H) and energetic (typically, ATP) constraints of every enzyme reaction must be accounted for in an overall balance contributing to the competitiveness of the process. Historically, central carbon pathways of heterotrophs growing on sugars have been described as the Embden-Meyerhoff-Parnas pathway (EMPP; i.e., "glycolysis"), the pentose phosphate pathway (PPP), the Entner-Doudoroff pathway (EDP), and the phosphoketolase pathway (PKP) (see Gottschalk (1986), Bacterial Metabolism, $2^{nd}$ Edition, Springer-Verlag, New York). Each central pathway or combinations of central pathways offer advantages and disadvantages with respect to a specific target molecule. In order to provide competitive bioprocesses, recombinant microorganisms with modifications involving the EMPP, PPP and EDP have been described (M. Emmerling et al., Metab. Eng. 1:117 (1999); L. O. Ingram et al., Appl. Environ. Microbiol. 53: 2420 (1987); C. T. Trinh et al., Appl. Environ. Microbiol. 74:3634 (2008)). More recently, recombinant microorganisms with modifications involving the PKP have been described (see Sonderegger et al. Appl. Environ. Microbiol. 70 (2004), 2892-2897, U.S. Pat. No. 7,253,001, Chinen et al. J. Biosci. Bioeng. 103 (2007), 262-269, U.S. Pat. No. 7,785,858; Fleige et al., Appl. Microbiol. Cell Physiol. 91 (2011), 769-776).

The EMPP (glycolysis) converts 1 mol glucose to 2 mol pyruvate (PYR). When acetyl-CoA is desired, 1 mol PYR can be converted to 1 mol of acetyl-CoA (AcCoA) with the concomitant generation of 1 mol $CO_2$ and 1 mol NADH. The sum of the reactions is given in Equation 1.

(Equation 1)

The PPP provides a means to convert 1 mol glucose to 1 mol $CO_2$ and 2 mol NADPH, with the concomitant generation of 0.67 mol fructose-6-phosphate (F6P) and 0.33 mol glyceraldehyde-3-phosphate (GAP). The F6P and GAP thus formed must be metabolized by other reaction pathways, e.g. by the EMPP. The EDP converts 1 mol glucose to 1 mol GAP and 1 mol PYR with the concomitant generation of 1 mol NADPH. As with the PPP, the GAP thus formed must be metabolized by other reaction pathways. The PKP provides a means to convert 1 mol glucose to 1 mol GAP and 1.5 mol acetyl phosphate (AcP). When acetyl-CoA is desired, 1 equivalent of AcP plus 1 equivalent coenzyme A (CoA) can be converted to 1 equivalent acetyl-CoA and 1 equivalent inorganic phosphate (Pi) by the action of phosphotransacetylase.

In view of the increasing demand for processes which make use of renewable resources for producing all sorts of compounds, it is desirable to provide means and methods which allow for an efficient production of central metabolites, such as acyl-CoA or carboxylic acids, or their precursors, thereby building a platform for developing further processes to convert these metabolites into useful compounds.

Thus, there is a need to provide methods, comprising central carbon and product specific pathways, that maximize the conversion of feedstock to product by best accommodating the redox and energetic constraints of enzyme reactions, thereby allowing the energetically efficient production of precursors of acyl-CoA or carboxylic acid, in particular of microorganisms which can be used for the production of numerous industrially important compounds from renewable resources, such as organic acids, alkenes, dienes or short chain carboxylic acids. Applicants have addressed this need by providing the embodiments as defined in the claims.

Thus, the present invention relates to method for the enzymatic production of an acyl phosphate from a 2-hydroxyaldehyde and phosphate in which the production of an acyl phosphate from a 2-hydroxyaldehyde and phosphate is achieved by the use of a phosphoketolase or of a sulfoacetaldehyde acetyltransferase (EC 2.3.3.15) according to the following reaction scheme:

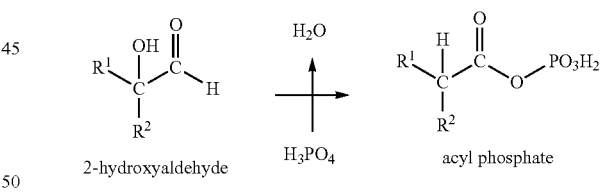

wherein $R^1$ and $R^2$ are selected independently from H, $CH_3$, $CH_2OH$ and $C_2H_5$ and wherein if $R^1$ is H, $R^2$ cannot be H.

The term "wherein if $R^1$ is H, $R^2$ cannot be H" as used in the context of the present invention means that $R^1$ and $R^2$ cannot be H at the same time, i.e. it also means that if $R^2$ is H, $R^1$ cannot be H.

The present application describes that enzymes which are classified as phosphoketolases or as sulfoacetaldehyde acetyltransferases (EC 2.3.3.15) are capable of catalyzing the formation of an acyl phosphate from a 2-hydroxyaldehyde as defined above and phosphate.

Different types of phosphoketolases are known and all of them can be employed in the method according to the invention. Generally, phosphoketolases are classified into two types based on substrate preference as regards their naturally catalyzed reaction: xylulose-5-phosphate (X5P)

phosphoketolases, which are classified in EC 4.1.2.9 and which naturally use X5P and fructose-6-phosphate (F6P) as a substrate but which prefer X5P, and X5P/fructose-6-phosphate (F6P) phosphoketolases, which are classified in 4.1.2.22 and which can use both X5P and F6P with comparable activities as substrate (Suzuki et al., J. Biol. Chem. 44 (2010), 34279-34287). In the following, the term "phosphoketolase" always refers to both types.

Thus, X5P phosphoketolases are enzymes which are classified in EC 4.1.2.9 and which are capable of catalyzing the following reaction:

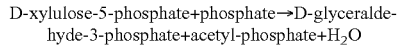

The other type of phosphoketolases which are classified in EC 4.1.2.22 are generally referred to as fructose-6-phosphate phosphoketolases and are naturally capable of catalyzing the following reaction:

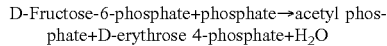

There are also cases in which a phosphoketolase is assigned to both types of phosphoketolases, e.g., in the case of the phosphoketolase from *Nitrolancetus hollandicus* Lb, or where an identified phosphoketolase has not yet been assigned to any of the two types but is simply generally classified as a phosphoketolases. The term "phosphoketolase" when used herein also refers to all these phosphoketolases.

Thus, in one embodiment of the method according to the present invention the enzymatic conversion of a 2-hydroxyaldehyde and phosphate into an acyl phosphate according to the above shown reaction scheme is achieved by making use of a phosphoketolase which is classified as a phosphoketolases in EC 4.1.2.9. This enzyme has been identified in a variety of organisms, in particular microorganisms such as bacteria and fungi. In one preferred embodiment the phosphoketolase (EC 4.1.2.9) originates from a prokaryotic organism, preferably a bacterium. The enzyme has, for example, been described to occur in *Lactococcus lactis*, *Lactobacillus plantarum* (Uniprot Accession numbers: Q88S87; Q88U67), *Lactobacillus pentosus* (Uniprot Accession number: Q937F6), *Lactobacillus reuteri*, *Bifidobacterium animalis* (Uniprot Accession number: A0PAD9), *Bifidobacterium animalis* subsp. *lactis* (Uniprot Accession number: Q9AEM9), *Butyrovibrio fibrisolvens*, *Fibrobacter intestinalis*, *Fibrobacter succinogenes*, *Leuconostoc mesenteroides*, *Oenococcus oeni*, *Starkeya novella*, *Thiobacillus* sp., *Thermobispora bispora* (strain ATCC 19993/DSM 43833/CBS 139.67/JCM 10125/NBRC 14880/R51; Uniprot Accession number D6YAD9), *Thermobaculum terrenum* (strain ATCC BAA-798/YNP1; Uniprot Accession number D1CI63) and *Nitrolancetus hollandicus* Lb (Uniprot Accession number I4EJ52).

In another preferred embodiment the phosphoketolase (EC 4.1.2.9) originates from a eukaryotic organism, preferably a fungus, e.g. a yeast, such as *S. cerevisiae*. The enzyme has, for example, been described to occur in *Emericella nidulans* (Uniprot Accession number: Q5B3G7), *Metarhizium anisopliae* (Uniprot Accession number: C1K2N2), *Candida boidinii*, *Candida curvata*, *Candida famata*, *Candida humicola*, *Candida parapsilosis*, *Candida parapsilosis* NCYC 926, *Candida tropicalis*, *Cyberlindnera jadinii*, *Cyberlindnera saturnus*, *Debaromyces robertsiae*, *Fusarium oxysporum*, *Kluyveromyces marxianus*, *Kluyveromyces phaseolosporus*, *Lipomyces starkeyi*, *Ogataea angusta*, *Pachysolen tannophilus*, *Priceomyces medius*, *Saccharomyces cerevisiae*, *Rhodospiridium toruloides*, *Rhodotorula glutinis*, *Rhodotorula graminis*, *Penicillium chrysogenum*, *Trichosporon cutaneum* and *Yarrowia lipolytica*.

The enzymatic activity of a phosphoketolase (EC 4.1.2.9) can be assessed with methods known to a person skilled in the art. Such methods are, e.g., described in Meile et al. (J. Bacteriol. 183 (2001), 2929-2936) and in Suzuki et al (Acta Cryst. F66 (2010), 941-943).

The phosphoketolase (EC 4.1.2.9) is structurally and functionally well defined. For example, Petrareanu et al. (Acta Crystallographica F66 (2010), 805-807) describe the X-ray crystallographic analysis of the xylulose-5-phosphate phosphoketolase from *Lactococcus lactis*.

In another embodiment of the method according to the present invention the enzymatic conversion of a 2-hydroxyaldehyde and phosphate into an acyl phosphate according to the above shown reaction scheme is achieved by making use of a phosphoketolase which is classified as a fructose-6-phosphate phosphoketolase in EC 4.1.2.22. This enzyme has been identified in a variety of organisms, in particular microorganisms such as bacteria and fungi. In one preferred embodiment the fructose-6-phosphate phosphoketolase (EC 4.1.2.22) originates from a prokaryotic organism, preferably a bacterium. The enzyme has, for example, been described to occur in *Bifidobacterium adolescentis*, *Bifidobacterium animalis* subsp. *lactis* (Uniprot Accession number: Q9AEM9), *Bifidobacterium longum*, *Bifidobacterium pseudolongum*, in particular *Bifidobacterium pseudolongum* subsp. *globosum*, *Bifidobacterium bifidum*, *Bifidobacterium breve*, *Bifidobacterium dentium*, *Bifidobacterium mongoliense*, *Bifidobacterium bombi*, *Cupriavidus necator*, *Gardnerella vaginalis*, *Gluconacetobacter xylinus*, *Lactococcus crispatus*, *Lactobacillus paraplantarum*, *Leuconostoc mesenteroides* and *Nitrolancetus hollandicus* Lb (Uniprot Accession number I4EJ52).

In another preferred embodiment the fructose-6-phosphate phosphoketolase (EC 4.1.2.22) originates from a eukaryotic organism, preferably a fungus, e.g. a yeast, such as *S. pastorianus*. The enzyme has, for example, been described to occur in *Candida* sp., *Candida* sp. 107, *Candida tropicalis*, *Rhodotorula glutinis*, *Rhodotorula graminis* and *Saccharomyces pastorianus*.

The enzyme is structurally and functionally well defined. For example, Suzuki et al. (Acta Crystallographica F66 (2010), 941-943; J. Biol. Chem. 285 (2010), 34279-34287) describe the overexpression, crystallization and X-ray analysis of the phosphoketolase from *Bifidobacterium breve*. The gene encoding the xylulose-5-phosphate/fructose-6-phosphate phosphoketolase from *Bidifobacterium lactis* is e.g. described in Meile et al. (J. Bacteriol. 183 (2001), 2929-2936).

The enzymatic activity of a fructose-6-phosphate phosphoketolase (EC 4.1.2.22) can be assessed with methods known to a person skilled in the art. Such methods are, e.g., described in Meile et al. (J. Bacteriol. 183 (2001), 2929-2936) and in Suzuki et al. (Acta Cryst. F66 (2010), 941-943).

Other phosphoketolases which have not yet been classified into EC 4.2.1.9 or EC 4.2.1.22 and which can be used in the method according to the present invention are, e.g. the phosphoketolase from *Thermosynechococcus elongatus* (strain BP-1; Uniprot Accession number: Q8DJN6), the phosphoketolase from *Bacillus coagulans* 36D1 (Uniprot Accession number: G2TIL0), the phosphoketolase from *Lactococcus lactis* subsp. *lactis* (Strain KF147; Uniprot Accession number: A9QST6), the phosphoketolase from *Bifidobacterium pseudolongum* subsp. *globosum* (Uniprot Accession number: Q6R2Q6) and the phosphoketolase from *Clostridium acetobutylicum* (Strain ATCC 824; Uniprot Accession number: Q97JE3; Servisky et al. (J. Ind. Microbiol. Biotechnol. 39 (2012), 1859-1867); SEQ ID NO: 2).

In the appended Examples it is shown that 2,3-hydroxypropanal (D,L-glyceraldehyde) and 2-hydroxypropanal (D,L-lactaldehyde) can be converted by phosphoketolase into 3-hydroxypropionyl phosphate and propionyl phosphate, respectively, which can then be further converted into 3-hydroxypropionic acid and propionic acid, respectively, by spontaneous hydrolyzation.

In one embodiment the phosphoketolase employed in a method according to the present invention is a phosphoketolase from *Bifidobacterium pseudolongum* subsp. *globosum* (Uniprot Accession number: Q6R2Q6; SEQ ID NO: 1) or a phosphoketolase from *Clostridium acetobutylicum* (Strain ATCC 824; Uniprot Accession number: Q97JE3; SEQ ID NO: 2) or a phosphoketolase from *Lactococcus lactis* subsp. *lactis* (Strain KF147; Uniprot Accession number: A9QST6; SEQ ID NO: 3) or a phosphoketolase from *Lactococcus crispatus* (Uniprot Accession number: D5H215; SEQ ID NO: 20) or a phosphoketolase from *Bifidobacterium gallicum* (DSM 20093; Uniprot Accession number: D1NS90; SEQ ID NO: 16) or a phosphoketolase from *Leuconostoc citreum* (strain KM20; Uniprot Accession number: B1MWV8; SEQ ID NO: 17) or a phosphoketolase from *Streptococcus gordonii* (strain Challis/ATCC 35105/CH1/DL1/V288; Uniprot Accession number: A8AV21; SEQ ID NO: 18) or a phosphoketolase from *Thiobacillus denitrificans* (strain ATCC 25259; Uniprot Accession number: Q3SKJ7; SEQ ID NO: 19).

In a preferred embodiment, the phosphoketolase employed in the method of the invention has an amino acid sequence as shown in any one of SEQ ID NOs: 1 to 3 or 16 to 20 or shows an amino acid sequence which is at least x % homologous to any one of SEQ ID NOs: 1 to 3 or 16 to 20 and is a phosphoketolase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting a 2-hydroxyaldehyde and phosphate into an acyl phosphate as set forth herein above. Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

It has been described that a multiple alignment of phosphoketolase sequences shows several highly conserved regions and two of these regions are used as signature patterns for phosphoketolases (http://prosite.expasy.org/PDOC60002). The first signature pattern is E-G-G-E-L-G-Y and the second signature pattern is G-x(3)-[DN]-x-P-x(2)-[LIVFT]-x(3)-[LIVM]-x-G-D-G-E. The function of the first signature pattern is not yet known while the second signature pattern corresponds to the thiamine pyrophosphate binding site. Thus, in a preferred embodiment, a phosphoketolase as defined herein above has an amino acid sequence which contains at least one of the two above mentioned signature patterns, preferably at least the second signature pattern, and even more preferably both signature patterns.

Sequence comparisons show that the overall sequence identity between phosphoketolases from different origins can be as low as around 26%. For example, Meile et al. (J. Biol. Chem. 183 (2001), 2929-2936) reports that the D-xylulose 5-phosphate/D-fructose 6-phosphate phosphoketolase gene (xfp) of *Bifidobacterium lactis* revealed identities of 26% to 55% to sequences in the genomes of other organisms.

Whether a chosen phosphoketolase is capable of catalyzing the conversion of a 2-hydroxyaldehyde and phosphate into acyl phosphate and $H_2O$ can, e.g., be assessed by an assay as set forth in the appended Examples.

The term "phosphate" as used in connection with the method of the invention refers to a compound which is acceptable as a phosphate source for the enzyme employed in the method for the conversion of a 2-hydroxyaldehyde and phosphate into an acyl phosphate and $H_2O$. One possibility is the provision of phosphate in the form of phosphoric acid, i.e. $H_3PO_4$. However, also other forms are conceivable, in particular salts of phosphoric acid ($H_3PO_4$) in which one, two or three of the hydrogen atoms are replaced by other ions, such as sodium ions. Phosphoketolases are thiamine diphosphate-dependent enzymes, i.e. they require thiamine diphosphate (also referred to as ThDP or TPP) as a cofactor. Therefore, it is advantageous that in a method according to the invention, when a phosphoketolase is employed, TPP is provided during the reaction. Moreover, some phosphoketolases require ions, such as $Mg^{2+}$ or $Ca^{2+}$ as cofactors. In such a case, the method according to the invention also includes the presence of such ions during the conversion as described above.

The enzymatic conversion of a 2-hydroxyaldehyde and phosphate into an acyl phosphate according to the above shown reaction scheme can also be achieved by making use of a sulfoacetaldehyde acetyltransferase (EC 2.3.3.15). Sulfoacetaldehyde acetyltransferases (EC 2.3.3.15) are enzymes which can catalyze the following reaction:

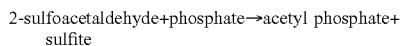

2-sulfoacetaldehyde+phosphate→acetyl phosphate+sulfite

The enzyme has been identified in a variety of organisms, in particular bacteria. In one preferred embodiment the sulfoacetaldehyde acetyltransferase (EC 2.3.3.15) originates from a prokaryotic organism, preferably a bacterium. The enzyme has, for example, been described to occur in *Castellaniella defragrans* (Uniprot Accession number: Q84H44; previously *Alcaligenes defragans* (Ruff et al., Biochem. J. 369 (2003), 275-285)), *Alcaligenes xylosoxidans xylosoxidans* (Uniprot Accession number: Q84H41), *Desulfonispora thiosulfatigenes* (Uniprot Accession number: Q93PS3), *Rhizobium meliloti* (strain 1021) (Uniprot Accession number: Q92UW6), *Ruegeria pomeroyi* (Uniprot Accession number: Q5LMK2), *Cupriavidus necator* (Uniprot Accession number: Q0K022), *Roseovarius nubinhibens* (Uniprot Accession number: A3SR25), *Acinetobacter* sp. and *Pseudomonas aeruginosa*.

In principle any sulfoacetaldehyde acetyltransferase (EC 2.3.3.15) can be employed in the conversion of a 2-hydroxyaldehyde and phosphate into an acyl phosphate according to a method of the invention.

Sulfoacetaldehyde acetyltransferases are, like phosphoketolases, thiamine pyrophosphate (TPP)-dependent enzymes and therefore are characterized in that they contain a TPP binding domain. Among the sulfoacetaldehyde acetyltransferases known, the TPP binding domain is highly conserved (see, e.g., Ruff et al., Biochem. J. 369 (2003), 275-285). Overall, the known sulfoacetaldehyde acetyltransferases show a high degree of sequence conservation near the N-terminus, including the TPP binding domain (see Ruff et al., loc. cit.). Sequence divergence can be observed in the N-terminus of the enzymes itself and in a region near amino acid 400 of the *C. defragrans* enzyme. Ruff et al. (loc. cit.) describe that sulfoacetaldehyde acetyltransferases form 3 subgroups (see FIG. 4 of said publication). Subgroups 2 and 3 are said to show a TPP binding domain conforming with the PROSITE consensus sequence (L/I/V/M/F)(G/S/A)X$_5$PX$_4$(L/I/V/M/F/Y/W)X(L/I/V/M/F)XGD(G/S/A)(G/S/A/C), while subgroup slightly deviates from the consensus sequence:

(L/I/V/M/F)(G/S/A)X$_5$PX$_4$(L/I/V/M/F/Y/W)X(L/I/V/M/F/Y)XGD(G/S/A)(G/S/A/C).

Apart from these regions, the sequence identity between the different sulfoacetaldehyde acetyltransferases can be rather low (down to about 44%).

In a preferred embodiment, the sulfoacetaldehyde acetyltransferase employed in a method according to the present invention is the sulfoacetaldehyde acetyltransferase of *C. defragrans* showing the amino acid sequence as depicted in SEQ ID NO:4 or the sulfoacetaldehyde acetyltransferase of *Alcaligenes xylosoxidans xylosoxidans* showing the amino acid sequence as depicted in SEQ ID NO:5 or the sulfoacetaldehyde acetyltransferase of *Desulfonispora thiosulfatigenes* showing the amino acid sequence as depicted in SEQ ID NO:6 or the sulfoacetaldehyde acetyltransferase of *Rhizobium meliloti* (strain 1021) showing the amino acid sequence as depicted in SEQ ID NO:7 or the sulfoacetaldehyde acetyltransferase of *Roseovarius nubinhibens* showing the amino acid sequence as depicted in SEQ ID NO:8 or showing a related amino acid sequence.

Thus, in a preferred embodiment, the sulfoacetaldehyde acetyltransferase employed in the method of the invention has an amino acid sequence as shown in any one of SEQ ID NOs: 4 to 8 or shows an amino acid sequence which is at least x % homologous to any one of SEQ ID NOs: 4 to 8 and is a sulfoacetaldehyde acetyltransferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting a 2-hydroxyaldehyde and phosphate into an acyl phosphate as set forth herein above. Preferably, the degree of identity is determined as described above.

The enzymatic activity of a sulfoacetaldehyde acetyltransferase (EC 2.3.3.15) can be assessed with methods known to a person skilled in the art. Such methods are, e.g., described in Ruff et al. (Biochem. J. 369 (2003), 275-285).

In the appended Examples it is shown that D,L-lactaldehyde (racemic 2-hydroxypropanal) and D,L-glyceraldehyde (racemic 2,3-hydroxypropanal) can be converted by sulfoacetaldehyde acetyltransferases into propionyl phosphate and 3-hydroxypropionyl phosphate, respectively, which can then be further converted into propionic acid and 3-hydroxypropionic acid, respectively, by spontaneous hydrolyzation.

In a preferred embodiment, the 2-hydroxyaldehyde of the following formula

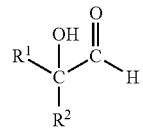

2-hydroxyaldehyde wherein $R^1$ and $R^2$ are selected independently from H, $CH_3$, $CH_2OH$ and $C2H5$ and wherein if $R^1$ is H, $R^2$ cannot be H, which is converted into an acyl phosphate according to a method of the present invention, is 2-hydroxypropanal (lactaldehyde) which is converted into propionyl phosphate. Thus, in a preferred embodiment, the present invention relates to a method for the enzymatic production of propionyl phosphate from 2-hydroxypropanal (lactaldehyde) by making use of a phosphoketolase or of a sulfoacetaldehyde acetyltransferase (EC 2.3.3.15) wherein the conversion of 2-hydroxypropanal (lactaldehyde) into propionyl phosphate occurs according to the following reaction scheme:

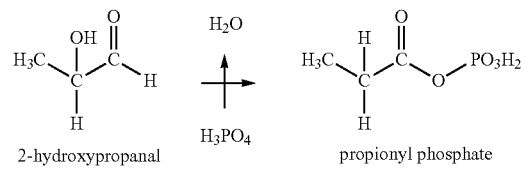

In another preferred embodiment, the 2-hydroxyaldehyde of the following formula

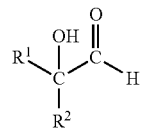

2-hydroxyaldehyde wherein $R^1$ and $R^2$ are selected independently from H, CH3, $CH_2OH$ and $C_2H5$ and wherein if $R^1$ is H, $R^2$ cannot be H, which is converted into an acyl phosphate according to a method of the present invention, is 2,3-dihydroxypropanal (glyceraldehyde) which is converted into 3-hydroxypropionyl phosphate. Thus, in a preferred embodiment, the present invention relates to a method for the enzymatic production of 3-hydroxypropionyl phosphate from 2,3-dihydroxypropanal (glyceraldehyde) by making use of a phosphoketolase or of a sulfoacetaldehyde acetyltransferase (EC 2.3.3.15) wherein the conversion of 2,3-dihydroxypropanal (glyceraldehyde) into 3-hydroxypropionyl phosphate occurs according to the following reaction scheme:

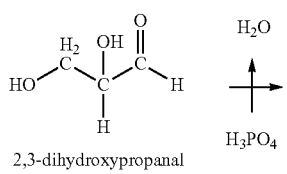

2,3-dihydroxypropanal

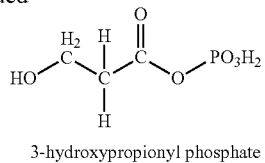

3-hydroxypropionyl phosphate

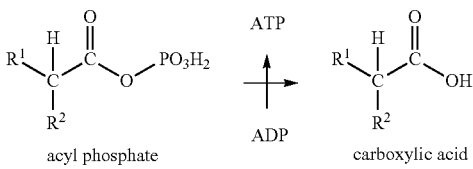

acyl phosphate    carboxylic acid

The acyl phosphate produced according to a method of the present invention can be further converted into desired molecules such as a carboxylic acid or a corresponding acyl-Coenzyme A (also referred to as acyl-CoA).

The conversion of an acyl phosphate into the corresponding carboxylic acid can occur via hydrolysis which functions according to the following reaction scheme:

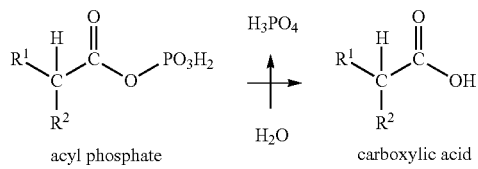

acyl phosphate    carboxylic acid wherein $R^1$ and $R^2$ are selected independently from H, $C_3$, $CH_2OH$ and $C_2H5$ and wherein if $R^1$ is H, $R^2$ cannot be H.

The hydrolysis of an acyl phosphate as defined herein above into a corresponding carboxylic acid in vitro can occur spontaneously since acyl phosphates are rather unstable.

It is also possible to achieve the conversion by an enzymatically catalyzed reaction. The enzymatic hydrolysis of an acyl phosphate into the corresponding carboxylic acid and $H_3PO_4$ can, for example, be achieved by making use of an acylphosphatase (EC 3.6.1.7). Acylphosphatase (AcP; EC 3.6.1.7) is a cytosolic enzyme (with a molecular weight of about 10 kDa) widely expressed in eukaryotic and prokaryotic organisms (both mesophilic and extremophilic). AcP can be found in many tissues of vertebrate species in the skeletal muscles and in the heart as muscle-type AcP (MT-AcP) and in erythrocytes, brain and testis as (organ) common-type AcP (CT-AcP) (Zuccotti et al., Acta Cryst. 61 (2005), 144-146). Acylphosphatases catalyze the following reaction:

Acyl phosphate+$H_2O$→carboxylic acid+$H_3PO_4$

This enzyme has been described in a large variety of organisms. Preferably, an acylphosphatase employed in a method according to the present invention is derived from *Gallus gallus, Cavia porcellus* (Liguri et al., Biochem. J. 217 (1984), 499-505), *Homo sapiens, Sus scrofa, Bos taurus, Oryctolagus cuniculus, Equus acallus* or *Pyrococcus hirokoshii* (Miyazoo et al., Acta Crystallographica D60 (2004), 1135-1136).

The structural and functional characteristics of these enzymes have already been studied in detail and are described, e.g., in Liguri et al. (Biochem. J. 217 (1984), 499-505), Miyazoo et al. (Acta Crystallographica D60 (2004), 1135-1136) and in Taddei et al. (FEBS Letters 362 (1995), 175-179).

Alternatively, it can occur by an enzymatic reaction which involves the generation of ATP from ADP according to the following reaction scheme:

In particular, an acyl phosphate can also be converted, in vitro or in vivo, enzymatically into a corresponding carboxylic acid, e.g. by making use of an enzyme which is classified as EC 2.7.2.-, i.e., a phosphotransferase. Such enzymes use a carboxyl group as acceptor. Thus, the conversion of an acyl phosphate into the corresponding carboxylic acid can, e.g., be achieved by making use of an enzyme with a carboxy group as acceptor (EC 2.7.2.-). Examples of such enzymes are enzymes which are classified as an acetate kinase (EC 2.7.2.1), as a butyrate kinase (EC 2.7.2.7), as an acetate kinase (diphosphate) (EC 2.7.2.12), as a branched-chain-fatty-acid kinase (EC 2.7.2.14) or as a propionate kinase (EC 2.7.2.15).

Acetate kinase (EC 2.7.2.1) is an enzyme which catalyzes the following reaction:

ATP+acetate ⇌ ADP+acetyl phosphate.

Since this reaction is reversible, the enzyme can be employed to convert an acyl phosphate into the corresponding carboxylic acid. The reaction may be pushed into the direction of the carboxylic acid by continuously removing ATP from the reaction, e.g. by further enzymatic conversion or by removal from the reaction by means and methods known to the person skilled in the art. This enzyme occurs in a large variety of organisms, in particular in prokaryotes, eukaryotes and archae. It is an important enzyme in glycolysis and the enzyme levels are normally increased in the presence of excess glucose. This enzyme has, e.g., been described to occur in a number of organisms, in particular bacteria and eukaryotes. In one preferred embodiment the enzyme is from a bacterium, preferably from a bacterium of the genus *Methanosarcina, Cryptococcus, Ethanoligenens, Propionibacterium, Roseovarius, Streptococcus, Salmonella, Acholeplasma, Acinetobacter, Ajellomyces, Bacillus, Borrelia, Chaetomium, Clostridium, Coccidioides, Coprinopsis, Cryptococcus, Cupriavidus, Desulfovibrio, Enterococcus, Escherichia, Ethanoligenes, Geobacillus, Helicobacter, Lactobacillus, Lactococcus, Listeria, Mesoplasma, Moorella, Mycoplasma, Oceanobacillus, Propionibacterium, Rhodospseudomonas, Roseovarius, Salmonella, Staphylococcus, Thermotoga* or *Veillonella*, more preferably from a bacterium of the species *Methanosarcina thermophila, Cryptococcus neoformans, Ethanoligenens harbinense, Propionibacterium acidipropionici, Streptococcus pneumoniae, Streptococcus enterica, Streptococcus pyogenes, Acholeplasma laidlawii, Acinetobacter calcoaceticus, Ajellomyces capsulatus, Bacillus subtilis, Borrelia burgdorferi, Chaetomium globosum, Clostridium acetobutylicum, Clostridium thermocellum, Coccidioides immitis, Coprinopsis cinerea, Cryptococcus neoformans, Cupriavidus necator, Desulfovibrio vulgaris, Enterococcus faecalis, Escherichia coli, Ethanoligenes harbinense, Geobacillus stearothermophilus, Helicobacter pylori, Lactobacillus delbrueckii, Lactobacillus acidophilus, Lactobacillus sanfranciscensis, Lactococcus lactis, Listeria monocytogenes, Mesoplasma florum, Methanosarcina acetivorans, Methanosarcina mazei, Moorella thermoacetica, Mycoplasma pneumoniae, Oceanobacillus iheyensis, Propionibacterium*

*freudenreichii, Propionibacterium acidipropionici, Rhodospeudomonas palustris, Salmonella enteric, Staphylococcus aureus, Thermotoga maritime* or *Veillonella parvula*.

In another preferred embodiment the enzyme is an enzyme from a fungus, preferably from a fungus of the genus *Aspergillus, Gibberella, Hypocrea, Magnaporthe, Phaeosphaeria, Phanerochaete, Phytophthora, Sclerotinia, Uncinocarpus, Ustilago* or *Neurospora* even more preferably from a fungus of the species *Aspergillus fumigates, Aspergillus nidulans, Gibberella zeae, Hypocrea jecorina, Magnaporthe grisea, Phaeosphaeria nodorum, Phanerochaete chrysosporium, Phytophthora ramorum, Phytophthora sojae, Sclerotinia sclerotiorum, Uncinocarpus reesii, Ustilago maydis* or *Neurospora crassa*.

In a further preferred embodiment the enzyme is an enzyme from a plant or an algae, preferably from the genus *Chlamydomonas*, even more preferably from the species *Chlamydomonas reinhardtii*.

In another embodiment the enzyme is from an organism of the genus *Entamoeba*, more preferably of the species *Entamoeba histolytica*.

In principle any acetate kinase (EC 2.7.2.1) can be used which is able to convert an acyl phosphate into the corresponding carboxylic acid in a method according to the invention.

The conversion of an acyl phosphate into the corresponding carboxylic acid can also be achieved by making use of a butyrate kinase (EC 2.7.2.7). Butyrate kinases are enzymes which catalyze the following reaction:

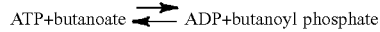

It has been described, e.g. by Hartmanis (J. Biol. Chem. 262 (1987), 617-621) that butyrate kinase can use a number of substrates in addition to butyrate, e.g. valerate, isobutyrate, isovalerate and vinyl acetate. The enzyme has been described in a variety of organisms, in particular bacteria. In one preferred embodiment the enzyme is from a bacterium, preferably from a bacterium of the genus *Lactobacillus, Geobacillus, Clostridium, Butyrivibrio, Thermotoga* or *Enterococcus*. Preferred is *Clostridium, Lactobacillus* or *Geobacillus*. More preferably the enzyme is from a bacterium of the species *Clostridium acetobutylicum, Clostridium proteoclasticum, Clostridium tyrobutyricum, Clostridium butyricum, Clostridium pasteurianum, Clostridium tetanomorphum, Butyrivibrio firbrosolvens, Butyrivibrio hungatei, Thermotoga maritime* or *Enterococcus durans*. Preferred is *Clostridium acetobutylicum*. For this organism two butyrate kinases have been described: butyrate kinase 1 (Uniprot Accession number: Q45829) and butyrate kinase II (Uniprot Accession number: Q97II19). In another preferred embodiment the butyrate kinase is a butyrate kinase from *Lactobacillus casei*, e.g. *Lactobacillus casei* W56 (Uniprot Accession number: K0N529) or from *Geobacillus* sp., e.g. *Geobacillus* sp. GHH01 (Uniprot Accession number: L8A0E1). The amino acid sequences of said proteins are shown in SEQ ID NO: 13 and 14, respectively.

It is, of course, not only possible to use an enzyme exactly showing the amino acid of SEQ ID NO: 13 or 14. It is also possible to use an enzyme which comprises a sequence which is at least 60% identical to the amino acid sequence shown in SEQ ID NO: 13 or 14. Preferably, the sequence identity is at least 70%, more preferably at least 80%, 85% or 90%, even more preferably 91%, 92%, 93, %, 94%, 95%, 96%, 97%, 98% and particularly preferred at least 99% to SEQ ID NO: 13 or 14 and the enzyme has the enzymatic activity of converting an acyl phosphate as defined herein above into the corresponding carboxylic acid. As regards the determination of the sequence identity, the same applies as has been set forth above.

Moreover, the conversion of an acyl phosphate into the corresponding carboxylic acid can also be achieved by making use of an acetate kinase (diphosphate) (EC 2.7.2.12). Acetate kinases (diphosphate) (EC 2.7.2.12) are enzymes which naturally catalyze the following reaction:

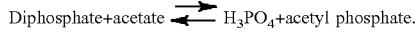

This enzyme has been described to occur in *Entamoeba histolytica*.

Moreover, the conversion of an acyl phosphate into the corresponding carboxylic acid can also be achieved by making use of a branched-chain-fatty-acid kinase (EC 2.7.2.14). Branched-chain-fatty-acid kinases (EC 2.7.2.14) naturally catalyze the following reaction:

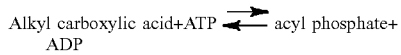

wherein "alkyl" may be 2-methylbutanoate, butanoate, isobutanoate, pentanoate or propionate. The latter reaction with propionate has been described for a branched-chain fatty acid kinase from a spirochaete (J. Bacteriol. 152 (1982), 246-54).

This enzyme has been described to occur in a number of bacteria. Thus, in one preferred embodiment the enzyme is an enzyme from a bacterium, preferably of the genus *Spirochaeta* or *Thermotoga*, more preferably *Thermotoga maritime*.

Also a propionate kinase (EC 2.7.2.15) can be used for the conversion of an acyl phosphate as defined herein above into the corresponding carboxylic acid. Propionate kinases (EC 2.7.2.15) naturally catalyze the following reactions:

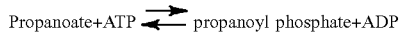

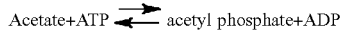

This enzyme has been described to occur in a number of bacteria, in particular Enterobacteriacea. Thus, in one preferred embodiment the enzyme is an enzyme from a bacterium, preferably of the genus *Salmonella* or *Escherichia*, more preferably of the species *Salmonella enterica, Salmonella typhimurium* or *Escherichia coli*.

In a preferred embodiment, the conversion of an acyl phosphate as defined herein above into the corresponding carboxylic acid is achieved by making use of a propionate kinase from *Salmonella typhimurium*, preferably from *Salmonella typhimurium* strain ATCC 700720. The amino acid sequence of said protein is shown in SEQ ID NO: 9.

It is, of course, not only possible to use an enzyme exactly showing this amino acid of SEQ ID NO: 9. It is also possible to use an enzyme which comprises a sequence which is at least 60% identical to the amino acid sequence shown in SEQ ID NO: 9. Preferably, the sequence identity is at least 70%, more preferably at least 80%, 85% or 90%, even more preferably 91%, 92%, 93, %, 94%, 95%, 96%, 97%, 98% and particularly preferred at least 99% to SEQ ID NO:9 and the enzyme has the enzymatic activity of converting an acyl phosphate as defined herein above into the corresponding carboxylic acid. As regards the determination of the sequence identity, the same applies as has been set forth above.

In another preferred embodiment, the conversion of an acyl phosphate as defined herein above into the corresponding carboxylic acid is achieved by making use of a propionate kinase from *Escherichia coli*, preferably from Escherichia coli strain K12. The amino acid sequence of said protein is shown in SEQ ID NO: 10.

It is, of course, not only possible to use an enzyme exactly showing the amino acid of SEQ ID NO: 10. It is also possible to use an enzyme which comprises a sequence which is at least 60% identical to the amino acid sequence shown in SEQ ID NO: 10. Preferably, the sequence identity is at least 70%, more preferably at least 80%, 85% or 90%, even more preferably 91%, 92%, 93, %, 94%, 95%, 96%, 97%, 98% and particularly preferred at least 99% to SEQ ID NO: 10 and the enzyme has the enzymatic activity of converting an acyl phosphate as defined herein above into the corresponding carboxylic acid. As regards the determination of the sequence identity, the same applies as has been set forth above.

As is evident from the PROSITE database (http://prosite.expasy.org/cgi-bin/prosite/prosite-search-ac?PDOC00826#ref1), acetate kinases, butyrate kinases and propionate kinases are evolutionary related.

There are two signature patterns for these enzymes; the first one is located in the N-terminal section and the second in the central section. Both of them are glycine-rich and are suspected to be involved in substrate or ATP-binding.

The first consensus pattern (signature 1) is:
[LIVMFANT]-[LIVM]-x-[LIVMA]-N-x-G-S-[ST](2)-x-[KE]

The reference for this signature in PROSITE DATABASE is PS01075

The second consensus pattern (signature 2) is:
[LIVMFATQ]-[LIVMA]-x(2)-H-x-G-x-[GT]-x-[ST]-[LIVMA]-x-[TAVC]-x(3)-G The reference for this signature in PROSITE DATABASE is PS01076

As described above, in a preferred embodiment, the 2-hydroxyaldehyde which is converted in a method according to the present invention is 2-hydroxypropanal and it is converted into propionyl phosphate. In a preferred embodiment the propionyl phosphate is further converted into the corresponding carboxylic acid, i.e. propanoic acid, as described herein above. The corresponding reaction can, e.g., occur according to one of the following reaction schemes:

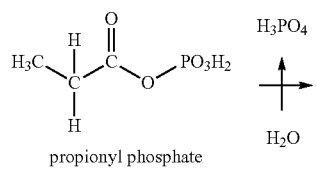
propionyl phosphate

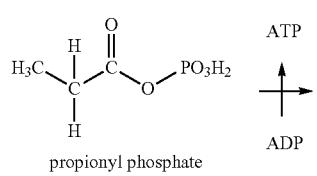
propionyl phosphate

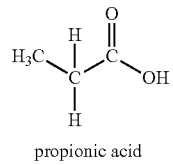
propionic acid

The conversion of propionyl phosphate into propanoic acid is preferably achieved by making use of a propionate kinase (EC 2.7.2.15) as described above.

Propanoic acid (also referred to as propionic acid) is of commercial interest because it can be employed in a number of technical fields. It is primarily manufactured for use as a preservative and anti-mold agent in animal feed and grain. It is also used as a preservative and flavouring agent in packaged foods such as baked goods and cheese. For example, calcium propionate and sodium propionate, the salt forms of propanoic acid, are used in bread and tortillas to prevent mold. Furthermore, propanoic acid is used as a chemical building block for the production of herbicides, pharmaceuticals, dyes, textile and rubber products, plastics, plasticizers, cosmetics and perfumes.

Moreover, as described above, in a preferred embodiment, the 2-hydroxyaldehyde which is converted in a method according to the present invention is 2,3-dihydroxypropanal and it is converted into 3-hydroxypropionyl phosphate. In a preferred embodiment the 3-hydroxypropionyl phosphate is further converted into the corresponding carboxylic acid, i.e. 3-hydroxypropanoic acid, as described herein above. The corresponding reaction may occur, e.g., according to one of the following reaction schemes:

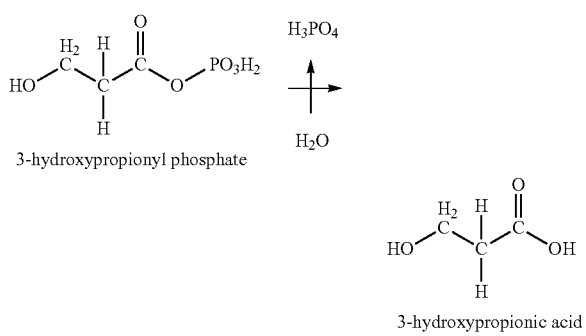

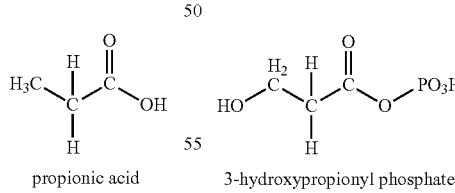
3-hydroxypropionyl phosphate

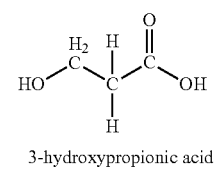
3-hydroxypropionic acid

The conversion of propionyl phosphate into propanoic acid is preferably achieved by making use of a propionate kinase (EC 2.7.2.7) as described above. Preferred are enzymes from *Lactobacillus casei* W56 (Uniprot Accession number: K0N529) or from *Geobacillus* sp., e.g. *Geobacillus* sp. GHH01 (Uniprot Accession number: L8A0E1). The amino acid sequences of said proteins are shown in SEQ ID NO: 13 and 14, respectively.

It is, of course, not only possible to use an enzyme exactly showing the amino acid of SEQ ID NO: 13 or 14. It is also possible to use an enzyme which comprises a sequence which is at least 60% identical to the amino acid sequence shown in SEQ ID NO: 13 or 14. Preferably, the sequence identity is at least 70%, more preferably at least 80%, 85% or 90%, even more preferably 91%, 92%, 93, %, 94%, 95%, 96%, 97%, 98% and particularly preferred at least 99% to SEQ ID NO: 13 or 14 and the enzyme has the enzymatic activity of converting propionyl phosphate or 3-hydroxypropionyl phosphate above into propanoic acid or 3-hydroxypropionic acid.

As regards the determination of the sequence identity, the same applies as has been set forth above.

3-hydroxypropanoic acid (also referred to as 3-hydroxypropionic acid; 3-HP), as propanoic acid, is also of commercial relevance. It is a platform chemical which can be converted into acrylic acid, 1,3-propanediol, malonic acid, biodegradable polyesters and other valuable chemicals. Acrylic acid-derived products include superabsorbent polymers used in baby diapers and incontinence products, plastics, coatings, adhesives, elastomers and paints. Currently, acrylic acid is primarily made by catalytic oxidation of propene. The possibility to provide the precursor 3-HP from glucose or other renewable resources would provide a biosustainable alternative to acrylic acid production from fossil resources.

As mentioned above, the acyl phosphate produced by a method of the present invention can also be further converted into a corresponding acyl-Coenzyme A (acyl-CoA). Such a conversion occurs via the following reaction scheme:

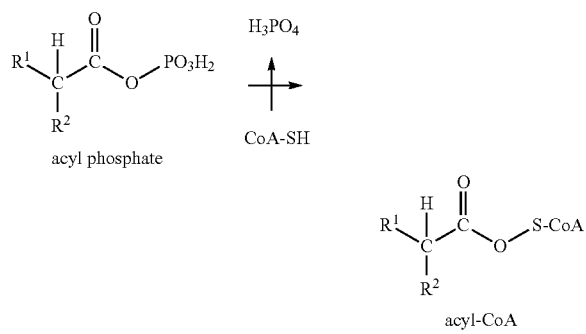

acyl phosphate acyl-CoA wherein $R^1$ and $R^2$ are selected independently from H, $C_3$, $CH_2OH$ and $C_2H5$ and wherein if $R^1$ is H, $R^2$ cannot be H.

The conversion of an acyl phosphate into a corresponding acyl-CoA (in vitro or in vivo) can be achieved enzymatically, e.g. by the use of a phosphate acetyltransferase (EC 2.3.1.8) or by the use of a phosphate butyryltransferase (EC 2.3.1.19).

Phosphate acetyltransferases (EC 2.3.1.8) naturally catalyze the following reaction:

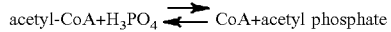

It has been described by Veit et al. (J. Biotechnol. 140 (2009), 75-83) that phosphate acetyltransferase can also use as a substrate butyryl-CoA or propionyl-CoA.

The accession numbers for this enzyme family in InterPro database are IPR012147 and IPR002505, "http://www.ebi-.ac.uk/interpro/entry/IPR002505" (http://www.ebi.ac.uk/interpro/entry/IPR002505" (http://www.ebi.ac.uk/interpro/entry/IPR012147 http://www.ebi.ac.uk/interpro/entry/IPR002505) See also http://pfam.sanger.ac.uk/family/PF01515

The enzyme has been described in a variety of organisms, in particular bacteria and fungi. Thus, in one preferred embodiment the enzyme is an enzyme from a bacterium, preferably of the genus *Escherichia, Chlorogonium, Clostridium, Veillonella, Methanosarcina, Corynebacterium, Ruegeria, Salmonella, Azotobacter, Bradorhizobium, Lactobacillus, Moorella, Rhodopseudomonas, Sinorhizobium, Streptococcus, Thermotoga* or *Bacillus*, more preferably of the species *Escherichia coli, Chlorogonium elongatum, Clostridium kluyveri, Clostridium acetobutylicum, Clostridium acidurici, Veillonella parvula, Methanosarcina thermophila, Corynebacterium glutamicum, Ruegeria pomeroyi, Salmonella enterica, Azotobacter vinelandii, Bradyrhizobium japonicum, Lactobacillus fermentum, Lactobacillus sanfranciscensis, Moorella thermoacetica, Rhodopseudomonas palustris, Sinorhizobium meliloti, Streptococcus pyogenes, Thermotoga maritima* or *Bacillus subtilis*. In another preferred embodiment the enzyme is an enzyme from a fungus, preferably from the genus *Saccharomyces*, more preferably of the species *Saccharomyces cerevisiae*.

In a preferred embodiment, the conversion of acyl phosphate into acyl-CoA is achieved by making use a phosphate acetyltransferase from *Corynebacterium glutamicum*, preferably from *Corynebacterium glutamicum* strain ATCC 13032. The amino acid sequence of said protein is shown in SEQ ID NO: 11.

It is, of course, not only possible to use an enzyme exactly showing the amino acid of SEQ ID NO: 11. It is also possible to use an enzyme which comprises a sequence which is at least 60% identical to the amino acid sequence shown in SEQ ID NO: 11. Preferably, the sequence identity is at least 70%, more preferably at least 80%, 85% or 90%, even more preferably 91%, 92%, 93, %, 94%, 95%, 96%, 97%, 98% and particularly preferred at least 99% to SEQ ID NO: 11 and the enzyme has the enzymatic activity of converting acyl phosphate into acyl-CoA. As regards the determination of the sequence identity, the same applies as has been set forth above.

As mentioned above, the conversion of an acyl phosphate into a corresponding acyl-CoA (in vitro or in vivo) can also be achieved by making use of a phosphate butyryltransferase (EC 2.3.1.19).

Phosphate butyryltransferases (EC 2.3.1.19) naturally catalyze the following reaction

It has been described by Wiesenborn et al. (Appl. Environ. Microbiol. 55 (1989), 317-322) and by Ward et al. (J. Bacteriol. 181 (1999), 5433-5442) that phosphate butyryltransferases (EC 2.3.1.19) can use a number of substrates in addition to butyryl coenzyme A (butyryl-CoA), in particular acetyl-CoA, propionyl-CoA, isobutyryl-CoA, valeryl-CoA and isovaleryl-CoA.

The enzyme has been described to occur in a number of organisms, in particular in bacteria and in protozoae. In one embodiment the enzyme is from the protozoae Dasytricha ruminantium. In a preferred embodiment the phosphate butyryltransferase is a phosphate butyryltransferase from a bacterium, preferably from a bacterium of the genus *Bacillus, Butyrivibrio, Enterococcus* or *Clostridium*, more preferably *Enterococcus* or *Clostridium*, and even more preferably from *Bacillus subtilis*, *Bacillus megaterium*, *Butyrivibrio fibrisolvens*, *Clostridium acetobutylicum*, *Clostridium beijerinckii*, *Clostridium butyricum*, *Clostridium kluyveri*, *Clostridium saccharoacetobutylicum*, *Clostridium sprorogenes* or *Enterococcus faecalis*. Most preferably, the enzyme is from *Clostridium acetobutylicum*, in particular the enzyme encoded by the ptb gene (Uniprot Accession number F0K6W0; Wiesenborn et al. (Appl. Environ. Microbiol. 55 (1989), 317-322)), from *Enterococcus faecalis* (Uniprot Accession number K4YRE8; Ward et al. (J. Bacteriol. 181 (1999), 5433-5442)) or from *Bacillus subtilis*, in particular from strain 168 (Uniprot Accession Number P54530).

In one preferred embodiment, the conversion of an acyl phosphate into a corresponding acyl-CoA is achieved by making use of a phosphate butyryltransferase from *Clostridium acetobutylicum*, preferably from *Clostridium acetobutylicum* strain ATCC 824. The amino acid sequence of said protein is shown in SEQ ID NO: 12.

It is, of course, not only possible to use an enzyme exactly showing the amino acid of SEQ ID NO: 12. It is also possible to use an enzyme which comprises a sequence which is at least 60% identical to the amino acid sequence shown in SEQ ID NO: 12. Preferably, the sequence identity is at least 70%, more preferably at least 80%, 85% or 90%, even more preferably 91%, 92%, 93, %, 94%, 95%, 96%, 97%, 98% and particularly preferred at least 99% to SEQ ID NO: 12 and the enzyme has the enzymatic activity of converting an acyl phosphate into a corresponding acyl-CoA. As regards the determination of the sequence identity, the same applies as has been set forth above.

In another preferred embodiment, the conversion of a acyl phosphate into a corresponding acyl-CoA is achieved by making use of a phosphate butyryltransferase from *Bacillus subtilis*, in particular from strain 168 (Uniprot Accession Number P54530). The amino acid sequence of said protein is shown in SEQ ID NO: 15.

It is, of course, not only possible to use an enzyme exactly showing the amino acid of SEQ ID NO: 15. It is also possible to use an enzyme which comprises a sequence which is at least 60% identical to the amino acid sequence shown in SEQ ID NO: 15. Preferably, the sequence identity is at least 70%, more preferably at least 80%, 85% or 90%, even more preferably 91%, 92%, 93, %, 94%, 95%, 96%, 97%, 98% and particularly preferred at least 99% to SEQ ID NO: 15 and the enzyme has the enzymatic activity of converting an acyl phosphate into a corresponding acyl-CoA. As regards the determination of the sequence identity, the same applies as has been set forth above.

As described above, in a preferred embodiment, the 2-hydroxyaldehyde which is converted in a method according to the present invention is 2-hydroxypropanal and it is converted into propionyl phosphate. In a preferred embodiment the propionyl phosphate is further converted into the corresponding acyl-CoA, i.e. propionyl-CoA, as described herein above. The corresponding reaction may, e.g., occur according to one of the following reaction scheme:

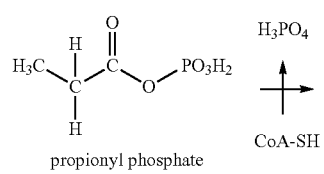

propionyl phosphate

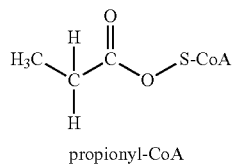

propionyl-CoA

The conversion of propionyl phosphate into propionyl-CoA in accordance with this scheme is preferably achieved by making use of a phosphate butyryltransferase, more preferably a phosphate butyryltransferase from *Clostridium acetobutylicum*, *Bacillus subtilis* or *Enterococcus faecalis*, even more preferably the corresponding enzymes as described above.

Moreover, as described above, in a preferred embodiment, the 2-hydroxyaldehyde which is converted in a method according to the present invention is 2,3-dihydroxypropanal and it is converted into 3-hydroxypropionyl phosphate. In a preferred embodiment the 3-hydroxypropionyl phosphate is further converted into the corresponding acyl-CoA, i.e. 3-hydroxypropionyl-CoA, as described herein above. The corresponding reaction may, e.g., occur according to one of the following reaction scheme:

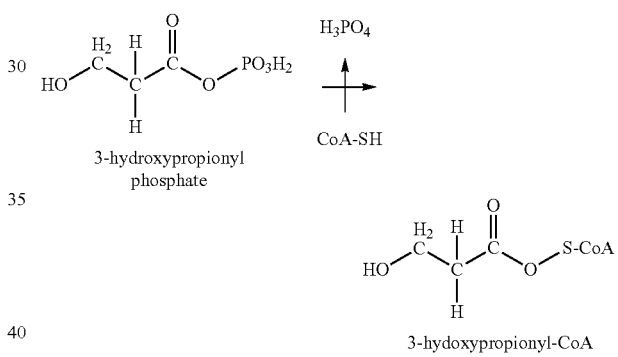

The conversion of 3-hydroxypropionyl phosphate into 3-hydroxypropionyl-CoA in accordance with this scheme is preferably achieved by making use of a phosphate butyryltransferase, more preferably a phosphate butyryltransferase from *Bacillus subtilis* or *Enterococcus faecalis*, even more preferably the corresponding enzymes as described above.

The method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form.

For carrying out the method in vitro the substrates for the reaction and the enzymes are incubated under conditions (buffer, temperature, co-substrates, co-factors etc.) allowing the enzymes to be active and the enzymatic conversion to occur. The reaction is allowed to proceed for a time sufficient to produce the respective product. The production of the respective products can be measured by methods known in the art, such as liquid chromatography (HPLC) possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

The Examples illustrate in vitro reactions according to the invention using phosphoketolases from different origins.

In another embodiment the method according to the invention is carried out in culture, in the presence of an organism, preferably a microorganism, producing at least a phosphoketolase or a sulfoacetaldehyde acetyltransferase and optionally enzymes which are necessary for providing the 2-hydroxyaldehyde or for further converting the produced acyl phosphate into other compounds, such as a carboxylic acid or the acyl-CoA, as described herein above. A method which employs a microorganism for carrying out a method according to the invention is referred to as an "in vivo" method. The 2-hydroxyaldehyde may either be provided externally or may be produced by the employed microorganism expressing the phosphoketolase or the sulfoacetaldehyde acetyltransferase itself. Such a microorganism expresses at least one enzyme necessary for the enzymatic production of the 2-hydroxyaldehyde. It is also possible to co-culture a microorganism which is capable of producing a 2-hydroxyaldehyde and a microorganism which expresses a phosphoketolase and/or a sulfoacetaldehyde acetyltransferase so as to convert the 2-hydroxyaldehyde produced by the first microorganism.

Thus, in such embodiments of the invention, a microorganism that produces at least a phosphoketolase or a sulfoacetaldehyde acetyltransferase as described above is used. It is possible to use a microorganism which naturally produces the phosphoketolase or the sulfoacetaldehyde acetyltransferase or a microorganism which had been genetically modified so that it expresses (or overexpresses) a phosphoketolase and/or the sulfoacetaldehyde acetyltransferase. Thus, the microorganism can be a microorganism which naturally expresses a phosphoketolase and/or a sulfoacetaldehyde acetyltransferase, i.e. which naturally has in its genome a nucleotide sequence encoding a phosphoketolase or a sulfoacetaldehyde acetyltransferase and which expresses it/them. The expression may occur constitutively or in an induced or regulated manner. Microorganisms that inherently, i.e. naturally, have phosphoketolase activity or sulfoacetaldehyde acetyltransferase activity are known in the art and any of them can be used in the context of the present invention.

In another embodiment the microorganism can be a microorganism which has been genetically modified by the introduction of a nucleic acid molecule containing a nucleotide sequence encoding a phosphoketolase or a sulfoacetaldehyde acetyltransferase. The nucleic acid molecule can be stably integrated into the genome of the microorganism or may be present in an extrachromosomal manner, e.g. on a plasmid.

Such a genetically modified microorganism can, e.g., be a microorganism that does not naturally have phosphoketolase activity or sulfoacetaldehyde acetyltransferase activity and has been genetically modified to express a phosphoketolase or a sulfoacetaldehyde acetyltransferase or a microorganism which naturally has phosphoketolase activity or sulfoacetaldehyde acetyltransferase activity and which has been genetically modified, e.g. by transformation with a nucleic acid, e.g. a vector, encoding a phosphoketolase or a sulfoacetaldehyde acetyltransferase in order to increase the phosphoketolase activity or sulfoacetaldehyde acetyltransferase activity in said microorganism and/or by insertion of a promoter in front of the endogenous nucleotide sequence encoding the enzyme in order to increase the respective activity in said microorganism.

However, the invention preferably excludes naturally occurring microorganisms as found in nature expressing an enzyme as described above at levels as they exist in nature. Instead, the microorganism of the present invention and employed in a method of the present invention is preferably a non-naturally occurring microorganism, whether it has been genetically modified to express (including overexpression) an exogenous enzyme of the invention not normally existing in its genome or whether it has been engineered to overexpress an exogenous enzyme.

Thus, the enzymes and (micro)organisms employed in connection with the present invention are preferably non-naturally occurring enzymes or (microorganisms), i.e. they are enzymes or (micro)organisms which differ significantly from naturally occurring enzymes or microorganism and which do not occur in nature. As regards the enzymes, they are preferably variants of naturally occurring enzymes which do not as such occur in nature. Such variants include, for example, mutants, in particular prepared by molecular biological methods, which show improved properties, such as a higher enzyme activity, higher substrate specificity, higher temperature resistance and the like. As regards the (micro)organisms, they are preferably genetically modified organisms as described herein above which differ from naturally occurring organisms due to a genetic modification. Genetically modified organisms are organisms which do not naturally occur, i.e., which cannot be found in nature, and which differ substantially from naturally occurring organisms due to the introduction of a foreign nucleic acid molecule.

By overexpressing an exogenous or endogenous enzyme as described herein above, the concentration of the enzyme is substantially higher than what is found in nature, which can then unexpectedly force the reaction of the present invention which uses a non-natural for the respective enzyme. Preferably, the concentration of the overexpressed enzyme is at least 5%, 10%, 20%, 30% or 40% of the total host cell protein.

A "non-natural" substrate is understood to be a molecule that is not acted upon by the respective enzyme in nature, even though it may actually coexist in the microorganism along with the endogenous enzyme. This "non-natural" substrate is not converted by the microorganism in nature as other substrates are preferred (e.g. the "natural substrate"). Thus, the present invention contemplates utilizing a non-natural substrate with the enzymes described above in an environment not found in nature.

Thus, it is also possible in the context of the present invention that the microorganism is a microorganism which naturally does not have phosphoketolase activity or sulfoacetaldehyde acetyltransferase activity but which is genetically modified so as to comprise a nucleotide sequence allowing the expression of a phosphoketolase or a sulfoacetaldehyde acetyltransferase. Similarly, the microorganism may also be a microorganism which naturally has phosphoketolase activity or sulfoacetaldehyde acetyltransferase activity but which is genetically modified so as to enhance the phosphoketolase activity or sulfoacetaldehyde acetyltransferase activity, e.g. by the introduction of an exogenous nucleotide sequence encoding a phosphoketolase or a sulfoacetaldehyde acetyltransferase or by the introduction of a promoter for the endogenous gene encoding the enzyme to increase endogenous production to overexpressed (non-natural) levels.

If a microorganism is used which naturally expresses a phosphoketolase or a sulfoacetaldehyde acetyltransferase, it is possible to modify such a microorganism so that the respective activity is overexpressed in the mircroorganism. This can, e.g., be achieved by effecting mutations in the promoter region of the corresponding gene or introduction of a high expressing promoter so as to lead to a promoter which ensures a higher expression of the gene. Alternatively, it is also possible to mutate the gene as such so as to lead to an enzyme showing a higher activity.

By using microorganisms which express a phosphoketolase or a sulfoacetaldehyde acetyltransferase, it is possible to carry out the method according to the invention directly in the culture medium, without the need to separate or purify the enzymes.

In one embodiment the organism employed in the method according to the invention is a microorganism which has been genetically modified to contain a foreign nucleic acid molecule encoding a phosphoketolase or a sulfoacetaldehyde acetyltransferase. The term "foreign" or "exogenous" in this context means that the nucleic acid molecule does not naturally occur in said microorganism. This means that it does not occur in the same structure or at the same location in the microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. "Heterologous" in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the microorganism, i.e. a promoter which does naturally not occur in the respective microorganism. Even more preferably, the promoter is an inducible promoter. Promoters for driving expression in different types of organisms, in particular in microorganisms, are well known to the person skilled in the art.

In a further embodiment the nucleic acid molecule is foreign to the microorganism in that the encoded enzyme is not endogenous to the microorganism, i.e. is naturally not expressed by the microorganism when it is not genetically modified. In other words, the encoded enzyme is heterologous with respect to the microorganism. The foreign nucleic acid molecule may be present in the microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus Bacillus, Clostridium, Corynebacterium, Pseudomonas, Zymomonas or Escherichia. In a particularly preferred embodiment the bacterium belongs to the genus Escherichia and even more preferred to the species Escherichia coli. In another preferred embodiment the bacterium belongs to the species Pseudomonas putida or to the species Zymomonas mobilis or to the species Corynebacterium glutamicum or to the species Bacillus subtilis.

It is also possible to employ an extremophilic bacterium such as Thermus thermophilus, or anaerobic bacteria from the family Clostridiae.

In another preferred embodiment the microorganism is a fungus, more preferably a fungus of the genus Saccharomyces, Schizosaccharomyces, Aspergillus, Trichoderma, Kluyveromyces or Pichia and even more preferably of the species Saccharomyces cerevisiae, Schizosaccharomyces pombe, Aspergillus niger, Trichoderma reesei, Kluyveromyces marxianus, Kluyveromyces lactis, Pichia pastoris, Pichia torula or Pichia utilis.

In another embodiment, the method according to the invention makes use of a photosynthetic microorganism expressing at least a phosphoketolase and/or a sulfoacetaldehyde acetyltransferase. Preferably, the microorganism is a photosynthetic bacterium, or a microalgae. In a further embodiment the microorganism is an algae, more preferably an algae belonging to the diatomeae.

It is also conceivable to use in the method according to the invention a combination of microorganisms wherein different microorganisms express different enzymes as described above.

In a particularly preferred embodiment the method according to the invention makes use of a microorganism which is capable of producing a 2-hydroxyaldehyde as defined above. Such a microorganism may be either able to produce such a 2-hydroxyaldehyde naturally or due to a genetic modification which allows the microorganism to convert a metabolite or externally provided substrate into such a 2-hydroxyaldehyde. Some organisms have been described to be able to produce a 2-hydroxyaldehyde. For example, some archae bacteria, like Methanocaldococcus jannaschii, have been described to produce 2-hydroxypropanal (lactaldehyde; see Grochowski et al, J. Bacteriol. 188 (2006), 2836-2844; White, R H, Biochemistry 47, (2008), 5037-5046). Moreover, lactaldehyde is known to be a metabolic intermediate in the 1,2-propandiol pathway and is produced, e.g, in the L-fucose and R-rhamnose metabolism of E. coli (see, e.g, Boronat et Aguilar, J. Bacteriol. 147 (1981), 181-185; Bennet and San, Appl. Microbiol. Biotechnol. 55 (2001), 1-9).

The genetic modification of microorganisms to express an enzyme of interest will also be further described in detail below.

The phosphoketolase and/or sulfoacetaldehyde acetyltransferase used in the method according to the invention can be a naturally occurring phosphoketolase or sulfoacetaldehyde acetyltransferase or it can be a phosphoketolase/sulfoacetaldehyde acetyltransferase which is derived from a naturally occurring phosphoketolase/sulfoacetaldehyde acetyltransferase, e.g. by the introduction of mutations or other alterations which, e.g., alter or improve the enzymatic activity, the stability, etc.

The term "phosphoketolase" or "a protein/enzyme having the activity of a phosphoketolase" in the context of the present application also covers enzymes which are derived from a phosphoketolase, which are capable of producing an acyl phosphate from a 2-hydroxyaldehyde as defined above, but which only have a low affinity to their natural substrate or do no longer accept their natural substrate. Such a modification of the phosphoketolase as regards the preferred substrate allows to improve the conversion of a 2-hydroxyaldehyde into an acyl phosphate and to reduce the production of undesired by-products.

The term "sulfoacetaldehyde acetyltransferase" or "a protein/enzyme having the activity of a sulfoacetaldehyde acetyltransferase" in the context of the present application also covers enzymes which are derived from a sulfoacetaldehyde acetyltransferase, which are capable of producing an acyl phosphate from a 2-hydroxyaldehyde as defined above, but which only have a low affinity to their natural substrate or do no longer accept their natural substrate. Such a modification of the sulfoacetaldehyde acetyltransferase as regards the preferred substrate allows to improve the conversion of a 2-hydroxyaldehyde into an acyl phosphate and to reduce the production of undesired by-products.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic modification in prokaryotic cells, a nucleic acid molecule encoding phosphoketolase or a sulfoacetaldehyde acetyltransferase can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting phosphoketolase/sulfoacetaldehyde acetyltransferase variants are then tested for the desired activity, e.g., enzymatic activity, with an assay as described above and in particular for their increased enzyme activity.

As described above, the microorganism employed in a method of the invention or contained in the composition of the invention may be a microorganism which has been genetically modified by the introduction of a nucleic acid molecule encoding a phosphoketolase and/or a sulfoacetaldehyde acetyltransferase. Thus, in a preferred embodiment, the microorganism is a recombinant microorganism which has been genetically modified to have an increased phosphoketolase activity and/or an increased sulfoacetaldehyde acetyltransferase activity. This can be achieved e.g. by transforming the microorganism with a nucleic acid encoding a phosphoketolase and/or a sulfoacetaldehyde acetyltransferase. A detailed description of genetic modification of microorganisms will be given further below. Preferably, the nucleic acid molecule introduced into the microorganism is a nucleic acid molecule which is heterologous with respect to the microorganism, i.e. it does not naturally occur in said microorganism.

In the context of the present invention, an "increased activity" means that the expression and/or the activity of an enzyme, in particular of the phosphoketolase or the sulfoacetaldehyde acetyltransferase, in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme, e.g. a phosphoketolase or a sulfoacetaldehyde acetyltransferase, so that the corresponding expression/activity in the non-modified microorganism is zero.

Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of the phosphoketolase or sulfoacetaldehyde acetyltransferase are known in the art and have already been described above.

In the context of the present invention the term "recombinant" means that the microorganism is genetically modified so as to contain a nucleic acid molecule encoding an enzyme as defined above as compared to a wild-type or non-modified microorganism. A nucleic acid molecule encoding an enzyme as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The polynucleotide encoding the respective enzyme, in particular a phosphoketolase or a sulfoacetaldehyde acetyltransferase, is expressed so as to lead to the production of a polypeptide having any of the activities described above, e.g. phosphoketolase activity or sulfoacetaldehyde acetyltransferase activity. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

When the method according to the invention is carried out in vivo by using an organism/microorganism providing the respective enzyme activities, the organism, preferably microorganism, is cultivated under suitable culture conditions allowing the occurrence of the enzymatic reaction. The specific culture conditions depend on the specific organism/microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical reaction like the method of the present invention is carried out which involves an organisms, preferably microorganisms and/or active substances, i.e., the enzyme(s) described above derived from such organisms or organisms harbouring the above described enzyme(s). In a bioreactor or a fermenter, this process can either be aerobic or anaerobic. These bioreactors are commonly cylindrical, and may range in size from litres to cubic metres, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

The present invention also relates to a composition containing (a) a 2-hydroxyaldehyde and a phosphoketolase; or
(b) a 2-hydroxyaldehyde and a sulfoacetaldehyde acetyltransferase; or
(c) a 2-hydroxyaldehyde and a phosphoketolase and a sulfoacetaldehyde acetyltransferase; or
(d) a 2-hydroxyaldehyde and a microorganism expressing a phosphoketolase; or
(e) a 2-hydroxyaldehyde and a microorganism expressing a sulfoacetaldehyde acetyltransferase; or
(f) a 2-hydroxyaldehyde and a microorganism expressing a phosphoketolase and a sulfoacetaldehyde acetyltransferase, wherein the 2-hydroxyaldehyde responds to the following formula:

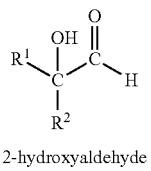

2-hydroxyaldehyde wherein $R^1$ and $R^2$ are selected independently from H, $C_3$, $CH_2OH$ and $C_2H5$ and wherein if $R^1$ is H, $R^2$ cannot be H.

The phosphoketolase/sulfoacetaldehyde acetyltransferase can be a phosphoketolase/sulfoacetaldehyde acetyltransferase as defined above in connection with the method according to the invention. The microorganism contained in the composition can be any suitable microorganism which expresses a phosphoketolase and/or a sulfoacetaldehyde acetyltransferase, in particular a microorganism as described herein above in connection with the method according to the invention.

The present invention furthermore relates to the use of a phosphoketolase or of a sulfoacetaldehyde acetyltransferase or of a microorganism expressing a phosphoketolase and/or sulfoacetaldehyde acetyltransferase for the production of an acyl phosphate from a 2-hydroxyaldehyde as defined herein above. As regards the phosphoketolase/sulfoacetaldehyde acetyltransferase and the microorganism, the same applies as has been set forth above in connection with a method according to the invention.

Figure 1:
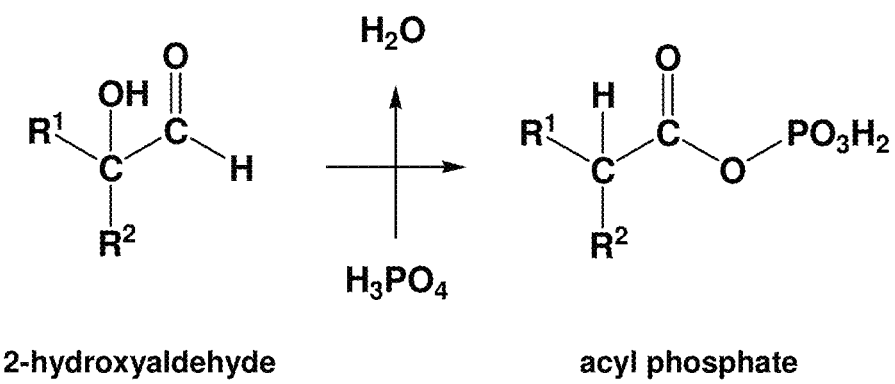
FIG. 1 shows schematically the conversion of a 2-hydroxyaldehyde into the corresponding acyl phosphate.
Figure 2:
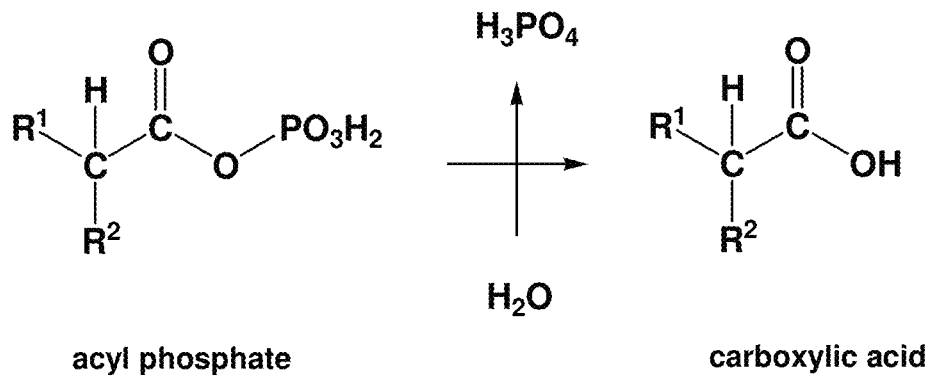
FIG. 2 shows schematically the conversion of acyl phosphate into the corresponding carboxylic acid.
Figure 2:
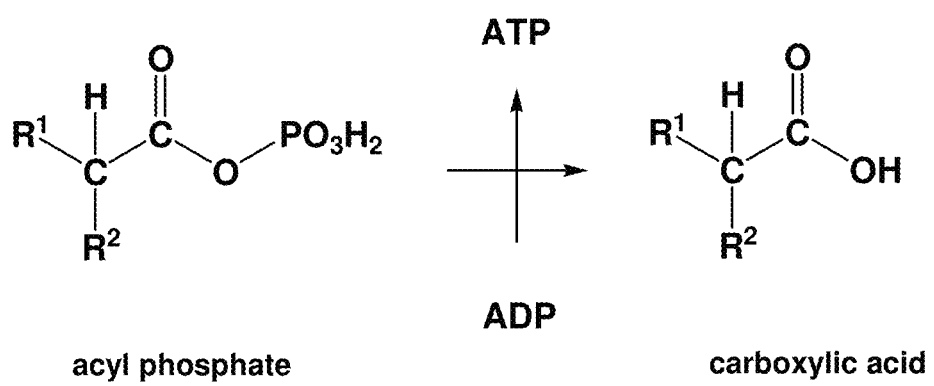
Figure 3:
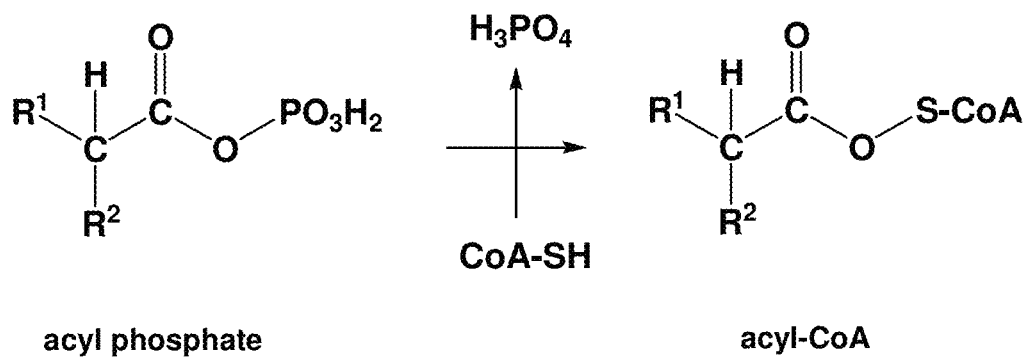
FIG. 3 shows schematically the conversion of acyl phosphate into the corresponding acyl-CoA.
Figure 4:
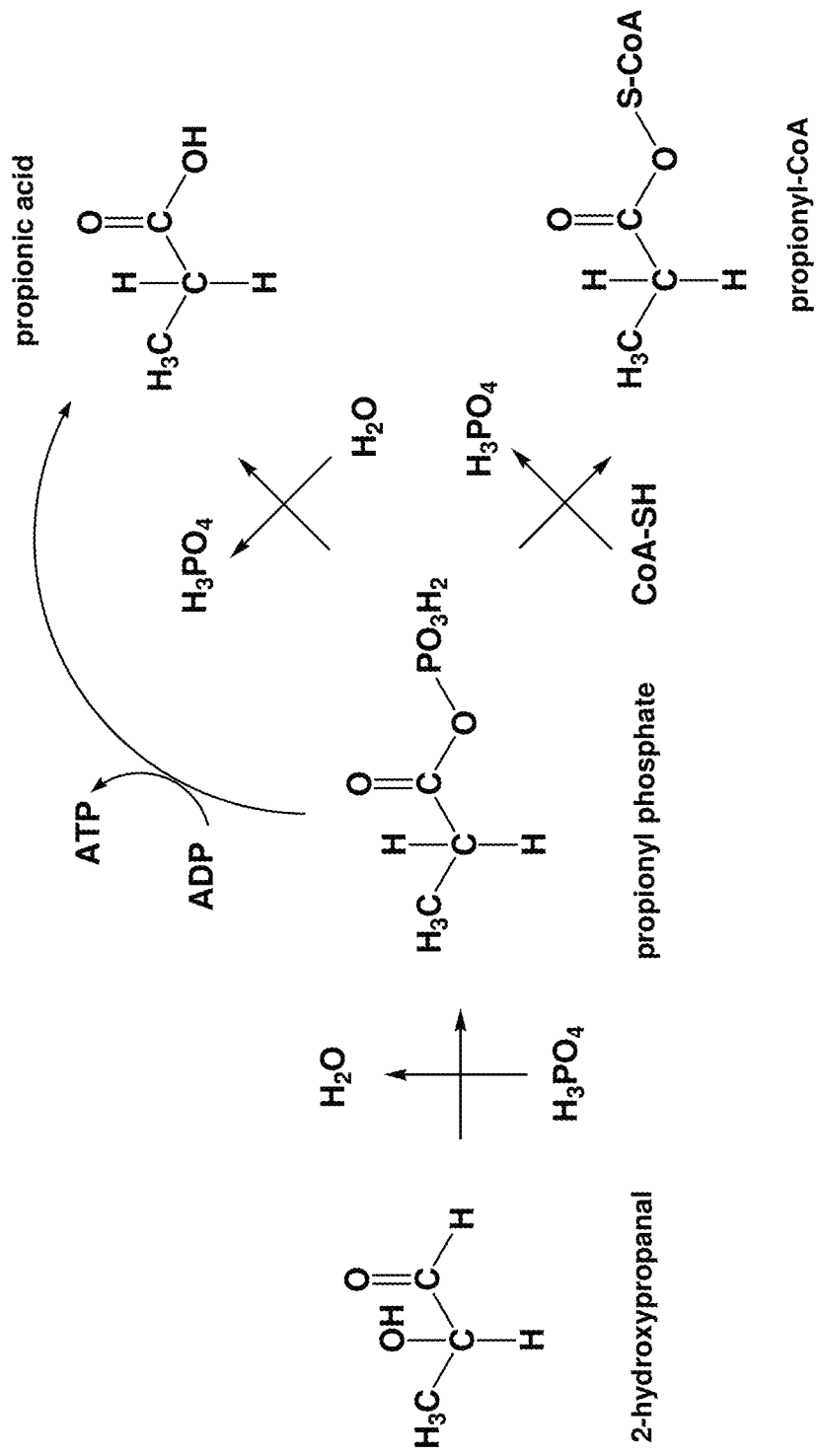
FIG. 4 shows schematically the conversion of 2-hydroxypropanal into propanoic acid or propionyl-CoA.
Figure 5:
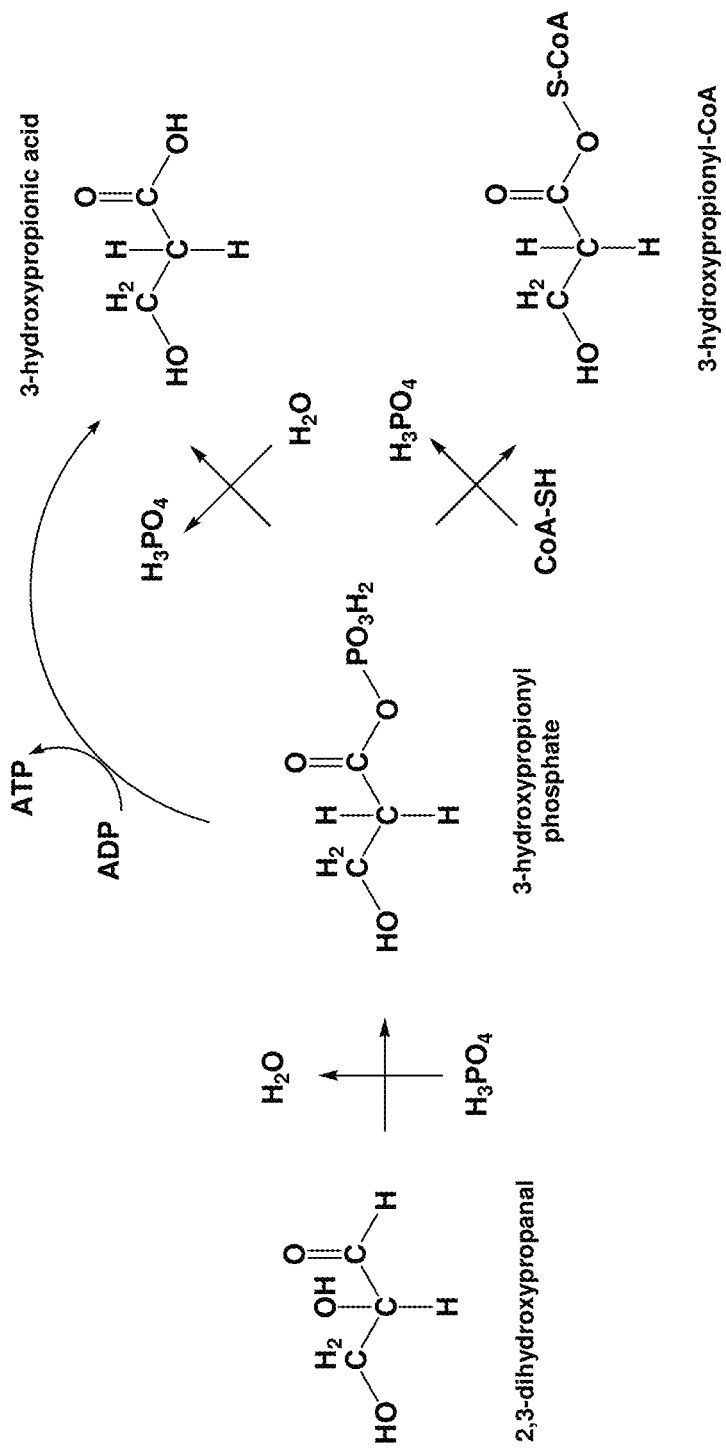
FIG. 5 shows schematically the conversion of 2,3-dihydroxypropanal into 3-hydroxypropanoic acid or 3-hydroxypropionyl-CoA.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

Example 1

Cloning, Expression and Purification of Phosphoketolases

Gene Synthesis, Cloning and Expression of Recombinant Enzymes

The sequences of phosphoketolases inferred from the genomes of prokaryotic organisms were generated by oligonucleotide concatenation to fit the codon usage of *E. coli* (genes were commercially synthesized by GeneArt®). A stretch of 6 histidine codons was inserted after the methionine initiation codon to provide an affinity tag for purification. The genes thus synthesized were cloned in a modified pUC18 expression vector (New England Biolabs) containing a modified Multiple Cloning Site (MCS). The genes of interest were cloned at PacI and NotI restriction sites.

Competent MG1655 *E. coli* cells were transformed with these vectors using standard heat shock procedure. The transformed cells were grown in LB-ampicillin medium for 24 h at 30° C., 160 rpm shaking.

The cells were collected by centrifugation at 4° C., 10,000 rpm for 20 min and the pellets were stored at −80° C.

Protein Purification and Concentration

The pellets from 200 ml of cultured cells were thawed on ice and resuspended in 3 ml of 50 mM Tris-HCl pH 7.5 containing 300 mM NaCl, 5 mM $MgCl_2$, 1 mM DTT and 10 mM Imidazole. 10 µl of lysonase (Merck) was added. Cells were incubated 10 minutes at room temperature and then returned to ice for 20 minutes. Cell lysis was completed by sonication for 2×30 seconds. The bacterial extracts were then clarified by centrifugation at 4° C., 10,000 rpm for 20 min. The clarified bacterial lysates were loaded on PROTINO-1000 Ni-TED column (Macherey-Nagel) allowing adsorption of 6-His tagged proteins. Columns were washed and the enzymes of interest were eluted with 4 ml of 50 mM Tris-HCl pH 7.5 containing 300 mM NaCl, 5 mM $MgCl_2$, 1 mM DTT, 250 mM Imidazole. Eluates were then concentrated, desalted on Amicon Ultra-4 10 kDa filter unit (Millipore) and enzymes were resuspended in 50 mM Tris-HCl pH 7.5. The enzyme preparation was complemented with 10% glycerol prior to long-term storage. Protein concentrations were quantified by direct UV 280 nm measurement on the NanoDrop 1000 spectrophotometer (Thermo Scientific). The purity of proteins thus purified varied from 70% to 90%.

Example 2

Study of the Formation of 3-Hydroxypropionyl Phosphate From 2,3-Dihydroxypropanal, Catalyzed by Phosphoketolase Enzymatic Reactions The enzymatic reactions were carried out under the following conditions:
50 mM Tris-HCl pH 7.5
25 mM Potassium phosphate pH 7.5
5 mM Thiamine pyrophosphate (TPP)
5 mM $MgCl_2$
23 mM Sodium fluoride
8 mM Sodium iodoacetate
1.9 mM L-Cysteine hydrochloride
50 mM 2,3-Dihydroxypropanal (D,L-glyceraldehyde) (Sigma)

The pH was adjusted to 7.5

Each enzymatic reaction was started by adding 3 mg/ml of purified recombinant phosphoketolase (PKT).

Control assays were performed in which either no enzyme was added, or no substrate was added.

Incubations were run overnight with shaking at 37° C. 3-hydroxypropionyl phosphate formation was studied through the detection of iron (III) 3-hydroxypropionyl-hydroxamate using the following procedure (Racker E., Methods Enzymol. 5, 1962, 276-280): 0.1 ml of hydroxylamine hydrochloride (2 M, pH 6.5) was added to 0.1 ml of reaction mixture. After 10 min of incubation at room temperature the samples were acidified with 35 µl of 30% trichloroacetic acid. 35 µl of 8 M HCl and 35 µl of $FeCl_3$ reagent (10% $FeCl_3$ in 0.1 M HCl) were then added. The samples were further clarified by centrifugation and the absorbance of ferric 3-hydroxypropionyl-hydroxamate complex was measured at 505 nm.

A low signal of absorbance was observed in the control assays in which either no phosphoketolase was added, or no 2,3-dihydrpoxypropanal was added. Absorbance values of the enzymatic samples corrected by subtraction of the control assay without enzyme, are shown in Table 1.

TABLE 1

| Enzymatic assay with phosphoketolase (PKT) | Uniprot Accession Number | Absorbance at 505 nm |
|---|---|---|
| PKT from Bifidobacterium pseudolongum subsp. globosum | Q6R2Q6 (SEQ ID NO: 1) | 0.024 |
| PKT from Lactococcus lactis subsp. lactis strain KF147 | A9QST6 (SEQ ID NO: 3) | 0.012 |
| PKT from Clostridium acetobutylicum strain ATCC 824 | Q97JE3 (SEQ ID NO: 2) | 0.120 |
| PKT from Bifidobacterium gallicum DSM 20093 | D1NS90 (SEQ ID NO: 16) | 0.020 |
| PKT from Leuconostoc citreum (strain KM20) | B1MWV8 (SEQ ID NO: 17) | 0.014 |

TABLE 1-continued

| Enzymatic assay with phosphoketolase (PKT) | Uniprot Accession Number | Absorbance at 505 nm |
|---|---|---|
| PKT from Streptococcus gordonii (strain Challis/ATCC 35105/CH1/DL1/V288) | A8AV21 (SEQ ID NO: 18) | 0.088 |

Example 3

Study of the Formation of Propionyl Phosphate From 2-Hydroxypropanal Catalyzed by Phosphoketolase The enzymatic assays were carried out according to the protocol described in Example 2. 2-hydroxypropanal (lactaldehyde) was used as substrate instead of 2,3 dihydroxypropanal.

Hydroxamate-Based Colorimetric Assay

Propionyl phosphate formation was studied through the detection of iron (III) propionyl-hydroxamate using the procedure described in Example 2. A low signal of absorbance was observed in the control assays in which either no phosphoketolase was added, or no 2-hydroxypropanal was added. Absorbance values of the enzymatic samples corrected by subtraction of the control assay without enzyme, are shown in Table 2.

TABLE 2

| Enzymatic assay with phosphoketolase (PKT) | Uniprot Accession Number | Absorbance at 505 nm |
|---|---|---|
| PKT from Bifidobacterium pseudolongum subsp. globosum | Q6R2Q6 (SEQ ID NO: 1) | 0.006 |
| PKT from Clostridium acetobutylicum strain ATCC 824 | Q97JE3 (SEQ ID NO: 2) | 0.004 |
| PKT from Thiobacillus denitrificans (strain ATCC 25259) | Q3SKJ7 (SEQ ID NO: 19) | 0.008 |

Thus, different phosphoketolases were shown to catalyze the conversion of a 2-hydroxyaldehyde into the corresponding acyl phosphate.

Example 4

Cloning, Expression and Purification of Sulfoacetaldehyde Acetyltransferases

Gene Synthesis, Cloning and Expression of Recombinant Proteins

The sequences of the studied enzymes inferred from the genomes of prokaryotic organisms were generated by oligonucleotide concatenation to fit the codon usage of E. coli (genes were commercially synthesized by GeneArt®). A stretch of 6 histidine codons was inserted after the methionine initiation codon to provide an affinity tag for purification. The genes thus synthesized were cloned in a pET-25b (+) expression vector (vectors were constructed by GeneArt®).

Competent E. coli BL21(DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41, (2005), 207-234) for 7 h at 30° C. and protein expression was continued at 18° C.

overnight (approximately 16 h). The cells were collected by centrifugation at 4° C., 10,000 rpm for 20 min and the pellets were stored at −80° C.

Protein Purification and Concentration

The pellets from 200 ml of culture cells were thawed on ice and resuspended in 5 ml of 50 mM Tris-HCl buffer pH 7.5 containing 300 mM NaCl, 10 mM MgCl$_2$, 10 mM imidazole and 1 mM DTT. Twenty microliters of lysonase (Novagen) were added. Cells were incubated 10 minutes at room temperature and then returned to ice for 20 minutes. Cell lysis was completed by sonication for 2×30 seconds. The bacterial extracts were then clarified by centrifugation at 4° C., 4000 rpm for 40 min. The clarified bacterial lysates were loaded onto a PROTINO-2000 Ni-TED column (Macherey-Nagel) allowing adsorption of 6-His tagged proteins. Columns were washed and the enzymes of interest were eluted with 6 ml of 50 mM Tris-HCl buffer pH 7.5 containing 300 mM NaCl, 5 mM MgCl2, 1 mM DTT and 250 mM imidazole. Eluates were then concentrated, desalted on Amicon Ultra-4 10 kDa filter unit (Millipore) and enzymes were resuspended in 50 mM Tris-HCl buffer pH 7.5. The purity of proteins thus purified varied from 70% to 90% as estimated by SDS-PAGE analysis. Protein concentrations were determined by direct UV 280 nm measurement on the NanoDrop 1000 spectrophotometer (Thermo Scientific) or by Bradford assay (BioRad).

Example 5

HPLC-Based Analysis of the Conversion of D,L-Lactaldehyde (2-Hydroxypropanal) into Propionyl Phosphate and Further into Propionic Acid The phosphoketolases were expressed and purified as described in Example 1.

The sulfoacetaldehyde acetyltransferases were expressed as described in Example 4.

Enzyme Reaction

The enzymatic reactions were carried out under the following conditions:
50 mM Tris-HCl pH 7.5
With or without 25 mM sodium phosphate pH 7.5
0.6 mM thiamine pyrophosphate (TPP)
1 mM MgCl$_2$
1.9 mM L-cysteine hydrochloride
50 mM D, L-lactaldehyde (Sigma-Aldrich)
2.8 mg/ml purified enzyme
Total volume 150 µl.

A control assay was performed in which no enzyme was added. Enzymatic assays were conducted overnight at 37° C. The formation of propionic acid was studied using HPLC-based analysis.

HPLC-Based Method

The enzymatic reactions were stopped by a 5-min incubation at 80° C. Then, 150 µl MeCN was added in the medium, and the assay tubes were centrifuged. 100 µl of the clarified supernatant was filtered, and transferred into a clean vial.

HPLC analyses were performed using a 1260 Infinity LC System (Agilent), equipped with a refractometer detector and a column heating module. 5 µl sample was separated on Hi-Plex H column (100×7.7 mm, 8 µm particle size, column temp. 65° C.) equipped with a PL Hi-Plex H Guard Column (50×7.7 mm). The mobile phase consisted of aqueous sulfuric acid (1 mM) and was run with a flow rate of 0.8 ml/min. Retention time of D,L-lactaldehyde and propionic acid under these conditions were 4.94 and 6.62 min, respectively.

Several phosphoketolases or sulfoacetaldehyde acetyltransferases were able to catalyze the conversion of D,L-lactaldehyde into propionic acid (Table 3). The formation of propionic acid was improved in the presence of inorganic phosphate, indicating that the conversion takes place through an acyl-phosphate as intermediate. The acyl phosphate which is rather unstable is converted into propionic acid by way of spontaneous hydrolysis.

TABLE 3

| | enzyme | organism | uniprot accession number | propionic acid mM |
|---|---|---|---|---|
| With 50 mM phopshate | Sulfoacetaldehyde acetyltransferase | Castellaniella defragans (SEQ ID NO: 4) | O84H44 | 1.1 |
| | Sulfoacetaldehyde acetyltransferase | Alcaligenes xyloxydans (SEQ ID NO: 5) | Q84H41 | 0.5 |
| | Sulfoacetaldehyde acetyltransferase | Roseovarius nubinhibens (SEQ ID NO: 8) | A35R25 | 1.8 |
| | Sulfoacetaldehyde acetyltransferase | Desulfonispora thiosulfatigenes (SEQ ID NO: 6) | Q93PS3 | 0.4 |
| | Phosphoketolase | Streptococcus gordonii (SEQ ID NO: 18) | A8AV21 | 5.1 |
| | Phosphoketolase | Lactococcus lactis (SEQ ID NO: 3) | A9QST6 | 6.9 |
| | Phosphoketolase | Lactococcus crispatus (SEQ ID NO: 20) | D5H215 | 0.8 |
| | control without enzyme | | | 0.0 |
| Without 50 mM phosphate | Sulfoacetaldehyde acetyltransferase | Castellaniella defragans | Q84H44 | 0.2 |
| | Sulfoacetaldehyde acetyltransferase | Alcaligenes xyloxydans | Q84H41 | 0.2 |
| | Sulfoacetaldehyde acetyltransferase | Roseovarius nubinhibens | A3SR25 | 2.1 |
| | Sulfoacetaldehyde acetyltransferase | Desulfonispora thiosulfatigenes | Q93PS3 | 0.3 |
| | Phosphoketolase | Streptococcus gordonii | A8AV21 | 0.6 |
| | Phosphoketolase | Lactococcus lactis | A9QST6 | 1.6 |
| | Phosphoketolase | Lactococcus crispatus | D5H215 | 0.4 |
| | control without enzyme | | | 0.0 |

Example 6

HPLC-Based Analysis of the Conversion of D,L-Glyceraldehyde (2,3-Hydroxypropanal) into 3-Hydroxypropionyl Phosphate and Further into 3-Hydroxypropionic Acid All the phosphoketolases were expressed and purified as described in Example 1.

The sulfoacetaldehyde acetyltransferases were expressed as described in Example 4.

Enzyme Reaction

The enzymatic reactions were carried out under the following conditions:
50 mM Tris-HCl pH 7.5
With or without 25 mM sodium phosphate pH 7.5
0.6 mM thiamine pyrophosphate (TPP)
1 mM MgCl$_2$ 1.9 mM L-cysteine hydrochloride
50 mM D,L-glyceraldehyde (Sigma)
2.8 mg/ml purified enzyme
Total volume of the reaction was 150 µl.

A control assay was performed in which no enzyme was added. Enzymatic assays were conducted overnight at 37° C. The formation of 3-hydroxypropionic acid was studied using HPLC-based analysis.

HPLC-Based Method

The enzymatic reactions were stopped by a 5-min incubation at 80° C. Then, 150 µl MeCN was added in the medium, and the assay tubes were centrifuged. 100 µl of the clarified supernatant was filtered, and transferred into a clean vial.

The amount of 3-hydroxypropionic acid produced was measured using a HPLC-based procedure. HPLC analysis was performed using a 1260 Infinity LC System Agilent, equipped with column heating module, and refractometer. 5 µl of samples were separated using 3 columns connected in series as follows:
1. Hi-Plex guard column (50×7.7 mm, 8 µm particle size) (Agilent)
2. Hi-Plex column (100×7.7 mm, 8 µm particle size) (Agilent)
3. Zorbax SB-Aq column (250×4.6 mm, 5 µm particle size, column temp. 65° C.) (Agilent).

The mobile phase consisted of aqueous sulfuric acid (1 mM), mobile phase flow rate was 0.5 ml/min. Retention time of D,L-glyceraldehyde and 3-hydroxypropionic acid under these conditions were 12.12 and 14.67 min, respectively.

Several phosphoketolases or sulfoacetaldehyde acetyltransferases were able to catalyze the conversion of D,L-glyceraldehyde into 3-hydroxypropionic acid (Table 4). The conversion is considered to take place via the intermediate 3-hydroxypropionyl phosphate which is rather unstable and is spontaneously hydrolyzed to 3-hydroxypropionic acid.

TABLE 4

|  | enzyme | organism | uniprot accession number | 3-hydroxypropionic acid mM |
|---|---|---|---|---|
| with 50 mM phopshate | Sulfoacetaldehyde acetyltransferase | *Castellaniella defragans* | Q84H44 | 0.2 |
|  | Sulfoacetaldehyde acetyltransferase | *Alcaligenes xyloxydans* | Q84H41 | 0.1 |
|  | Sulfoacetaldehyde acetyltransferase | *Roseovarius nubinhibens* | A3SR25 | 0.3 |
|  | Sulfoacetaldehyde acetyltransferase | *Desulfonispora thiosulfatigenes* | Q93PS3 | 0.1 |
|  | Phosphoketolase | *Streptococcus gordonii* | A8AV21 | 2.1 |
|  | Phosphoketolase | *Lactococcus lactis* | A9QST6 | 0.8 |
|  | Phosphoketolase | *Lactococcus crispatus* | D5H215 | 0.3 |
|  | control without enzyme |  |  | 0.2 |
| without 50 mM phosphate | Sulfoacetaldehyde acetyltransferase | *Castellaniella defragans* | Q84H44 | 0.1 |
|  | Sulfoacetaldehyde acetyltransferase | *Alcaligenes xyloxydans* | Q84H41 | 0.1 |
|  | Sulfoacetaldehyde acetyltransferase | *Roseovarius nubinhibens* | A3SR25 | 0.4 |
|  | Sulfoacetaldehyde acetyltransferase | *Desulfonispora thiosulfatigenes* | Q93PS3 | 0.2 |
|  | Phosphoketolase | *Streptococcus gordonii* | A8AV21 | 1.1 |
|  | Phosphoketolase | *Lactococcus lactis* | A9QST6 | 1.3 |
|  | Phosphoketolase | *Lactococcus crispatus* | D5H215 | 1.2 |
|  | control without enzyme |  |  | 0.1 |

The invention claimed is:

1. A method for the enzymatic production of an acyl phosphate, wherein 2-hydroxyaldehyde and phosphate is enzymatically converted to an acyl phosphate by a phosphoketolase, wherein said phosphoketolase is selected form EC 4.1.2.9, EC 4.1.2.22 or any one of SEQ ID NO:1-3 or 16-20, or a sulfoacetaldehyde acetyltransferase (EC 2.3.3.15) according to the following reaction scheme:

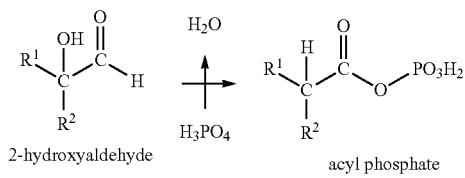

wherein $R^1$ and $R^2$ are selected independently from H, $CH_3$, $CH_2OH$ and $C_2H_5$ and wherein if $R^1$ is H, $R^2$ cannot be H, wherein said method is carried out in an in vitro, cell-free system or by a recombinant microorganism or plant cell overexpressing said phophoketolase or sulfoacetaldehyde acetyltransferase.

2. The method of claim 1, wherein the acyl phosphate is recovered.

3. The method of claim 1 which further comprises converting the acyl phosphate into a carboxylic acid according to the following reaction scheme:

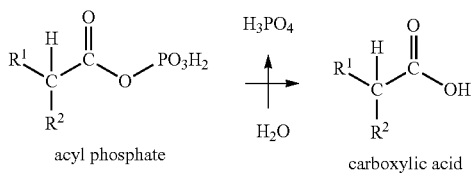

wherein $R^1$ and $R^2$ are selected independently from H, $CH_3$, $CH_2OH$ and $C_2H_5$ and wherein if $R^1$ is H, $R^2$ cannot be H.

4. The method of claim 3, wherein the conversion of the acyl phosphate into the carboxylic acid is achieved by an acylphosphatase (EC 3.6.1.7).

5. The method of claim 1 which further comprises converting the acyl phosphate into a carboxylic acid according to the following reaction scheme:

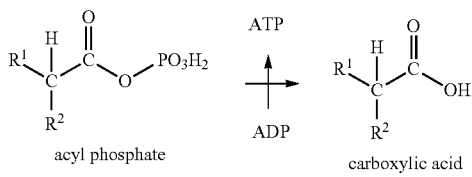

wherein $R^1$ and $R^2$ are selected independently from H, $CH_3$, $CH_2OH$ and $C_2H_5$ and wherein if $R^1$ is H, $R^2$ cannot be H.

6. The method of claim 5, wherein the conversion of the acyl phosphate into the carboxylic acid is achieved by an enzyme which is classified as a phosphotransferase with a carboxyl group as acceptor (EC 2.7.2).

7. The method of claim 6, wherein the phosphotransferase is an acetate kinase (EC 2.7.2.1), a butyrate kinase (EC 2.7.2.7), an acetate kinase (diphosphate) (EC 2.7.2.12), a branched-chain-fatty-acid kinase (EC 2.7.2.14) or of a propionate kinase (EC 2.7.2.15).

8. The method of claim 1 which further comprises enzymatically converting the acyl phosphate into an acyl-coenzyme A according to the following reaction scheme:

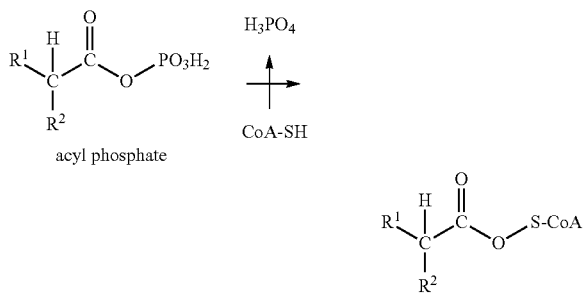

wherein $R^1$ and $R^2$ are selected independently from H, $CH_3$, $CH_2OH$ and $C_2H_5$ and wherein if $R^1$ is H, $R^2$ cannot be H.

9. The method of claim 8, wherein the conversion of the acyl phosphate into the acyl-coenzyme A is achieved by a phosphate acetyltransferase (EC 2.3.1.8) or of a phosphate butyryltransferase (EC 2.3.1.19).

10. The method of claim 1, wherein the 2-hydroxyaldehyde is 2-hydroxypropanal.

11. The method of claim 1, wherein the 2-hydroxyaldehyde is 2,3-dihydroxypropanal.

12. A composition comprising
(a) an in vitro cell free system comprising 2-hydroxyaldehyde and a phosphoketolase wherein said phosphoketolase is selected from EC 4.1.2.9, EC 4.1.2.22 or any one of SEQ ID NO:1-3 or 16-20 and/or a sulfoacetaldehyde acetyltransferase (EC 2.3.3.15); or
(b) 2 hydroxyaldehyde and a recombinant microorganism or plant cell overexpressing a phosphoketolase wherein said phosphoketolase is selected from EC 4.1.2.9, EC 4.1.2.22 or any one of SEQ ID NO:1-3 or 16-20 and/or a sulfoacetaldehyde acetyltransferase (EC 2.3.3.15).

13. The method of claim 1, wherein the phosphoketolase and the sulfoacetaldehyde acetyltransferase is overexpressed by the recombinant microorganism or plant cell.

14. The method of claim 1, wherein the method is carried out in the recombinant microorganism or plant cell.

15. The method of claim 1, wherein the method is carried out in an in vitro, cell-free system.

16. The method of claim 3, wherein the method is carried out in the recombinant microorganism or plant cell.

17. The method of claim 4, wherein the acylphosphatase (EC 3.6.1.7) is overexpressed by the recombinant microorganism or plant cell.

18. The method of claim 5, wherein the method is carried out in the recombinant microorganism or plant cell.

19. The method of claim 6, wherein the phosphotransferase with a carboxyl group as acceptor (EC 2.7.2) is overexpressed by the recombinant microorganism or plant cell.

20. The method of claim 7, wherein the acetate kinase (EC 2.7.2.1), the butyrate kinase (EC 2.7.2.7), the acetate kinase (diphosphate) (EC 2.7.2.12), the branched-chain-fatty-acid kinase (EC 2.7.2.14) or the propionate kinase (EC 2.7.2.15) is overexpressed by the recombinant microorganism or plant cell.

21. The method of claim 1, wherein the recombinant microorganism or plant cell is genetically modified to overexpress the phosphoketolase or the sulfoacetaldehyde acetyltransferase, wherein the genetic modification is selected from:
 (a) operably associating a heterologous promoter with a polynucleotide encoding the phosphoketolase or the sulfoacetaldehyde acetyltransferase;
 (b) transforming a heterologous polynucleotide encoding the phosphoketolase or the sulfoacetaldehyde acetyltransferase into the recombinant microorganism or plant cell; and/or
 (c) introducing a mutation in the promoter of a polynucleotide encoding the phosphoketolase or sulfoacetaldehyde acetyltransferase wherein said mutation results in overexpression of the polynucleotide.

22. The composition of claim 12, wherein the composition further comprises an acylphosphatase (EC 3.6.1.7).

23. The composition of claim 22, wherein the acylphosphatase (EC 3.6.1.7) is overexpressed by the recombinant microorganism or plant cell.

24. The composition of claim 12, wherein the composition further comprises a phosphotransferase with a carboxyl group as acceptor (EC 2.7.2).

25. The composition of claim 24, wherein the phosphotransferase is an acetate kinase (EC 2.7.2.1), a butyrate kinase (EC 2.7.2.7), an acetate kinase (diphosphate) (EC 2.7.2.12), a branched-chain-fatty-acid kinase (EC 2.7.2.14) or of a propionate kinase (EC 2.7.2.15).

26. The composition of claim 24, wherein the phosphotransferase with a carboxyl group as acceptor (EC 2.7.2) is overexpressed by the recombinant microorganism or plant cell.

27. The composition of claim 26, wherein the acetate kinase (EC 2.7.2.1), the butyrate kinase (EC 2.7.2.7), the acetate kinase (diphosphate) (EC 2.7.2.12), the branched-chain-fatty-acid kinase (EC 2.7.2.14) or the propionate kinase (EC 2.7.2.15) is overexpressed by the recombinant microorganism or plant cell.

28. The composition of claim 12, wherein the composition further comprises a phosphate acetyltransferase (EC 2.3.1.8) or a phosphate butyryltransferase (EC 2.3.1.19).

29. The composition of claim 12, wherein the 2-hydroxyaldehyde is 2-hydroxypropanal.

30. The composition of claim 12, wherein the 2-hydroxyaldehyde is 2,3-dihydroxypropanal.

31. The composition of claim 12, wherein the composition is the in vitro cell free system.

32. The composition of claim 12, wherein the composition comprises the recombinant microorganism or plant cell.

33. The composition of claim 12, wherein the recombinant microorganism or plant cell is genetically modified to overexpress the phosphoketolase or the sulfoacetaldehyde acetyltransferase, wherein the genetic modification is selected from:
 (a) operably associating a heterologous promoter with a polynucleotide encoding the phosphoketolase or the sulfoacetaldehyde acetyltransferase;
 (b) transforming a heterologous polynucleotide encoding the phosphoketolase or the sulfoacetaldehyde acetyltransferase into the recombinant microorganism or plant cell; and/or
 (c) introducing a mutation in the promoter of a polynucleotide encoding the phosphoketolase or sulfoacetaldehyde acetyltransferase wherein said mutation results in overexpression of the polynucleotide.

* * * * *